United States Patent [19]

Cooper et al.

[11] Patent Number: 5,008,263

[45] Date of Patent: Apr. 16, 1991

[54] DIAZEPINE ANTIALLERGY AGENTS

[75] Inventors: Kelvin Cooper, Deal; Michael J. Fray, Nr. Canterbury, both of England

[73] Assignee: Pfizer Inc., New York, N.Y.

[21] Appl. No.: 496,393

[22] Filed: Mar. 20, 1990

[30] Foreign Application Priority Data

Mar. 23, 1989 [GB] United Kingdom ................. 8906813
Nov. 21, 1989 [GB] United Kingdom ................. 8926246

[51] Int. Cl.[5] ..................... A61K 31/55; C07D 521/00

[52] U.S. Cl. .................................... 514/220; 514/219; 514/221; 540/495; 540/496; 540/497; 540/517; 540/502; 540/503; 540/555; 540/559; 540/560; 540/561; 540/562; 540/563; 540/564; 540/567; 540/568

[58] Field of Search ............... 540/495, 517, 502, 503, 540/555, 559, 560, 561, 562, 563, 564, 567, 568, 496, 497; 514/219, 220, 221

[56] References Cited

FOREIGN PATENT DOCUMENTS 230942 1/1987 European Pat. Off. ............ 540/578

*Primary Examiner*—Robert T. Bond
*Attorney, Agent, or Firm*—Peter C. Richardson; J. Trevor Lumb; A. Dean Olson

[57] ABSTRACT

Platelet activating factor antagonists of formula (I), (II) or (III):

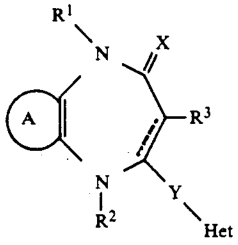

(I)

or

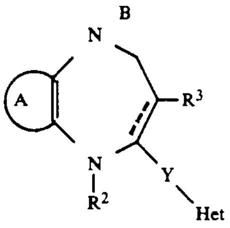

(II)

or

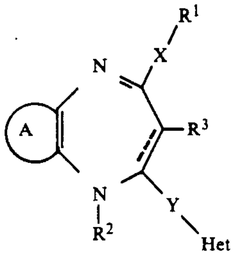

(III)

where

A is optionally substituted benzene, pyridine, naphthalene, quinoline, thiophene, benzothiophene, pyrazole or isothiazole, X is O, S or NH Y is 1,4 phenylene or a group of formula

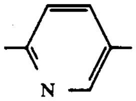

$R^1$ is H or optionally substituted $C_1$-$C_4$ alkyl, $R^2$ and $R^3$ are H or $C_1$-$C_4$ alkyl, B is an optionally fused 5- or 6-membered ring containing nitrogen atoms, Het is an optionally substituted 5-membered heterocyclic ring containing nitrogen or a pyridine ring, the ring optionally being fused to benzene or nitrogen-containing heterocyclic ring.

7 Claims, No Drawings

DIAZEPINE ANTIALLERGY AGENTS

This invention relates to diazepine derivatives which are potent, orally active antagonists of platelet activating factor and as such have clinical utility for treating allergic and inflammatory conditions such as asthma and arthritis respectively.

Platelet activating factor (PAF, 1-0-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukctrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic and inflammatory conditions such as asthma and arthritis, respectively.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF levels are increased by endotoxin infusion indicate that PAF is a prime mediator in certain forms of shock. Intravenous infusion of PAF at doses of 20-200 pmol $kg^{-1}$ $min^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing and, in pigs, intracoronary injection of PAF induces a prolonged decrease in coronary flow while in guinea pig hearts it induces regional shunting and ischaemia. PAF has also been shown to initiate thrombus formation in a mesenteric artery preparation both when administered exogenously and when released endogenously. More recently PAF has been shown to play a role in brain ischaemia induced in animal models of stroke.

Thus compounds of the invention, by virtue of their ability to antagonise the actions of PAF, could well be of value in the treatment of any of the above conditions.

According to the invention there are provided compounds of formula (I), (II) or (III).

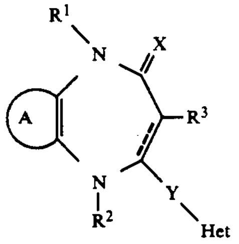

(I)

or

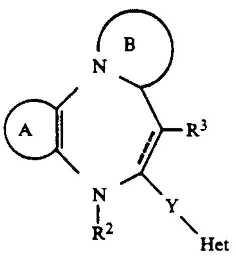

(II)

or

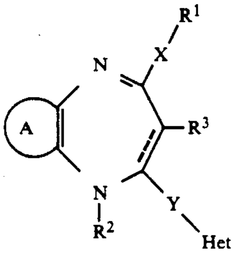

(III)

wherein

A represents a fused benzene, pyridine, naphthalene, quinoline, thiophene, benzothiophene, pyrazole or isothiazole ring, which ring or rings being optionally substituted by 1 or 2 substituents independently selected from $C_1$-$C_4$ alkyl; $C_4$-$C_7$ cycloalkyl; halo; perfluoro - ($C_1$-$C_4$ alkyl); cyano; ($C_1$-$C_4$ alkoxy)carbonyl; nitro; amino; amino substituted by ($C_1$-$C_4$ alkyl) sulfonyl, amino substituted by ($C_1$-$C_4$ alkyl) oxalyl; $C_1$-$C_4$ alkoxy - ($C_1$-$C_4$ alkyl) imino; hydroxy($C_1$-$C_4$ alkyl), ($C_1$-$C_4$ alkoxy)-$C_1$-$C_4$ alkyl, ($C_1$-$C_4$ alkoxy)-($C_2$-$C_4$ alkoxy)-$C_1$-$C_4$ alkyl, —$CONR^5R^6$ wherein $R^5$ and $R^6$ are each independently H or $C_1$-$C_6$ alkyl, or $R^5$ is H or $C_1$-$C_4$ alkyl and $R^6$ is $C_3$-$C_7$ cycloalkyl, or 2-pyridyl, or $R^5$ and $R^6$ are joined together to form, with the nitrogen atom to which they are attached, a morpholino, pyrrolidino or piperidino group; and phenyl, thienyl or pyridyl optionally substituted by halogen, cyano, trifluoromethyl, ($C_1$-$C_4$ alkoxy) carbonyl or carbamoyl, X is O, S or NH Y is 1, 4 phenylene or a group of formula $R^1$ is either H or $C_1$-$C_4$ alkyl optionally substituted by a substituent selected from phenyl, halophenyl, pyridyl, ($C_1$-$C_4$ alkoxy) carbonyl and di-($C_1$-$C_4$ alkyl) amino, or $C_2$-$C_4$ alkyl substituted by hydroxyl or by one or two $C_1$-$C_4$ alkoxy groups or is $(CH_2)_nCONR^7R^8$ where n=1-4 and R and $R^8$ are each independently H or $C_1$-$C_4$ alkyl.

$R^2$ is H or $C_1$-$C_4$ alkyl;

$R^3$ is H or $C_1$-$C_4$ alkyl;

B represents a fused 5-membered heterocyclic ring containing from 1 to 4 nitrogen atoms or a fused 6-membered heterocyclic ring containing two nitrogen atoms said fused 5- or 6-membered ring being optionally substituted by 1 or 2 substituents independently selected from $C_1$–$C_4$ alkyl, $C_1$–$C_4$ haloalkyl, halo and oxo;

and "Het" is either a 5-membered aromatic heterocyclic ring containing two or three nitrogen atoms or a pyridine ring; which ring may optionally be fused to a benzene or pyridine ring or to a further 5-membered aromatic heterocyclic ring, at least one of said heterocyclic rings optionally containing a sulphur or oxygen atom and at least one of said rings optionally being substituted with from one to three substituents independently selected from $C_1$–$C_4$ alkyl, $C_1$–$C_4$ alkoxy, halo, $CF_3$, CN and formyl;

and wherein the dashed line represents an optional bond;

and their pharmaceutically acceptable salts.

In the definitions given herein the term "halo" means fluoro, chloro, bromo or iodo. Alkyl and alkoxy groups of 3 or more carbon atoms may be straight or branched-chain. Examples of the fused ring represented by A include benzene, dimethylbenzene, dichlorobenzene, nitrobenzene, aniline, fluorobenzene, chlorobenzene, pyridine, quinoline, methylpyridine, dimethylpyridine, ethoxycarbonylpyridine, pyrid-2-yl carbamoylpyridine, morpholinocarbonylpyridine, diethylcarbamoylpyridine, t-butylcarbamoylpyridine, thiophene, 2-methoxycarbonyl-5-methyl-thiophene, 1-methyl-3-phenylpyrazole, 1-phenyl-3-methylpyrazole, 1-methyl-3-t-butylpyrazole, 1,2-dimethylpyrazole, 1,3-dimethylpyrazole, 1-pyrid-2-yl-3-methyl-pyrazole, 1-t-butyl-3-methylpyrazole, 1-(2-hydroxyethyl)-3-methyl-pyrazole, 1-methyl-3-pyrid-3-ylpyrazole, 1-methyl-3-pyrid-4-ylpyrazole, 1-methyl-3-pyrid-2-ylpyrazole, 1-(2-hydroxyethyl)-3-phenyl-pyrazole, 3-(2-methoxyethoxy)methyl-1-methylpyrazole, 1-methyl-3-cyclohexylpyrazole, 1-methyl-3(t-butylhydroxymethyl)-pyrazole, 1-methyl-3-hydroxymethylpyrazole, 3-cyclohexylpyrazole, 1-methyl-3-(isobutoxymethyl)pyrazole, 1methyl-3-(4-chlorophenyl)pyrazole, 1-methyl-3-isopropyl pyrazole, 1-pyrid-2-yl-3-phenylpyrazole, 1-methyl-3-(2-chlorophenyl)pyrazole, 1-methyl-3-(3-trifluoromethylphenyl)pyrazole, 1-methyl-3-thienyl pyrazole, bromopyridine, 1-ethoxyethylimino benzene, N-ethylsulphoxyaniline, 3-methylisothiazole and ethoxycarbonylcarbamidobenzene.

Examples of $R^1$ are H, methyl, ethyl, benzyl, 4-chlorobenzyl, $-CH_2CO_2Et$, $-CH_2CH_2N(CH_3)_2$ and , $CH_2CON(CH_3)_2$, $CH_2CH_2CH(OCH_3)_2$ and 4-hydroxybutyl. Examples of the fused ring represented by B are imidazole, methyl imidazole, triazole, methyltriazole, trifluoromethyltriazole, triazolone, tetrazole, pyrimidone, imidazoline and tetrahydropyrimidine.

$R^2$ is preferably hydrogen or methyl. $R^3$ is preferably hydrogen or methyl.

Examples of "Het" are dimethylpyridyl, 1,2,4-triazolyl optionally substituted with one or two $C_1$–$C_4$ alkyl groups and imidazolyl optionally substituted with up to three groups selected from $C_1$–$C_4$ alkyl, halo and formyl or optionally substituted with a $C_1$–$C_4$ alkyl or $CF_3$ group and fused to a benzene, thiazole or pyridine ring. "Het" is preferably 2-methylimidazo[4,5-c]pyrid-1-yl, 2,4,6-trimethylimidazo[4,5-c]pyrid-1-yl, 3,5-dimethyl-1,2, 4-triazol-4-yl, 1,6-dimethylpyrid-3-yl, 5-chloro-2-methylimidazol-1-yl, 5-chloro-4-formyl-2-methylimidazol-1-yl or 4-methylimidazo[2,1-b]thiazol-5-yl.

Particularly preferred compounds are 8,9-dichloro-5-[4-(2-methyl-1H-imidazo[4,5-c]pyrid-1-yl) phenyl]-4H-imidazo[1,2-a][1,5]benzodiazepine, 8,9-dichloro-1-methyl-5-[4-(2-methylimidazo[4,5-c]pyrid-1-yl)phenyl]-4H-imidazo[1,2-a][1,5]benzodiazepine; 3,5-dihydro-2-[4-(2-methylimidazo[4,5-c]pyrid-1-yl)phenyl]-5,7,9-trimethyl-1H-pyrido[2,3-b][1,4]diazepin-4-one; 8-bromo-3,5-dihydro-1 -methyl-2-[4-(2-methylimidazo[4,5-c]pyrid-1-yl)-phenyl]-4H-pyrido[2,3-b][1,4]diazepin-4-one; 1,3-dihydro-1,8-dimethyl-6-methoxycarbonyl-4-[4-(2-methylimidazo[4,5-c]pyrid-1-yl)-phenyl]-2H-thieno[3,4-b][1,4]diazepin-2-one; 5-[4-(2-methylimidazo[4,5-c]pyrid-1-yl)phenyl]-1,6,7,8-tetrahydro-1,3,8-trimethyl-pyrazolo[3,4-b][1,4]diazepin-7-one, 3-cyclohexyl-1,8-dimethyl-5-[4-(2-methylimidazo[4,5-c]pyrid-1-yl)phenyl]-1,6,7,8-tetrahydropyrazolo[3,4-b][1,4]diazepin-7-one, 8-bromo-5-[4-(2-methylimidazo[4,5-c]pyrid-1-yl)phenyl]-4H-imidazo[1,2-g]pyrido[2,3-b][1,4]diazepine, and 1,6,7,8-tetrahydro-1,8-dimethyl-5-[4-(2-methyl-1H-imidazo[4,5-c]pyrid-1-yl)phenyl]-7-oxo-3-(3-pyridyl)pyrazolo[3,4-b][1,4]diazepine.

It will be appreciated that for the compound of formula (I), when $R^2$ is H and the dashed line represents a bond as shown in formula (Ia), this formula may alternatively be written as formula (Ib), these forms of the compound being tautomeric. Similarly formula (IIa) may be written as formula (IIb) and formula (IIIa) may be written as (IIIb).

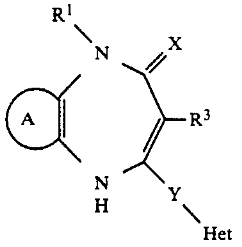
(Ia)

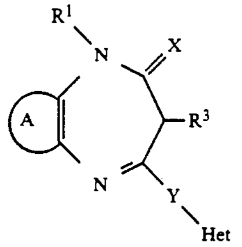
(Ib)

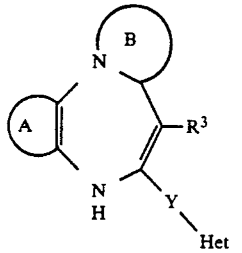
(IIa)

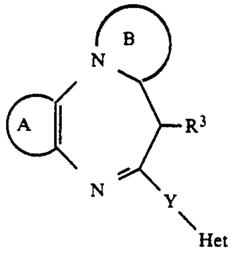
(IIb)

-continued

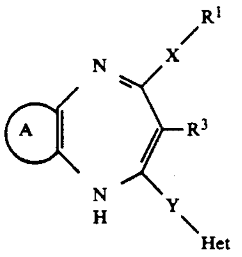

(IIIa)

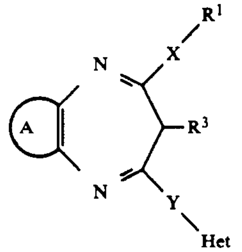

(IIIb)

Also, when $R^1$ is H, and X is =NH, the compound of formula (Ic) may be written as the alternative tautomeric form (Id):

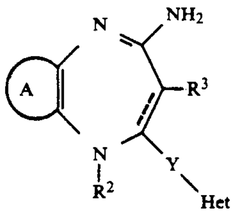

(Id)

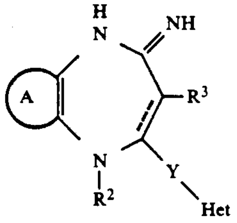

(Ic)

Such compounds and their salts may exist as one tautomer or a mixture of tautomeric forms, which may be separated by physical means such as fractional crystallisation or chromatography. The invention includes all the tautomers whether separated or not.

Compounds of formula (Ib), (IIb) and (IIIb) where $R^3$ is other than H and compounds of formula (I), (II) and (III) in which the dashed line is absent (i.e. a single bond in the ring between $R^3$ and Y instead of a double bond) are chiral and therefore exist as pairs of isomers which may be separated by conventional means. The invention includes all these enantiomers, whether separated or not.

The pharmaceutically acceptable acid addition salts of the compounds of formula (I), (II) and (III) are those formed from acids which form non-toxic addition salts, for example the hydrochloride, hydrobromide, sulphate or bisulphate, phosphate or acid phosphate, acetate, citrate, fumarate, gluconate, lactate, maleate, succinate, tartrate, methane-sulphonate and dimethanesulphonate, benzenesulphonate and p-toluenesulphonate. Particularly preferred salts are the dimethanesulfonates of 8-bromo-5-[4-(2-methyl imidazo[4,5-c]pynd-l-yl)phenyl]-4H-imidazo[1,2-g]pyndo[2,3-b][1,4]diazepine, 8,9-Dichloro-5-[4-(2-methyl-1H-imidazo[4,5-c]pyrid-1-yl)phenyl]-6H-imidazo[1,2-a][1,5]benzodiazepine, and the dimaleate salt of 1,6,7,8-tetrahydrodimethyl-5-[4-(2-methyl-1H-imidazo[4,5-c]pynd-1-yl)phenyl]-7-oxo-3-(3-pyridyl)pyrazola[3,4-b][1H]diazapine.

When the bond represented by the dashed line in formula (I) is present, X is O, $R^1$ is H or alkyl and $R^2$ and $R^3$=H the compounds of formula (I) may be prepared by the following synthesis:

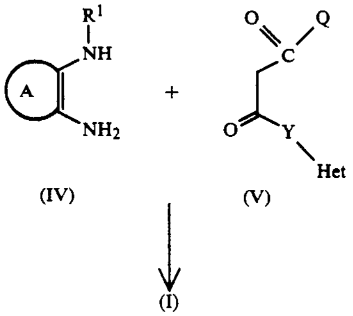

(IV) (V)

(I)

wherein A, Y and Het are as defined above and Q is a leaving group such as $C_1$–$C_4$ alkoxy. In a typical procedure the diamine(IV) and the compound (V) are heated under reflux in a suitable anhydrous solvent such as toluene under an inert atmosphere such as nitrogen for the period required to complete the reaction, typically 5 hours, and after cooling the mixture obtained is filtered and washed with the solvent to obtain the product of formula (I).

In the above synthesis, as diamine (IV) has two similar amino groups which react with corresponding carbonyl groups of compound (V) two regio-isomers of compound (I) are generally formed and these isomers are identical only when diamine (IV) is symmetrical about the bond of ring A connecting the amine bearing carbon atoms. The different isomers may generally be separated by chromatography.

Alternatively where A is a substituted pyrazolo ring the diamine (IV) and compound (V) are first heated under reflux in a suitable anhydrous solvent such as toluene, optionally in the presence of a dehydrating agent such as silica gel or in ethanol containing a catalytic quantity of zinc chloride for a suitable period, typically 20–24 hours and the solvent is then removed under vacuum. The residue is then dissolved in an alcoholic solvent such as ethanol containing an appropriate sodium alkoxide and stirred at room temperature to complete the reaction, the products being isolated and separated using conventional methods.

In this synthesis one of the amine groups of the substituted pyrazole (IV) is condensed with the keto group of compound (V) in the first step and in the second step ring closure takes place to form the diazepine as shown in the following scheme:

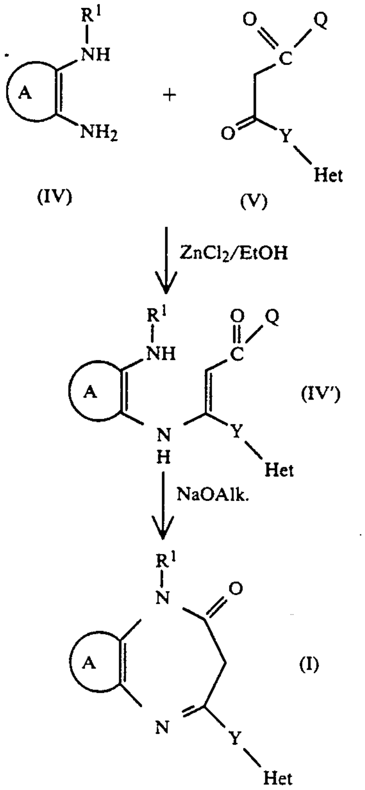

(IV) (V) (IV') (I)

If desired, the intermediate compound (IV') may be isolated and purified before the second step.

When ring A in the compound of formula (I) bears an amino group as a substituent the above synthesis may be carried out using the corresponding nitro-substituted diamine of formula (IV) and the nitro group in the compound (I) obtained may subsequently be reduced by conventional methods to yield the corresponding amine compound.

When ring A in the compound of formula (I) bears a carbamoyl group as a substituent, the compound may be prepared from the corresponding compound of formula (I) bearing a halo substituent, such as bromo, by reacting the halo compound with the appropriate amine in a carbon monoxide atmosphere in the presence of a catalyst such as tetrakistriphenylphosphine palladium to convert the halo group to a carbamoyl group.

When "Het" in formula (I) comprises a formyl derivative of a heterocyclic group, the above synthesis may be carried out using a compound (V) in which "Het" is the corresponding dioxolane derivative. The formyl derivative is obtained from the reaction of compound (IV) and the dioxolane compound (V) followed by hydrolysis of the crude product.

The compounds of formula (I) or (III) where X is O and $R^1$ is other than hydrogen may be obtained from the corresponding compound in which $R^1$ is H by treating the compound with the appropriate alkyl halide, phenyl-substituted alkyl halide, ester of a halo-substituted carboxylic acid, or halo-substituted amine or amide respectively. The halo compound used is suitably the bromide or iodide. In a typical procedure the compound of formula (I) or (III) in which $R^1$ is H is dispersed in a suspension of sodium hydride in a dry solvent such as dimethylformamide under nitrogen, followed by addition of the halo compound and continued stirring until completion of the reaction (typically 3 hours). The reaction mixture may then be treated with aqueous acid such as hydrochloric acid and the product separated by washing with an organic solvent, neutralisation of the organic layer for example with aqueous sodium carbonate, and extraction of the product with a solvent such as dichloromethane. The extract obtained may then be dried and concentrated and the desired compound purified by flash chromatography.

The compounds of formula (I) in which X is S may be prepared from the corresponding compounds in which X is O by treating the latter with phosphorus pentasulphide, typically by heating the oxo compound of formula (I) with $P_2S_5$ in a dry solvent such as pyridine in an inert atmosphere, pouring the cooled solution into water and isolating the desired thioamide by filtering off the solid product, drying the product by azeotropic distillation, dissolving the residue in dichloromethane and eluting the solution through silica gel.

The compounds of formula (II) may be prepared from the compounds of formula (Ib) in which $R^1$ and $R^3$ are H, and X is S and the dashed line represents a bond (formula Ie). In one procedure, the compound of formula (Ie) is first caused to react with hydrazine to produce an intermediate compound of formula (VI):

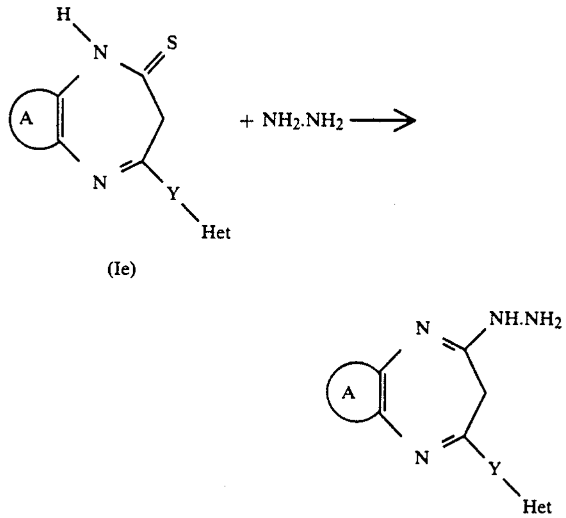

(Ie) (VI)

This reaction may be conducted by heating the thioamide of formula (Ie) with hydrazine hydrate and either an acid such as p-toluenesulphonic acid or red mercuric oxide in a suitable solvent such as n-butanol, and if necessary isolating the compound of formula (VI) by filtration and concentration of the filtrate under reduced pressure.

The compound (VI) may be converted to a compound (II) by various methods, according to the identity of substituent (B). When B is a fused tetrazole ring, compound (II) may be obtained by diazotising compound (VI), generally by treating it with sodium nitrite in aqueous hydrochloric acid at a low temperature followed by neutralisation of the solution, extraction of compound (II) in an organic solvent such as ethyl acetate/butanol, drying and concentration of the extract and purification by flash chromatography followed by recrystallisation:

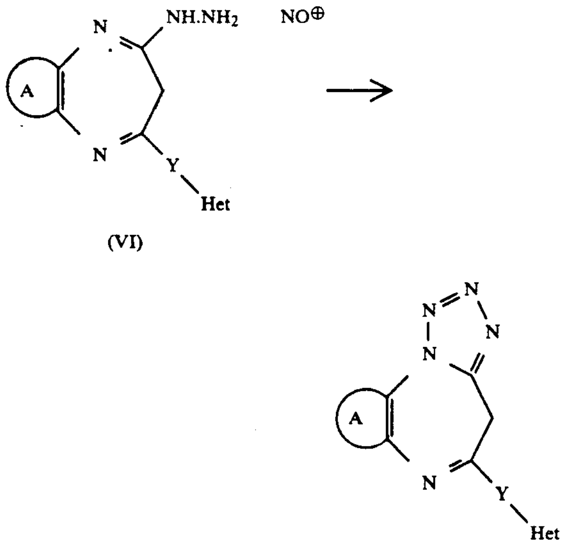

(VI)

When B is a fused 1,2,4 triazole ring which may be substituted by an alkyl or haloalkyl group, the compound (VI) may be treated with a trialkyl orthoformate and formic acid (to obtain the unsubstituted triazole) or the appropriate trialkylorthocarboxylate and the corresponding carboxylic acid (to obtain a substituted triazole):

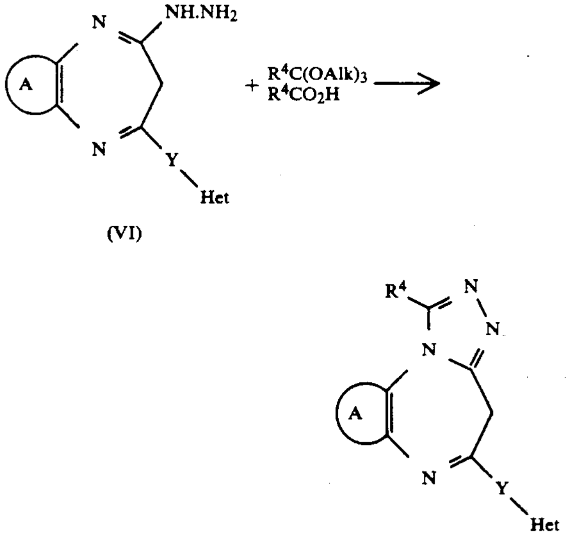

(VI)

wherein $R^4$ is H, $C_1$-$C_4$ alkyl or haloalkyl. In a typical procedure the reagents are refluxed together and the resulting mixture dissolved in an aqueous acid followed by extraction with an organic solvent such as ethyl acetate. The desired compound may be isolated from the extract by conventional methods.

When $R^4$ is a trifluoromethyl group, the hydrazino diazepine compound (VI) may be reacted with trifluoroacetic acid to produce the desired compound of formula (II).

When B is a fused 3-oxo-1,2,4 triazole ring, compound (II) may be prepared by treating a compound of formula (Ie) with an alkyl carbazate such as ethyl carbazate to produce an intermediate carbazate (VII):

(VII)

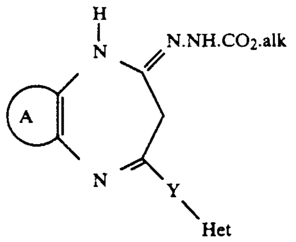

Compound (VII) may then be cyclised in the presence of sodium hydride to produce the desired compound of formula (IIc):

(IIc)

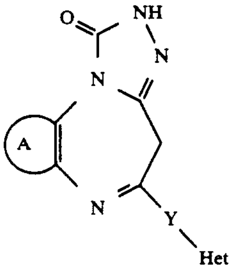

This preparation may be carried out by refluxing the compound (Ie) with ethyl carbazate in the presence of p-toluenesulphonic acid in a solvent such as n-butanol, removing the solvent under reduced pressure and purifying the residue by flash chromatography to yield the intermediate carbazate. This may then be dissolved in a dry solvent such as tetrahydrofuran followed by addition of sodium hydride and stirring at room temperature to cyclise the intermediate carbazate. The desired compound may then be extracted and purified by conventional methods.

When B is an unsubstituted imidazole ring, compound (II) may be prepared from the corresponding compound of formula (Ie) by reaction of the compound (Ie) with an acetal of aminoacetaldehyde such as aminoacetaldehyde dimethyl acetal in the presence of either p-toluene sulphonic acid or red mercuric oxide in a suitable solvent followed by ring closure, for example by treatment with concentrated sulphuric acid or formic acid:

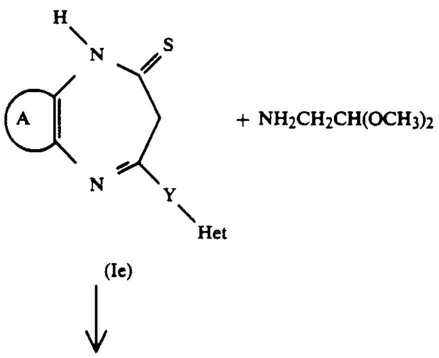

(Ie)

-continued

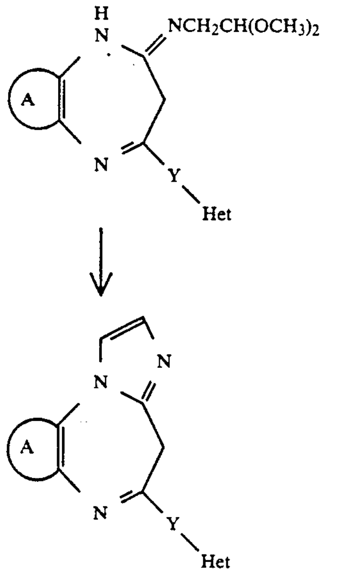

In one procedure compound (Ie) is refluxed with aminoacetaldehyde dimethyl acetal and either p-toluenesulphonic acid or red mercuric oxide in n-butanol in an inert atmosphere and the mixture is cooled, diluted with methanol and filtered if necessary, the solvent is removed under vacuum and if necessary the intermediate is purified by flash chromatography. The intermediate is then dissolved in concentrated sulphuric acid and heated at 100° C. The solution is then poured on to ice, neutralised and extracted with an organic solvent. The desired compound is recovered by concentration of the solvent and purification by flash chromatography. The concentrated sulphuric acid may be replaced by formic acid.

Certain compounds in which B is a substituted imidazole ring may be prepared in a similar manner using the appropriate homologue of the aminoacetaldehyde acetal, for example 2-amino-1, 1-diethoxypropane to produce a methyl substituted imidazole ring.

Other compounds (II) in which B is an imidazole ring substituted by a methyl group, may be prepared from compound (Ie) by treating the latter with propargylamine in the presence of red mercuric oxide.

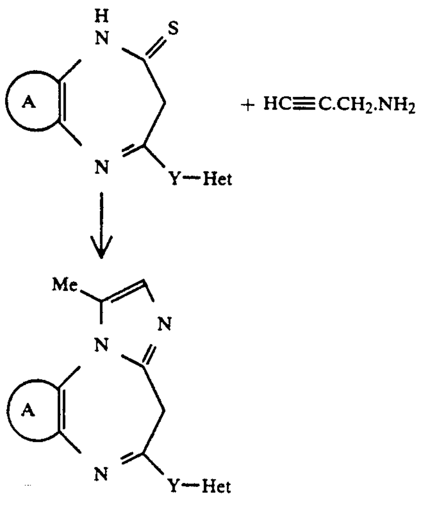

In one procedure compound (Ie) is refluxed with propargylamine and red mercuric oxide in n-butanol, the resulting mixture is diluted with methanol and filtered and concentrated to yield the crude compound which is purified by flash chromatography. Corresponding compounds in which the substituent on the imidazole ring is other than methyl may be prepared by using the appropriate homologue of propargylamine.

In a method of making compounds of formula (II) in which B is an imidazoline ring, a compound of formula (Ie) is reacted with ethanolamine to produce a compound of formula (VIII), which may then be cyclised to give the dihydro imidazo compound:

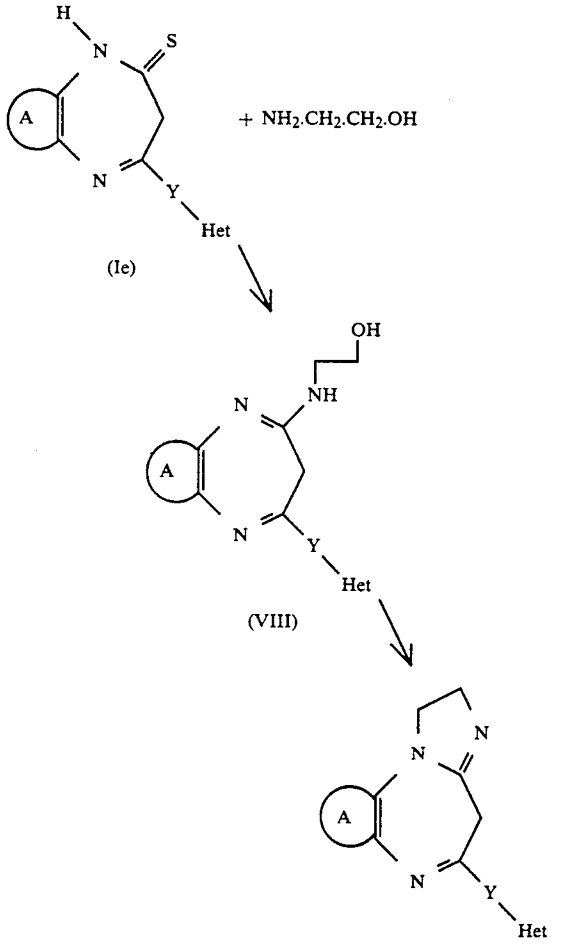

(Ie)

(VIII)

In one procedure compound (Ie) is refluxed with red mercuric oxide and ethanolamine in a suitable solvent to yield compound (VIII) which is then separated and treated with triphenylphosphine and diethylazodicarboxylate in a non-aqueous solvent to close the imidazoline ring. Substituted imidazoline rings may similarly be formed using an appropriately substituted ethanolamine.

The same method may be used for making compounds of formula (II) in which B is a substituted or unsubstituted tetrahydropyrimidine ring, using 3-amino-1-propanol or a substituted derivative thereof instead of ethanolamine.

When B is a pyrimidone ring compound (II) may be prepared by treating a compound of formula (Ie) with ammonia to form the corresponding 2-amino compound of formula (IX) and reacting the latter with methyl propiolate:

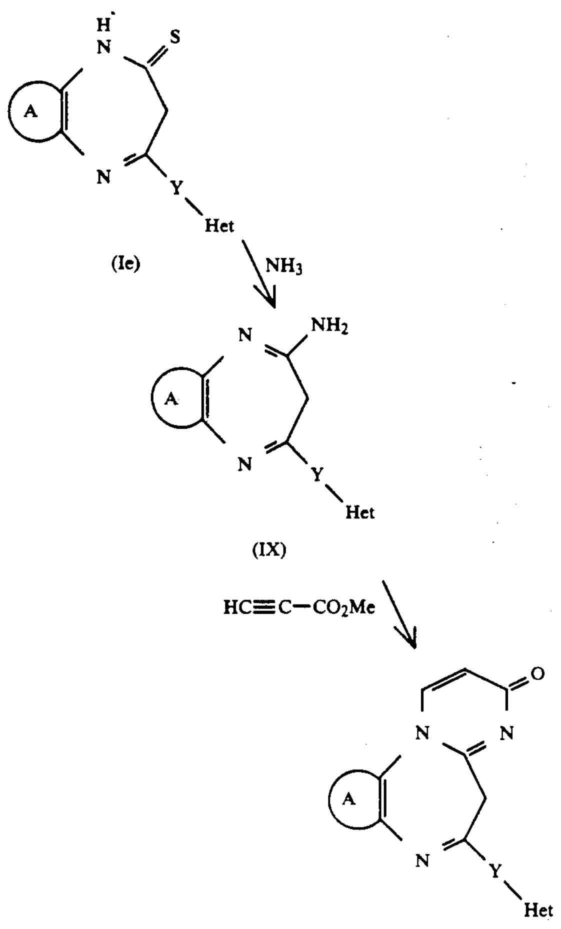

The compound of formula (I) may be heated with red mercuric oxide in a solvent saturated with ammonia, and the 2-amino compound formed isolated and refluxed with methyl propiolate to yield compound (II) which is then isolated by conventional methods.

The syntheses described above relate to compounds of formula (I), (II) or (III) in which the dashed line represents a bond. The corresponding compounds in which this bond is absent, that is compounds having a single instead of a double bond at this location, may be prepared by reduction of the compound having a double bond. This reduction may be performed, for example, by treating the double-bonded compound with sodium cyanoborohydride.

The above methods of preparation relate to compounds of formula (I), (II) or (III) in which $R^2=R^3=H$. These compounds may be converted to the corresponding compounds where $R^2$ or $R^3$ is a $C_1$–$C_4$ alkyl group by reaction with the appropriate alkyl halide in the presence of sodium hydride in a non-aqueous solvent. It will be appreciated that deprotonation of compounds of formula (I) or (II) where the dashed line represents a bond, $R^2=H$ and X is O will give an ambident anion, which may react on either the nitrogen and/or the carbon atom and/or the oxygen atom depending on the compound involved, the reaction conditions and the alkyl halide employed.

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2\times10^8$ platelets/ml. A sample (0.5 ml) is pre-incubated for two minutes at 37° C. in a Paton aggregometer with stirring, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I), (II) or (III) is also demonstrated in vivo by their ability to protect mice from the lethal effect of an injection of PAF. A mixture of PAF (50 μg/kg) and DL-propranolol (5 mg/kg) in 0.9% w/v sodium chloride is injected (0.2 ml) via a tail vein into mice. The compounds under test are either injected into the tail vein immediately prior to the PAF/propranolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recording of airflow and transpleural pressure and calculation of tidal volume. The bronchoconstriction induced by PAF (100 ng/kg) is determined. One hour after the initial dose of PAF the compound under test is administered and the test repeated. The ability of the compound to reduce the bronchoconstrictor effect of PAF is recorded as a ratio. For therapeutic use the compounds of the formula (I), (II) or (III) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For administration to man in the curative or prophylactic treatment of allergic bronchial conditions and arthritis, oral dosages of the compounds will generally be in the range of from 2-1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), (II) or (III) or a pharmaceutically acceptable salt thereof, together with a pharmaceutically acceptable diluent or carrier.

The invention also includes a compound of the formula (I), (II) or (III) or a pharmaceutically acceptable salt thereof, for use in medicine, in particular in the treatment of allergic and inflammatory conditions in a human being.

The preparation of the compounds of the invention is further illustrated by the following Examples.

EXAMPLE 1

2,3-Dihydro-4-[4-(2-methylimidazo[4,5-c]pyrid-1-yl)phenyl]-1H-[1,5]benzodiazepin-2-one

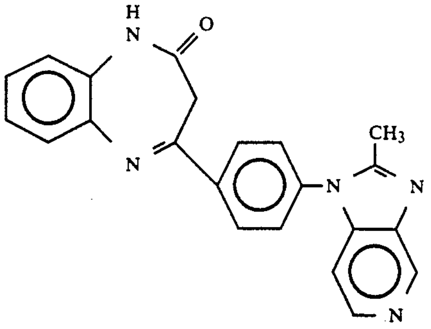

A mixture of 1,2-diaminobenzene (1.839 g, 17.03 mmol) and ethyl 4'-(2-methylimidazo[4,5-c]pyrid-1-yl)benzoylacetate (5.00 g, 15.48 mmol) in dry toluene (50 ml) was heated at reflux under nitrogen for 5 hours. The mixture was cooled and the product was filtered off and washed with toluene to give a buff solid, 4.097 g (72%). m.p 292° C.

Analysis %: Found: C,70.31; H,4.73; N,18.88; $C_{22}H_{17}N_5O.\frac{1}{2}H_2O$ requires: C,70.19; H,4.82; N,18.61.

The following examples (shown in Table 1) were prepared in a similar manner from the appropriate 1,2-diaminobenzene and 4-heterocyclic substituted benzoylacetic ester

TABLE 1

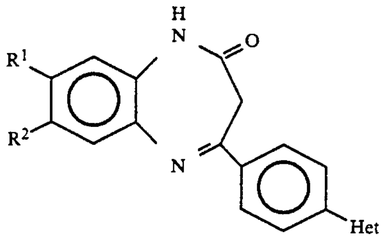

| Example | Het | $R^1$ | $R^2$ | m.p. | Analysis % (Theoretical in brackets) C | H | N |
|---|---|---|---|---|---|---|---|
| 2 | 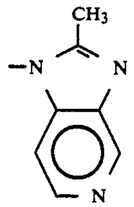 | $CH_3$ | $CH_3$ | 238-239° C. | 70.51<br>(70.44 | 5.56<br>5.82 | 16.56<br>16.56)* |
| 3 | 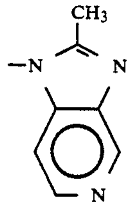 | Cl | Cl | 222-4° C. | 59.23<br>(59.10 | 3.59<br>3.94 | 15.38<br>15.20)# |

TABLE 1-continued
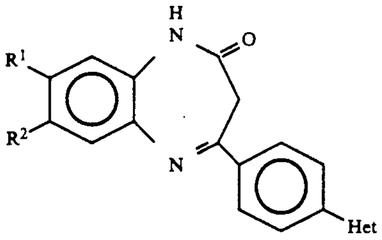
| Example | Het | R1 | R2 | m.p. | Analysis % (Theoretical in brackets) C | H | N |
|---|---|---|---|---|---|---|---|
| 4 | 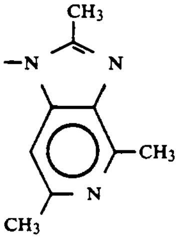 | $CH_3$ | $CH_3$ | 279–281° C. | 73.65<br>(73.73 | 5.89<br>5.95 | 16.31<br>16.54) |
| 5 | 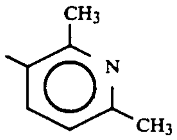 | $CH_3$ | $CH_3$ | 253–5° C. | 77.96<br>(78.02 | 6.11<br>6.27 | 11.14<br>11.37) |
| 6 | 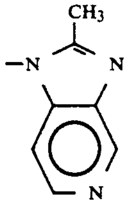 | [H<br>F<br>mixture obtained | F<br>H] | 234–236° C. | 68.81<br>(68.56 | 4.18<br>4.18 | 18.15<br>18.17) |
| 7 | 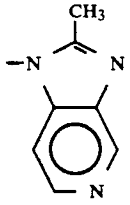 | H<br>Cl<br>mixture obtained | Cl<br>H | 203–205° C. | 64.47<br>(64.31 | 4.21<br>4.17 | 16.73<br>17.05) |
| 8 | 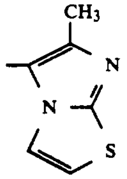 | $CH_3$ | $CH_3$ | 240–242° C. | 70.97<br>(71.27 | 5.33<br>5.42 | 12.52<br>12.55)[P] |
| 9 | 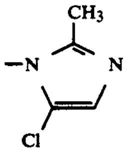 | $CH_3$ | $CH_3$ | 125–128° C. | 66.09<br>(66.49 | 4.96<br>5.03 | 14.61<br>14.76) |
| 10 | 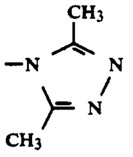 | Cl | Cl | 260–262° C. | 56.83<br>(56.51) | 3.89<br>4.01 | 16.73<br>17.04)** |

TABLE 1-continued

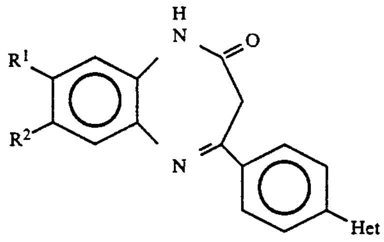

| Example | Het | $R^1$ | $R^2$ | m.p. | Analysis % (Theoretical in brackets) C | H | N |
|---|---|---|---|---|---|---|---|
| 11 | 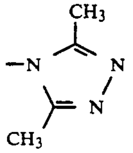 | $CH_3$ | $CH_3$ | 260–262° C. | 69.47<br>(69.30 | 6.00<br>5.95 | 19.58<br>19.24)*** |

#Calculated for 0.3 EtOH.0.5 $H_2O$ solvate.
Calculated for 0.5 $H_2O$ solvate.
[p]Calculated for 0.5 toluene.
*Calculated for 0.4 EtOH.0.5 $H_2O$ solvate.
**Calculated for 0.3 MeOH.
***Calculated for 0.25 $H_2O$.

EXAMPLE 12

2,3-Dihydro-4-[2-(2-methylimidazo[4,5-c]pyrid-1-yl)pyrid-5-yl]-1H-[1,5]benzodiazepin-2-one

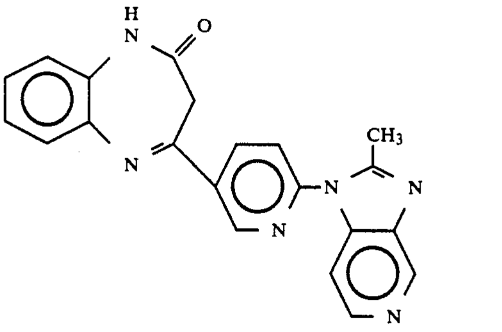

The procedure of Example 1 was followed using 1,2-diaminobenzene (86 mg, 0.76 mmol) and ethyl 2-(2-methylimidazo[4,5-c]pyrid-1-yl)pyrid-5-oylacetate (260 mg, 0.80 mmol). The crude product was purified by flash chromatography (eluting with ethyl acetate/methanol =6:1), followed by recrystallisation from acetone to give the title compound (40 mg, 14%) as a buff solid, m.p. 208°-210° C..

Analysis %: Found: C,66.90; H,4.45; N,21.62; $C_{21}H_{16}N_6O$. ½$H_2O$.0.16 $Me_2CO$ requires: C,66.70; H,4.68; N,21.71%.

EXAMPLE 13

2,3-Dihydro-4-[4-(2-methylimidazo[4,5-c]pyrid-1-yl)phenyl]-6-nitro-1H[1,5]benzodiazepin-2-one

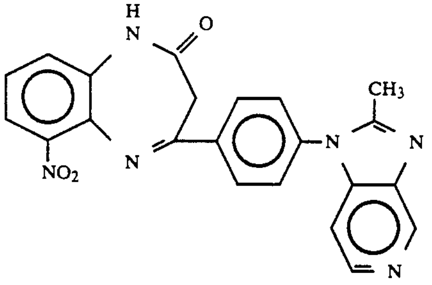

A mixture of 3-nitro-1,2-phenylenediamine (5 g, 33 mmol) and ethyl 4'-(2-methylimidazo[4,5-c]-pyrid-1-yl)benzoylacetate (9.7 g, 30 mmol) in 100 ml of toluene was heated at reflux for 16 hours. After cooling, the red/orange precipitate (12 g) was filtered and washed with ether.

This material was used directly without further purification in Example 14 below, m.p. 200° C. (broad).

$^1$H-NMR (300 MHz, DMSO-d6) 2.52 (3H, s), 4.30 (2H, s), 6.68 (1H, m), 7.27 (1H, d, J 5 Hz), 7.82 and 8.29 (each 2H, d, J 8 Hz), 8.33 (1H, d, J 5 Hz), 8.92 (1H, s) and 9.70 (1H, brs).

EXAMPLE 14

6-Amino-2,3-dihydro-4-[4-(2-methylimidazo[4,5-c]pyrid-1-yl)phenyl]-1H[1,5]benzodiazepin-2-one

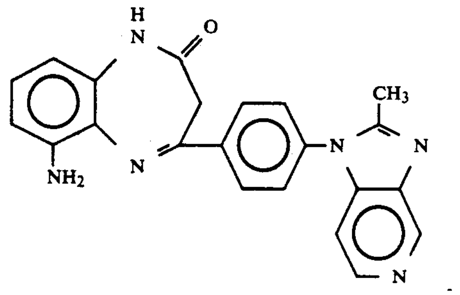

A solution of the product from Example 13 (10.3 g, 25 mmol), and stannous chloride dihydrate (28 g, 125 mmol) in 2M HCl (20 ml), ethanol (40 ml) and water (75 ml) was heated at reflux for 20 minutes, then stood at ambient temperature overnight (16 hours). Precipitated solids were filtered off, then the filtrate was adjusted to pH 6 by addition of saturated aqueous sodium bicarbonate and extracted with dichloromethane. The organic layer was dried (magnesium sulphate) and evaporated to a solid (3 g).

Two crude batches, obtained as described above, were chromatographed on silica gel, eluting using a gradient of 2–10% of diethylamine in ethyl acetate to afford the title compound as a yellow solid (3.7 g, 20%), m.p. 259°-263° C.

Analysis %: Found: C,67.63; H,4.86; N,21.56%. $C_{22}H_{18}N_6O.\frac{1}{2}H_2O$ requires: C,67.51; H,4.89; N,21.47%.

EXAMPLE 15

2,3-Dihydro-6-(1-ethoxyethylimino)-4-[4-(2-methylimidazo[4,5-c]pyrid-1-yl) phenyl]-1H-[1,5]benzodiazepin-2-one

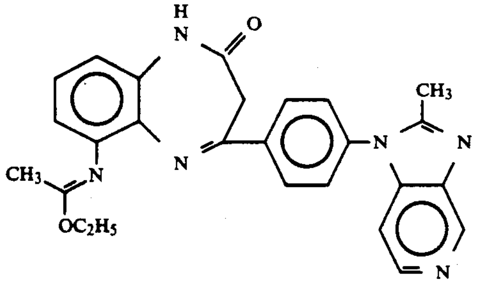

A solution of the aniline from Example 14 (0.38 g, 1 mmol) and glacial acetic acid (0.5 ml) in triethyl orthoacetate (5 ml) was stirred at 25° C. for 72 hours. The product was filtered and recrystallised from toluene (60 mg, 13%).

M.p. 214°-217° C.

Found: C,68.78; H,5.39; N,18.34%. $C_{26}H_{24}N_6O_2$ requires: C,69.01; H,5.35; N,18.57%.

EXAMPLE 16

2,3-Dihydro-6-ethyloxalamido-4-[4-(2-methylimidazo[4,5-c]pyrid-1-yl)phenyl]-1H-[1,5]benzodiazepin-2-one

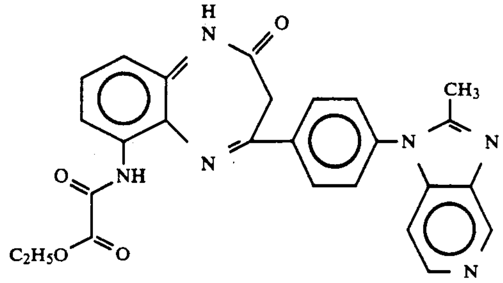

Oxalyl chloride (87 μl, 1 mmol) was added to a stirred suspension of the aniline (0.19 g, 0.5 mmol) from Example 14 in chloroform (2 ml containing 2% w/w ethanol). After 2 h, pyridine (0.3 g) was added and stirring was resumed for 1 h. The mixture was partitioned between chloroform and sodium bicarbonate solution. The organic layer was dried over magnesium sulphate and evaporated. The residue was purified by flash chromatography, (eluting with 5% methanol in chloroform) to afford a white solid (75 mg, 31%) .M.p. 269°-273° C.

Analysis %: Found: C,63.57 H,4.48 N,17.19%. $C_{26}H_{22}N_6O_4.\frac{1}{2}H_2O$ requires: C,63.53 H,4.72 N,17.10%.

EXAMPLE 17

2,3-Dihydro-6-ethanesulphonylamino-4-[4-(2-methylimidazo[4,5-c]pyrid-1-yl)-phenyl]-1H-[1,5]benzodiazepin-2-one

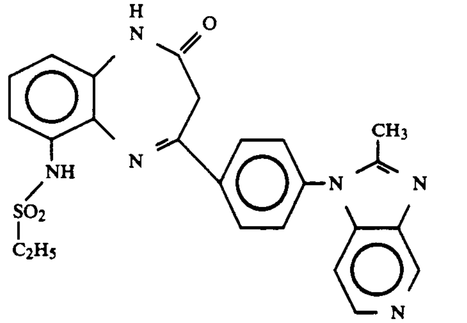

A suspension of the aniline from example 14 (0.5 g, 1.3 mmol) in dry pyridine (3 ml) was treated with ethanesulphonyl chloride (0.133 ml, 1.4 mmol). After 1 h, the mixture was evaporated to dryness then partitioned between dichloromethane and dilute aqueous sodium bicarbonate. The organic phase was dried over magnesium sulphate and evaporated to a yellow solid which was recrystallised from ethyl acetate (0.37 g, 59%). M.p. 258°-260° C.

Analysis %: Found: C,57.58 H,4.86 N,15.75 S,6.63%. $C_{24}H_{22}N_6O_3S.\ \frac{1}{2}CH_2Cl_2$ requires C,57.41 H,4.43 N,16.04 S,6.13%.

EXAMPLE 18

2,3-Dihydro-7,8-dimethyl-4-[4-(5-chloro-4-formyl-2-methylimidazol-1-yl)phenyl]-1H-[1,5]benzodiazepin-2-one

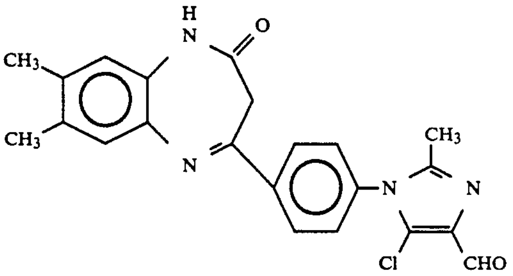

A solution of 4-[5-chloro-4-(1,3-dioxolan-2-yl)-2-methylimidazol-1-yl]benzoylacetate from Preparation 5 (155 mg, 0.38 mmol), and 4,5-dimethyl-1,2-diaminobenzene (55 mg, 0.4 mmol) in toluene (4 ml) was heated at reflux for 4.5 hours, then evaporated to dryness and purified by flash chromatography (eluting with ethyl acetate) to afford a pale yellow gum. 1M HCl (2 ml) was added to a solution of the residue in THF (2 ml) and the mixture was heated to 70° C. for 1 hour. The THF was evaporated and the residue was partitioned between aqueous sodium bicarbonate and dichloromethane. The organic layer was dried over magnesium sulphate and evaporated.

Flash chromatography (eluting with 2% methanol in ethyl acetate) afforded a pale-yellow solid (0.048 g, 31%).

$^1$H-NMR (300 MHz, $CDCl_3$) 2.34 (6H, br s), 2.40 (3H, s) 3.63 (2H,s), 6.90 (1H,s), 7.33 (1H,s), 7.41 (2H, d, J 8 Hz), 8.14 (1H br s), 8.33 (2H,d, J 8 Hz), 9.97 (1H,s),

EXAMPLE 19

2,3-Dihydro-7,8-dimethyl-4-[4-(2-methylimidazo[4,5-c]pyrid-1-yl)phenyl]-1H-[1,5]benzodiazepin-2-thione

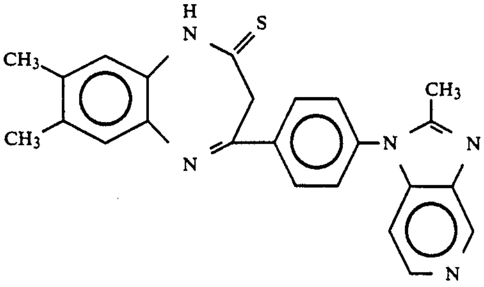

Phosphorus pentasulphide (2.31 g, 5.19 mmol) was added to a suspension of 2,3-dihydro-7,8-dimethyl-4-[4-(2-methylimidazo[4,5-c]pyrid-1-yl)phenyl]-1H-[1,5]benzodiazepin-2-one (Example 2) in dry pyridine (21 ml) under nitrogen. The mixture was heated under reflux for 45 minutes, then cooled and poured onto ice-water (200 ml). The solid material was filtered off, dried by azeotropic distillation with toluene, then dissolved in dichloromethane and adsorbed onto silica gel (200 mesh). This material was introduced onto a column of flash silica gel, and the product was recovered by eluting with dichloromethane:methanol=9:1. The solvent was removed under reduced pressure to give an orange solid (2.1 g, 73%), m.p. 233°-235° C.

$^1$H NMR (300 MHz, $CDCl_3$) 2.38 (6H, s), 2.64 (3H, s), 4.05 (2H, s), 7.00 (1H, s), 7.18 (1H, d, J 4 Hz), 7.38 (1H, s), 7.58 (2H, d, J 6 Hz), 8.50 (1H, d, J 4 Hz), 8.56 (2H, d, J 6 Hz), 9.14 (1H, s), 9.62 (1H, s).

The following Examples (shown in Table 2) were prepared in a similar manner from the corresponding benzodiazepinones (see Examples 1 to 11).

TABLE 2

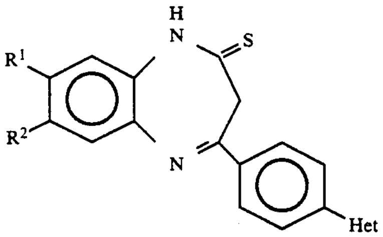

| Example | Het | R[1] | R[2] | m.p. | N.M.R. (300 MHz) (solvent) |
|---|---|---|---|---|---|
| 20 | 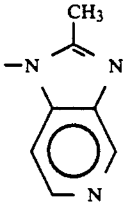 | H | H | 189-190° C. | (DMSO-$d_6$) 2.54 (3H, s), 4.00 (2H, br.s), 6.91 (1H, br.s), 7.28 (1H, d, J 6Hz), 7.34 (3H, m), 7.50 (1H, d, J 7Hz), 7.77 (2H, d, J 8Hz), 8.31 (1H, d, J 6 Hz), 8.46 (2H, d, J 8Hz), 8.93 (1H, s). |
| 21 | 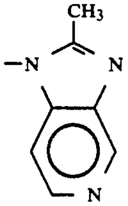 | Cl | Cl | 195-198° C. | ($CDCl_3$) 2.63 (3H, s), 4.12 (2H, s), 7.15 (1H, br.s), 7.17 (1H, d, J 4Hz), 7.40 (1H, s), 7.57 (2H, d, J 6Hz), 7.72 (1H, s), 8.43 (1H, d, J 4Hz), 8.55 (2H, d, J 6Hz), 9.10 (1H, s). |

TABLE 2-continued

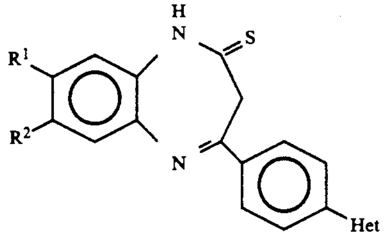

| Example | Het | R1 | R2 | m.p. | N.M.R. (300 MHz) (solvent) |
|---|---|---|---|---|---|
| 22 | 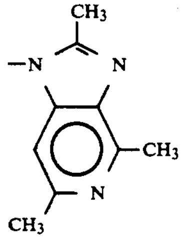 | $CH_3$ | $CH_3$ | 245–248° C. | ($CDCl_3$) 2.35 (6H, s), 2.57 (3H, s), 2.60 (3H, s), 2.93 (3H, s), 4.08 (2H, s), 6.86 (1H, s), 7.00 (1H, s), 7.34 (1H, s), 7.50 (2H, d, J 6Hz), 8.53 (2H, d, J 6Hz), 9.96 (1H, s). |
| 23 | 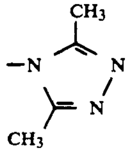 | Cl | Cl | 260–262° C. | (DMSO-$d_6$) 2.16 (6H,s), 4.08 (2H,br,s), 7.13 (1H,br,s), 7.58(1H,s) 7.65(2H,d J 8.5 Hz) 7.77 (1H,s) and 8.37 (2H,d,J 8.5Hz) |
| 24 | 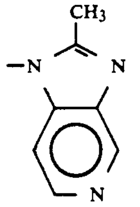 | [H / F] obtained as a mixture | [F / H] | 173–180° C. | |

EXAMPLE 25

2,3-Dihydro-1-methyl-4-[4-(2-methylimidazo[4,5-c]pyrid-1-yl)phenyl]-1H-[1,5]benzodiazepin-2-one

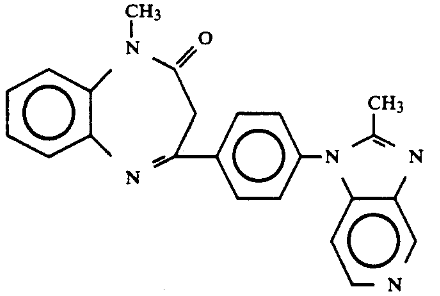

2,3-Dihydro-4-[4-(2-methylimidazo[4,5-c]pyridyl)-phenyl]-1H-[1,5]benzodiazepin-2-one (367 mg, 1.0 mmol) was added to a suspension of sodium hydride (60% dispersion in oil, 48 mg, 1.2 mmol) in dry tetrahydrofuran (3.5 ml) and the mixture was stirred at room temperature for 1 hour under nitrogen. Methyl iodide (142 mg, 1.0 mmol) was added and the mixture was stirred for a further 3 hours. The reaction mixture was treated with 2N hydrochloric acid (15 ml) and washed with toluene (15 ml). The organic layer was neutralised with saturated aqueous sodium bicarbonate and the product was extracted into dichloromethane (2×50 ml). The combined extracts were dried ($MgSO_4$), concentrated under reduced pressure, and the residue was purified by flash chromatography (eluting with ethyl acetate:methanol = 3:1) to give the title compound as an off-white solid, 107 mg (28%), m.p. 147° C.

Analysis %: Found: C,71.30; H,4.91; N,18.04; $C_{23}H_{19}N_5O.0.25\ H_2O$ requires: C,71.58; H,5.09; N,18.15%.

The compounds of Examples 26 and 27 given in Table 3 below were prepared in a similar manner using benzyl bromide and ethyl bromoacetate instead of methyl iodide.

TABLE 3

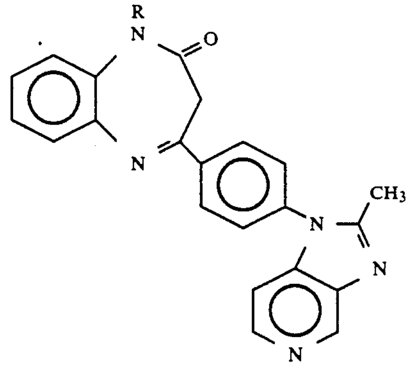

| Example | R | m.p. | Analysis % (Theoretical in brackets) C | H | N |
|---|---|---|---|---|---|
| 26 | $CH_2Ph$ | 125-128° C. | 75.40 | 5.01 | 14.99 |
| | | | (75.38 | 5.13 | 15.16)+ |
| 27 | $CH_2CO_2Et$ | 105-110° C. | 68.46 | 5.14 | 15.28 |
| | | | (68.86 | 5.11 | 15.44) |

+Calculated for 0.25 $H_2O$.

EXAMPLE 28

1,2-Dihydro-8,9-dimethyl-5-[4-(2-methylimidazo[4,5-c]pyrid-1-yl)phenyl]-6H-[1,2,4]triazolo[4,3-a][1,5]benzodiazepin-1-one

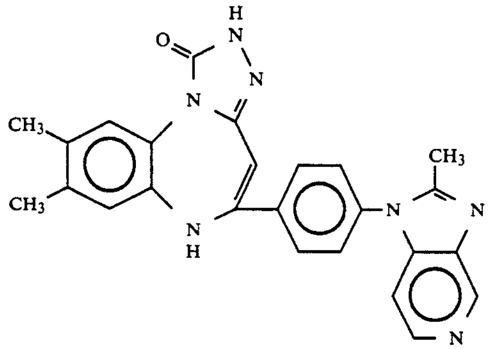

A solution of 2,3-dihydro-7,8-dimethyl-4-[4-(2-methylimidazo[4,5-c]pyrid-1-yl)phenyl]-1H-[1,5]benzodiazepin-2-thione (411 mg, 1.0 mmol), ethyl carbazate (210 mg, 2 mmol) and p-toluenesulphonic acid (10 mg) in n-butanol (5 ml) was stirred overnight at reflux. The solvent was removed under reduced pressure, and the residue was purified by flash chromatography (etuting with dichloromethane/methanol=9:1). The intermediate carbazate was then dissolved in dry tetrahydrofuran (5 ml) and cyclised by the addition of sodium hydride (60% dispersion in oil, 40 mg, 1 mmol) and stirring for 3 hours at room temperature. The mixture was partitioned between 2N hydrochloric acid (5 ml) and ethyl acetate (20 ml). The aqueous phase was neutralised with saturated aqueous sodium bicarbonate, and extracted with ethyl acetate:tetrahydrofuran=1:1 (2×30 ml). The extracts were combined, dried ($MgSO_4$), and concentrated under reduced pressure. The residue was purified by flash chromatography (eluting with dichloromethane:methanol=10:1). The product was further purified by recrystallisation from methanol/dichloromethane to give a white solid, (85 mg, 20%), m.p.>325° C.

Analysis %: Found: C,68.98; H,4.99; N,22.31; $C_{25}H_{21}N_7O$ requires: C,68.94; H,4.86; N,22.52%.

EXAMPLE 29

8,9-Dimethyl-5-[4-(2-methylimidazo[4,5-c]pyrid-1-yl)phenyl]-6H-[1,2,3,4]tetrazolo[1,5-a][1,5]benzodiazepine

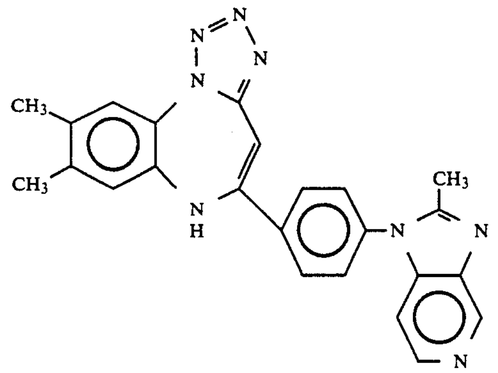

The corresponding hydrazinobenzodiazepine (from the corresponding benzodiazepinthione, 411 mg, as described in Preparation 6) was dissolved in 2N hydrochloric acid and cooled to −5° C. Aqueous sodium nitrite (72 mg in 11 ml water) was added over 2 minutes with stirring. The mixture was kept at −5° C. for a further 5 minutes, then was neutralised with 2N aqueous sodium hydroxide. The solution was extracted with ethyl acetate:butanol=2:1 (2×50 ml) and the combined extracts were dried ($MgSO_4$) and concentrated under reduced pressure. Purification by flash chromatography (eluting with dichloromethane:methanol=9:1), followed by recrystallisation from isopropanol gave the title compound as a brown solid (68 mg, 16%), m.p. 315° C.

Analysis %: Found: C,67.63; H,5.15; N,26.63; $C_{24}H_{20}N_8$.0.25 $H_2O$ requires: C,67.82; H,4.86; N,26.36%.

EXAMPLE 30

8,9-Dimethyl-5-[4-(2-methylimidazo[4,5-c]pyrid-1-yl)phenyl]-6H-[1,2,4]triazolo[4,3-a][1,5]benzodiazepine

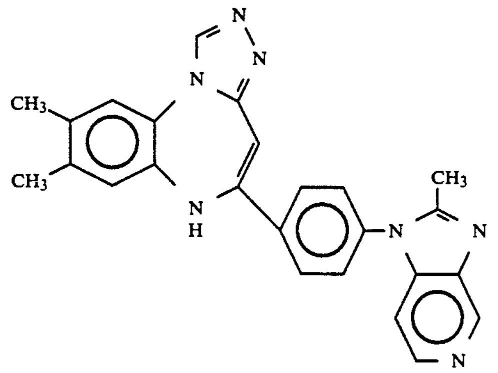

The corresponding hydrazinobenzodiazepine (from the corresponding benzodiazepinthione, 411 mg, as described in Preparation 6) was treated with triethylorthoformate (9 ml) and formic acid (2 ml) at reflux for 10 minutes. The reaction mixture was cooled, concentrated under reduced pressure, and dissolved in 1N hydrochloric acid (10 ml). This solution was washed with ethyl acetate (20 ml), neutralised with dilute aqueous ammonia, and extracted with ethyl acetate:tetrahydrofuran=1:1 (3×50 ml). The extracts were combined, dried ($MgSO_4$) and concentrated under reduced pressure. The residue was purifed by flash chromatography (eluting with ethyl acetate:methanol=9:1) to give a white solid (95 mg, 23%) m.p. 302°-304° C. (acetone).

Analysis %: Found: C,71.42; H,5.14; N,23.25; $C_{25}H_{21}N_7$ requires: C,71.58; H,5.05; N,23.37%.

EXAMPLE 31

5-[4-(2-Methylimidazo[4,5-c]pyrid-1-yl)phenyl]-1,8,9-trimethyl-6H-[1,2,4]triazolo[4,3-a][1,5]benzodiazepine

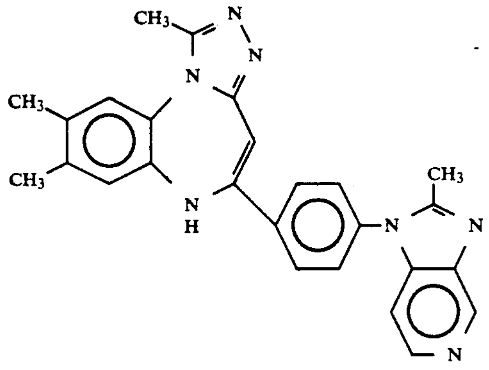

The method of Example 30 was repeated, substituting triethyl orthoacetate and acetic acid for triethylorthoformate and formic acid respectively. The product was purified by flash chromatography (eluting with dichloromethane:methanol=9:1), followed by sonication with ethyl acetate:ether=1:2 and drying in vacuo to give a brown solid (48 mg, 11%), m.p. 294°-296° C.

Analysis %: Found: C,70.95; H,5.45; N,22.39; $C_{26}H_{23}N_7.\frac{1}{2}H_2O$ requires: C,70.56; H,5.46; N,22.16%.

EXAMPLE 32

8,9-Dichloro-5-[4-(2-methylimidazo[4,5-c]pyrid-1-yl)phenyl-1-trifluoromethyl-6H-[1,2,4]triazolo[4,3-a][1,5]benzodiazepine

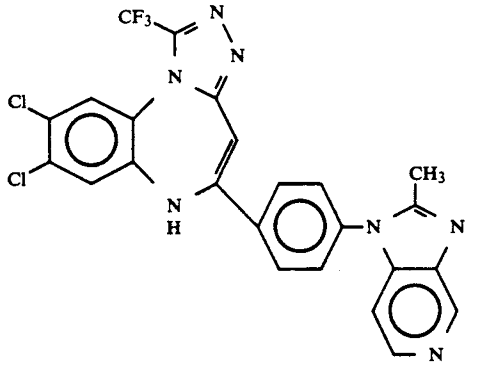

A solution of 7,8-dichloro-2-hydrazino-4-[4-(2-methylimidazo[4,5-c]pyrid-1-yl)phenyl]-3H-[1,5]benzodiazepine (from the corresponding benzodiazepinthione 452 mg, as described in Preparation 7) in trifluoroacetic acid (3 ml) was heated under nitrogen at reflux for 30 minutes, cooled, and poured onto ice. The solution was rendered basic by the addition of 2N aqueous sodium hydroxide, and the mixture was extracted with ethyl acetate:n-butanol=4:1 (total of 200 ml). The extracts were washed with saturated aqueous sodium chloride (30 ml), dried ($MgSO_4$) and concentrated under reduced pressure. The residue was purified by flash chromatography (eluting with ethyl acetate:methanol=5:1) to give a buff solid, which was triturated with ethyl acetate, and dried in vacuo to give the title compound (60 mg, 11%), m.p. 145°-150° C.

$^1$H-NMR ($CDCl_3$) 2.55 (3H, s), 6.19 (1H, s), 6.41 (1H, br.s), 6.84 (1H, s), 7.10 (1H, d, J 6Hz), 7.38 (2H, d, J 8Hz), 7.50 (1H, s), 7.91 (2H, d, J 8Hz), 8.35 (1H, d, J 6Hz), 9.00 (1H, s).

EXAMPLE 33

8,9-Dimethyl-5-[4-(2-methylimidazo[4,5-c]pyrid-1-yl)phenyl]-6H-imidazo[1,2-a][1,5]benzodiazepine

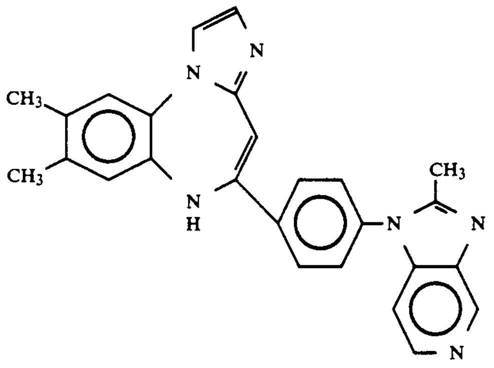

A mixture of 2,3-dihydro-7,8-dimethyl-4-[4-(2-methylimidazo[4,5-c]pyrid-1-yl)phenyl]-1H-[1,5]benzodiazepin-2-thione (575 mg. 1.4 mmol), aminoacetaldehyde dimethyl acetal (294 mg, 2.8 mmol), and p-toluenesulphonic acid (14 mg) in n-butanol (7 ml) was heated at reflux for 8 hours under nitrogen. The solvent was removed under reduced pressure, and the residue was purified by flash chromatography (eluting with ethyl acetate/methanol=6:1). The intermediate thus obtained was dissolved in concentrated sulphuric acid (5 ml) and heated at 100° C. for 20 minutes. The mixture was cooled and poured onto ice, and then neutralised with saturated aqueous sodium bicarbonate. The product was extracted into dichloromethane (2×150 ml), and the combined extracts were dried ($MgSO_4$) and concentrated under reduced pressure. Purification by flash chromatography (eluting with ethyl acetate:methanol=6:1) gave the title compound as a buff solid, (180 mg, 31%), m.p. 193°-195° C. after dissolution in methanol and precipitation with acetone.

Analysis %: Found: C,70.70; H,5.80; N,16.62; $C_{26}H_{22}N_6.H_2O$.acetone requires: C,70.41; H,6.11; N,16.99.

EXAMPLE 34

(a)

7,8-Dichloro-2-(2,2-dimethoxyethylamino)-4-[4-(2-methylimidazo[4,5-c]pyrid-1-yl)phenyl]-3H[1,5]benzodiazepine

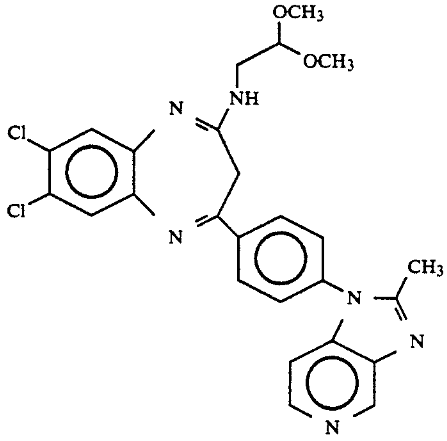

A mixture 7,8-dichloro-2,3-dihydro-4-[4-(2-methylimidazo[4,5-c]pyrid-1-yl)phenyl]-1H-[1,5]benzodiazepin-2-thione (1.36 g, 3.0 mmol), aminoacetaldehyde dimethyl acetal (630 mg, 6.0 mmol) and red mercuric oxide (650 mg, 3.0 mmol) in n-butanol (15 ml) was heated at reflux for 2.5 hours. The mixture was cooled, diluted with methanol (50 ml) and filtered through Hyflo filter aid. The solvents were removed under reduced pressure to give a foam, which was suspended in pentane and sonicated for 5 minutes. The pentane was removed in vacuo to give the title compound, 1.10 g (70%).

$^1$H NMR (300 MHz, $CDCl_3$), 2.61(3H,s), 3.36(2H, br s), 3.42(6H,s), 3.60(2H,t,J=5Hz), 4.53(1H,t,J=5Hz), 5.38(1H,t,J=5Hz), 7.15(1H,d,J=5Hz), 7.46(1H,s), 7.51(2H,d,J=8Hz), 7.64(1H,s), 8.23(2H,d,J=8Hz), 8.42(1H,d,J=5Hz), 9.13(1H,s).

(b)

8,9-Dichloro-5-[4-(2-methylimidazo[4,5-c]pyrid-1-yl)phenyl]-6H-imidazo[4,5-c][1,5]benzodiazepine

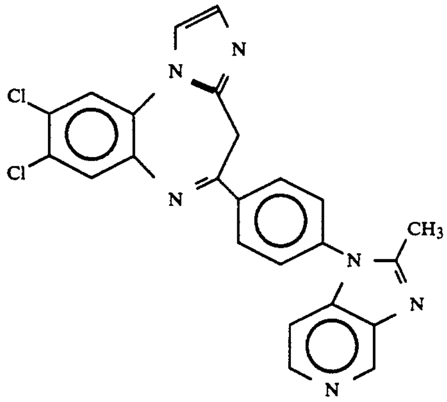

7,8-Dichloro-2-(2,2-dimethoxyethylamino)-4-[4-(2-methylimidazo[4,5-c]pyrid-1-yl)phenyl-3H-[1,5]benzodiazepine (1.10 g, 2.10 mmol) was dissolved in concentrated sulphuric acid (10 ml), and the mixture was heated at 100° C. for 30 minutes, cooled and poured onto ice. The solution was neutralised with 4N aqueous sodium hydroxide and extracted with dichloromethane (3×100 ml). The extracts were combined, dried ($MgSO_4$) and concentrated. The residue was purified by flash chromatography (eluting with ethyl acetate/methanol=3:1). The product was further purified by being dissolved in 100 ml of boiling methanol, filtering the solution, concentrating to 10 ml, and filtering off the product and drying in vacuo. The title compound was obtained as a buff solid (340 mg, 25%), m.p. 241°-243° C.

Analysis%: Found: C,61.58; H,3.56; N,18.07. $C_{24}H_{16}Cl_2N_6 \cdot \frac{1}{2}H_2O$ requires C,61.54; H,3.66; N,17.95. The above procedure was repeated using an equivalent amount of formic acid instead of sulphuric acid. An identical product was obtained in 50% yield.

The following Examples shown in Table 4, were prepared by the method of Example 34 using the appropriate thioamide.

TABLE 4

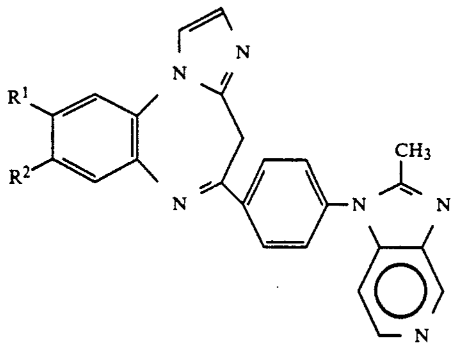

| Example | $R^1$ | $R^2$ | m.p. °C. | Analysis % (Theoretical in brackets) C | H | N |
|---|---|---|---|---|---|---|
| 35 | H | H | 193-5 | 71.44 | 4.48 | 20.78 |
| | | | | (71.61 | 4.84 | 20.88)* |
| 36 | F | H | 203-7 | 69.68 | 4.13 | 19.97 |
| | H | F | | (69.55 | 4.30 | 20.28)# |
| | mixture obtained | | | | | |

*calculated for $\frac{2}{3}$ $H_2O$
#calculated for $\frac{1}{3}$ $H_2O$

EXAMPLE 37

8,9-Dimethyl-5-[4-(2,4,6-trimethylimidazo[4,5-c]pyrid-1-yl)phenyl]-4H-imidazo[1,2-a][1,5]benzodiazepine

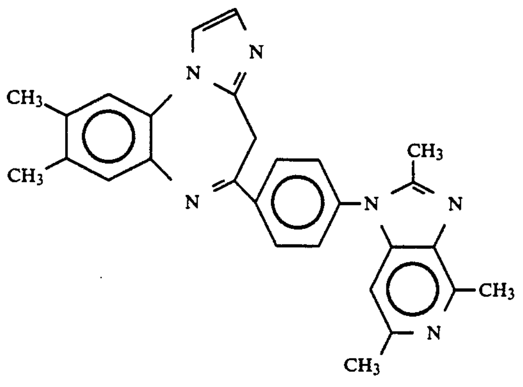

The procedure of Example 34 was followed using the corresponding thioamide from Example 22 to obtain the title compound (yield 14%).

$^1$H-NMR (300 MHz, $CDCl_3$). 2.40 (6H, s), 2.56 (3H, s), 2.60 (3H, s), 2.91 (3H, s), 4.05 (2H, brs), 6.80 (1H, s), 7.15 (1H, s), 7.36 (1H, s), 7.40 (2H, s), 7.45 (2H, d, J 8Hz), 8.34 (2H, d, J 8Hz).

EXAMPLE 38

8,9-Dichloro-1-methyl-5-[4-(2-methylimidazo[4,5-c]pyrid-1-yl)phenyl]-4H-imidazo[1,2-a][1,5]benzodiazepine

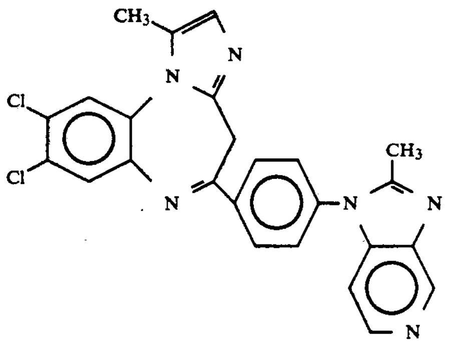

A mixture of 7,8-dichloro-2,3-dihydro-4-[4-(2-methylimidazo[4,5-c]pyrid-1-yl)phenyl]-1H-[1,5]benzodiazepin-2-thione (452 mg, 1.0 mmol), propargylamine (110 mg, 2.0 mmol) and red mercuric oxide (216 mg, 1.0 mmol) in n-butanol (5 ml) was heated at reflux for 10 hours. The mixture was cooled, diluted with methanol (50 ml) and filtered through Arbocel filter aid. The filtrate was concentrated under reduced pressure, and purified by flash chromatography (eluting with ethyl acetate:methanol=3:1). The product was further purified by trituration with ether to give the title compound as a buff solid, (170 mg, 38%), m.p. 243°-246° C.

Analysis %: Found: C,61.10; H,3.66; N,16.99; $C_{25}H_{18}Cl_2N_6.H_2O$ requires: C,61.11; H,4.10; N,17.10%.

EXAMPLE 39

8,9-Dichloro-1-methyl-5-[4-(3,5-dimethyl-1,2,4-triazol-4-yl)phenyl]-4H-imidazo[1,2-a][1,5]benzodiazepine.

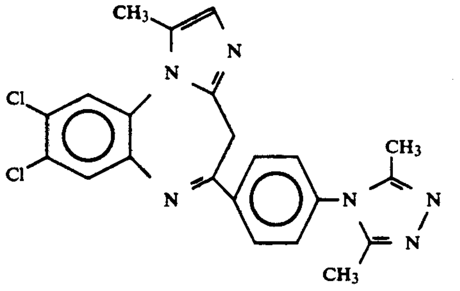

The procedure of Example 38 was followed using the corresponding thioamide from Table 2 to obtain the title compound (yield 12%),mp 165° C.

$^1$H-NMR (250 MHz, $CDCl_3$) 2.27(6H,s), 2.36(3H,s), 3.22(1H,d,J 15 Hz), 4.70(1H,d,J 15 Hz), 6.90(1H,d,J 1 Hz), 7.33(2H,d,J 8 Hz), 7.57(1H,s), 7.72(1H,s), 8.30(2H,d,J 8 Hz).

EXAMPLE 40

By the method of Example 38 the thioamide from Example 20 (383 mg, 1.0 mmol) was converted into 1-methyl-5-[4-(2-methylimidazo[4,5-c]pyrid-1-yl)phenyl]-4H-imidazo[1,2-a][1,5]benzodiazepine (110 mg, 27%), m.p. 213°-215° C.

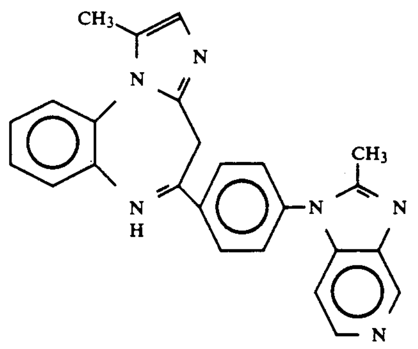

Analysis %: Found: C,72.02; H,5.07; N,20.13. $C_{25}H_{20}N_6.\frac{2}{3}\ H_2O$ requires: C,72.09; H,5.16; N,20.18.

EXAMPLE 41

8,9-Dichloro-2-methyl-5-[4-(2-methylimidazo[4,5-c]pyrid-1-yl)phenyl]-4H-imidazo[1,2-a][1,5]benzodiazepine

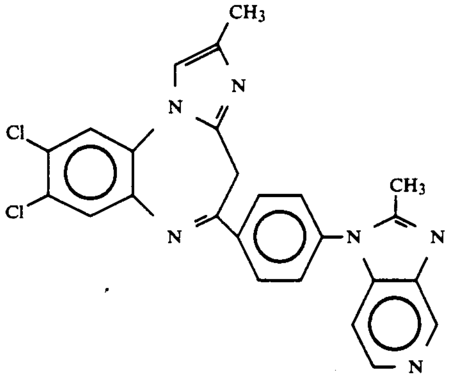

The procedure of Example 34 was followed using 2-amino-1,1-diethoxypropane instead of aminoacetaldehyde diethyl acetal, and formic acid at reflux instead of concentrated sulphuric acid. The crude product was purified by flash chromatography, eluting with ethyl acetate:methanol=6:1. The product was further purified by precipitation from hot ethyl acetate by the addition of pentane. The resulting yellow solid (16% yield), was found to exist as a mixture of imine and enamine tautomers (ratio 85:15).

Analysis %: Found: C,60.83; H,3.90; N,16.59. $C_{25}H_{18}Cl_2N_6.H_2O$ requires: C,61.10; H,4.10; N,17.10.

$^1$H NMR (300 MHz, $CDCl_3$) (imine tautomer only) 2.32 (3H, s), 2.62 (3H, s), 4.03 (2H, br.s), 7.13 (2H, br.s), 7.53 (2H, d, J 8Hz), 7.67 (1H, s), 7.75 (1H, s), 8.37 (2H, d, J 8Hz), 8.57 (1H, d, J 5Hz), 9.10 (1H, s).

EXAMPLE 42

8,9-Dichloro-1,2-dihydro-5-[4-(2-methylimidazo[4,5-c]pyrid-1-yl)phenyl]-4H-imidazo[1,2-a][1,5]benzodiazepine

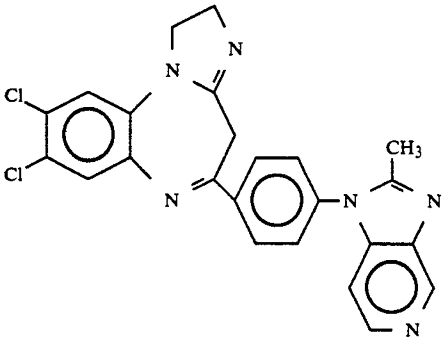

(a) A mixture of 7,8-dichloro-2,3-dihydro-4-[4-(2-methylimidazo[4,5-c]pyrid-1-yl)phenyl]-1H-[1,5]benzodiazepin-2-thione (453 mg, 1.0 mmol), ethanolamine (122 mg, 2.0 mmol) and red mercuric oxide (216 mg, 1.0 mmol) was heated in n-butanol (5 ml) at reflux for 1 hour. The mixture was cooled, diluted with an equal volume of toluene and filtered through Arbocel filter aid. The filtrate was concentrated under reduced pressure, and the residue was purified by flash chromatography, eluting with ethyl acetate:methanol=4:1. Fractions containing product were evaporated yielding 7,8-dichloro-2-[2-hydroxyethylamino]-4-[4-(2-methylimidazo[4,5-c]pyrid-1-yl)phenyl]-3H-[1,5]-benzodiazepine as a yellow foam, (345 mg, 72%).

$^1$H-NMR (300 MHz, $CDCl_3$) 2.60 (3H, s), 3.40 (2H, br s), 3.60 (2H, br s), 3.88 (2H, m), 6.38 (1H, br s), 7.14 (1H, d, J 4Hz), 7.38 (2H, d, J 6Hz), 7.46 (1H, s), 7.60 (1H, s), 8.18 (2H, d, J 6Hz), 8.35 (1H, d, J 4Hz), 9.17 (1H, s).

(b) The product from (a), above, (340 mg) and triphenylphosphine (242 mg, 0.92 mmol) were dissolved in dry tetrahydrofuran at room temperature. Diethyl azodicarboxylate (160 mg, 0.92 mmol) was added, and the mixture was stirred for 20 minutes. The solvent was removed under reduced pressure and the residue was purified by flash chromatography eluting with ethyl acetate:methanol:diethylamine=85:15:1. The product was further purified by precipitation from solution in hot ethyl acetate by the addition of pentane. The product was obtained as a yellow solid (95 mg, 29%), m.p. 159°-162° C.

Analysis %: Found: C,60.94; H,3.93; N,17.52; $C_{24}H_{18}Cl_2N_6.\frac{1}{2}$ $H_2O$ requires: C,61.28; H,4.07; N,17.87.

EXAMPLE 43

9,10-Dichloro-6-[4-(2-methylimidazo[4,5-c]pyrid-1-yl)phenyl]-1,2,3,5-tetrahydro-5H-pyrimido[1,2-a][1,5]benzodiazepine

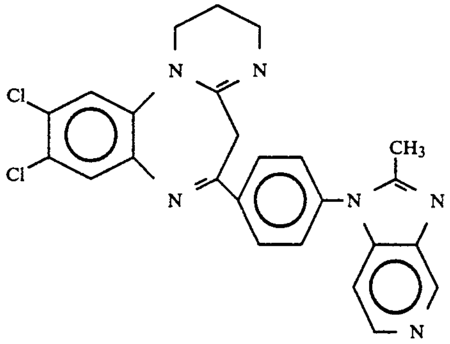

(a) By the method of Example 42(a) using 3-amino-1-propanol instead of ethanolamine was prepared 7,8-dichloro-2-(3-hydroxypropylamino)-4-[4-(2-methylimidazo[4,5-c]pyrid-1-yl)phenyl]-3H-[1,5]benzodiazepine, as a yellow solid.

$^1$H-NMR (300 MHz, $CDCl_3$) 1.80 (2H, m), 2.58 (3H, s), 3.42 (2H, br s), 3.60 (2H, m), 3.77 (2H, t, J 3Hz), 5.05 (1H, br s), 6.63 (1H, t, J 5 Hz), 7.12 (1H, d, J 4Hz), 7.34 (2H, d, J 6Hz), 7.46 (1H, s), 7.80 (1H, s), 8.18 (2H, d, J 6Hz), 8.32 (1H, d, J 4Hz), 9.07 (1H, s).

(b) The product from (a) was converted to the title compound as described in Example 42(b), yielding a creamy-coloured solid (62%), m.p. 157°-158° C.

Analysis %: Found: C,62.05; H,4.06; N,17.41; $C_{25}H_{20}Cl_2N_6.\frac{1}{2}$ $H_2O$ requires: C,61.98; H,4.37; N,17.35%.

EXAMPLE 44

2-Amino-7,8-dimethyl-4-[4(2-methylimidazo[4,5-c]pyrid-1-yl)-phenyl]-3H-[1,5]benzodiazepine

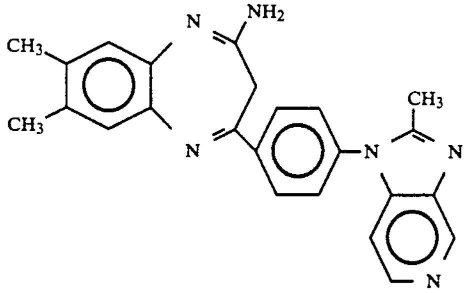

A mixture of the thioamide (from Example 19) (2.98 g, 7.24 mmol) and red mercuric oxide (1.57 g, 7.24 mmol) in n-butanol (40 ml) was saturated with ammonia gas at room temperature, and then stirred at 120° C. for 3 hours. After being cooled, the mixture was diluted with methanol (150 ml) and filtered through Arbocel filter aid. The filtrate was concentrated under reduced pressure, and the residue was purified by flash chromatography (eluting with ethyl acetate:methanol:diethylamine=100:10:5). Fractions containing the product were evaporated to give the title compound as a bright yellow solid (1.085 g, 38%), m.p. 299°-302° C.

Analysis %: Found: C,72.25; H,5.65; N,20.88; $C_{24}H_{22}N_6.\frac{1}{3}$ $H_2O$ requires: C,71.98; H,5.71; N,20.99%.

EXAMPLE 45

2-Amino-4-[4-(2-methylimidazo[4,5-c]pyrid-1-yl)phenyl]-3H-[1,5]benzodiazepine

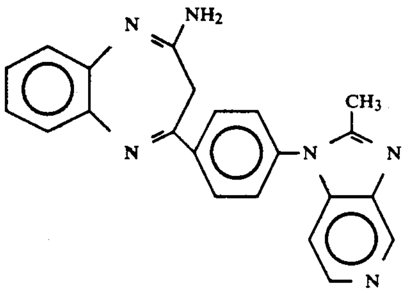

The title compound was prepared using the method described in Example 44 with the thioamide of Example 20 replacing the thioamide of Example 19. The product was obtained as a yellow solid (21% yield), m.p. 201°-203° C.

$^1$H NMR (300 MHz, $CDCl_3$), 1.70 (2H, br s), 2.62 (3H, s), 3.42 (2H, br s), 7.16 (1H, d, J 5Hz), 7.29 (3H, m), 7.52 (2H, d, J 8 Hz), 7.55 (1H, d, J 8Hz), 8.29 (2H, d, J 8Hz), 8.43 (1H, d, J 5 Hz), 9.10 (1H, s).

EXAMPLE 46

9,10-Dimethyl-6-[4-(2-methylimidazo[4,5-c]pyrid-1-yl)phenyl]-5H-pyrimido[1,2-a][1,5]benzodiazepin-3-one

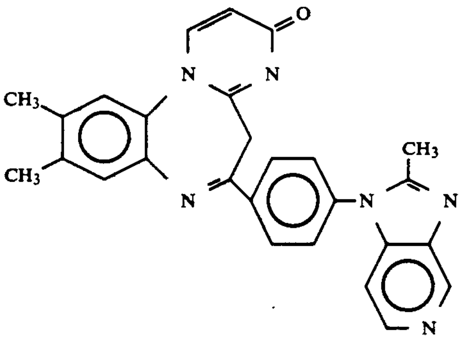

A solution of 2-amino-7,8-dimethyl-4-[4-(2-methylimidazo-[4,5-c]pyrid-1-yl)phenyl]-3H-[1,5]benzodiazepine (Example 44) (395 mg, 1.0 mmol) and methyl propiolate (168 mg, 2.0 mmol) in n-butanol (4 ml) was heated at reflux for 16 hours under nitrogen. The solvent was removed under reduced pressure and the residue was purified by flash chromatography (eluting with ethyl acetate:methanol: diethylamine=100:10:5). Fractions containing product were concentrated, and the residue was treated with dichloromethane, leaving some insoluble tarry material. The dichloromethane solution was decanted, concentrated, and the resulting brown solid triturated with hexane to give the title compound (46 mg, 10%), m.p. 192°-194° C.

Analysis %: Found: C,71.01; H,5.41; N,17.13; $C_{27}H_{22}N_6O.\frac{1}{4}$.hexane $\frac{3}{4}$ $H_2O$ requires: C,71.08; H,5.65; N,17.45.

EXAMPLE 47

4,5-Dihydro-8,9-dimethyl-5-[4-(2-methylimidazo[4,5-c]pyrid-1-yl)phenyl]-6H-imidazo[1,2-a][1,5]benzodiazepine

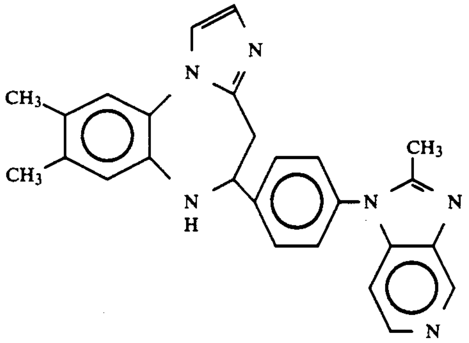

A solution of 8,9-dimethyl-5-[4-(2-methylimidazo[4,5-c]pyrid-1-yl)phenyl]-4H-imidazo[1,2-a][1,5]-benzodiazepine (100 mg, 0.24 mmol) in dichloromethane was stirred with an excess of ethereal hydrogen chloride until precipitation was complete. The solid was filtered and dissolved in dry methanol (5 ml) to which was added sodium cyanoborohydride (20 mg 0.32 mmol). After stirring for 16 hours, the solution was acidified with dilute hydrochloric acid then adjusted to pH 8 by addition of sodium bicarbonate solution. The mixture was extracted with ethyl acetate which was dried over magnesium sulphate. Evaporation left a colourless gum.

The residue was purified by flash chromatography (eluting ethyl acetate-methanol=3:1) to give a white solid (30 mg, 30%), m.p. 223°-227° C.

Analysis %: Found C, 71.12; H, 5.87; N,18.80% $C_{26}H_{24}N_6,H_2O$ Requires C, 71.21; H, 5.98; N,19.16%

EXAMPLE 48

1,3-Dihydro-7,9-dimethyl-4-[4-(2-methylimidazo[4,5-c]pyrid-1-yl)-phenyl]-2H-pyrido[2,3-b][1,4]diazepin-2-one (Compound A)

3,5-Dihydro-7,9-dimethyl-2-[4-(2-methylimidazo[4,5-c]pyrid-1-yl)-phenyl]-4H-pyrido[2,3-b][1,4]diazepin-4-one (Compound B)

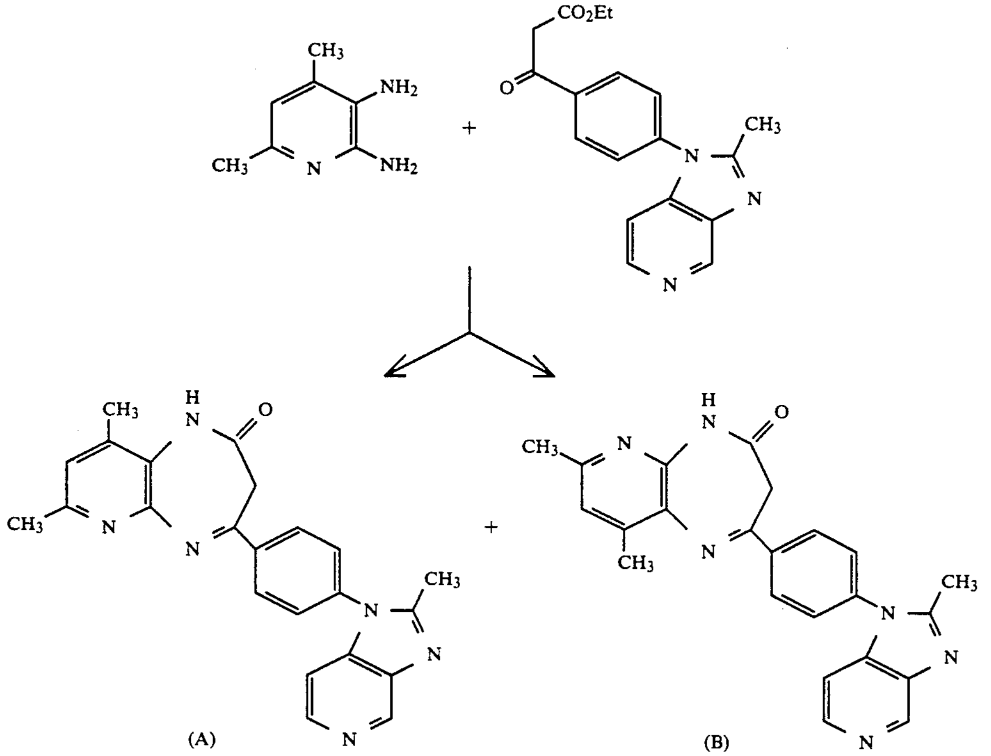

(A) (B)

A mixture of 2,3-diamino-4,6-dimethylpyridine (6.85 g, 50 mmol), ethyl 4'-(2-methylimidazo[4,5-c]pyrid-1-yl)benzoyl acetate (19.40 g, 60 mmol), silica gel (Merck Kieselgel 60, 40–63μ, 25 g) and toluene (500 ml) was heated at reflux under nitrogen for 6 hours. Water was removed from the reaction mixture by means of a 'Dean and Stark' apparatus. The mixture was then evaporated to dryness and the residue purified by column chromatography on silica, eluting with dichloromethane:methanol 19:1. Evaporation of the faster running isomer and recrystallisation from ethyl acetate gave Compound (B) (3.20 g, 16%), m.p. 256°–259° C.

Analysis %: Found: C,68.5; H,5.2; N,20.7; Requires: C,68.2; H,5.2; N,20.7.

Evaporation of the slower running isomer and recrystallisation from ethyl acetate:methanol gave Compound (A) (8.40 g, 42%), m.p. 244°–248° C.

Analysis %: Found: C,68.5; H,5.1; N,20.8; $C_{23}H_{20}N_6O.\frac{1}{2}H_2O$ requires: C,68.2; H,5.2; N,20.7.

EXAMPLE 49

3,5-Dihydro-2-[4-(2-methylimidazo[4,5-c]pyrid-1-yl)phenyl]-5,7,9-trimethyl-4H-pyrido[2,3-b][1,4]diazepin-4-one (a) Method A

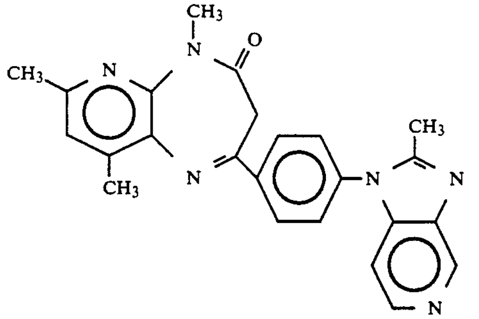

3,5-Dihydro-7,9-dimethyl-2-[4-(2-methylimidazo[4,5-c]pyrid-1-yl)-phenyl]-4H-pyrido[2,3-b][1,4]diazepin-4-one (3.19 g, 8 mmol) (Example 48 B) was stirred in dry dimethylformamide under nitrogen. Sodium hydride (60% dispersion in oil, 0.40 g, 10 mmol) was added and the mixture stirred at room temperature for 1 hour. Iodomethane (1.28 g, 9 mmol) was added and after being stirred for a further 2 hours the mixture was poured into water (100 $cm^3$). This was then extracted with dichloromethane (1×100 ml, 2×50 ml) and the combined extracts dried over sodium sulphate. Filtration and evaporation of the solution gave the crude product which was purified by column chromatography on silica eluting with dichloromethane:methanol 96:4. The product was recrystallised from ethyl acetate/methanol (2.99 g, 91%), m.p. 273°–276° C.

Analysis %: Found: C,69.9; H,5.5; N,20.2; Requires: C,70.2; H,5.4; N,20.5.

(b) Method B

A solution of 3-amino-4,6-dimethyl-2-methylaminopyridine (0.52 g, 3.4 mmol) and ethyl 4'-(2-methylimidazo[4,5-c]pyrid-1-yl)-benzoyl acetate (1.2 g, 3.7 mmol) in toluene (25 ml) was heated at reflux whilst removing water with a Dean and Stark apparatus. After 12 hours the solution was allowed to cool and the solvent was removed under vacuum. The residue was purified by column chromatography on silica, eluting with dichloromethane:methanol=9:1 and the product recrystallised from ethyl acetate/methanol to give the title compound (1.0 g, 75%) identical in all respects to that produced by Method A.

EXAMPLES 50-70

The compounds shown in Tables 5 and 6 below were prepared by the procedures of Examples 48 and 49(a) using the appropriate 2,3-diaminopyridine instead of 2,3-diamino-4,6-dimethylpyridine. The melting points and analyses of the compounds obtained are given in the Tables.

TABLE 5

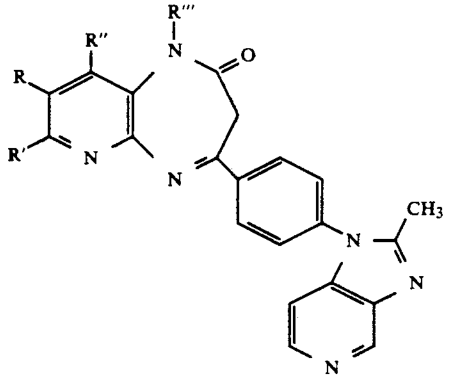

| Example | R | R' | R" | R''' | m.p. | Analysis % (Theoretical in brackets) C | H | N |
|---|---|---|---|---|---|---|---|---|
| 50 | H | H | $CH_3$ | H | 303-305° C. | 69.1<br>(69.0 | 4.7<br>4.7 | 22.0<br>22.1) |
| 51 | H | H | $CH_3$ | $CH_3$ | 239-241° C. | 68.9<br>(69.0 | 5.1<br>5.1 | 20.6<br>20.6) |
| 52 | H | $CH_3$ | $CH_3$ | $CH_3$ | 230-233° C. | 69.5<br>(69.4 | 5.5<br>5.5 | 20.3<br>20.1)+ |
| 53 | H | $CH_3$ | H | H | 253-256° C. | 67.5<br>(67.6 | 4.9<br>4.8 | 21.5<br>21.5)+ |
| 54 | H | $CH_3$ | H | $CH_3$ | 234-236° C. | 68.7<br>(68.5 | 5.1<br>4.9 | 20.9<br>20.8)# |
| 55 | Br | H | H | H | 250-252° C. | 55.1<br>(55.3) | 3.2<br>3.5) | 18.2<br>18.4)+ |
| 56 | Br | H | H | $CH_3$ | 249-251° C. | 57.2<br>(57.3 | 3.7<br>3.7 | 18.0<br>18.2) |
| 57 | H | H | H | H | 228-230° C. | 67.06<br>(66.83 | 4.37<br>4.54 | 22.39<br>22.27)+ |
| 58 | H | H | H | $CH_3$ | 155-156° C. | 66.16<br>(65.96 | 4.65<br>5.03 | 20.93<br>20.99) |
| 59 | $CO_2Et$ | H | H | H | 246-248° C. | 64.73<br>(64.79 | 4.59<br>4.61 | 18.55<br>18.89)+ |
| 60 | $CO_2Et$ | H | H | $CH_3$ | 201-204° C. | 65.98<br>(66.08 | 4.84<br>4.85 | 18.51<br>18.50) |

+calculated for 0.25 $H_2O$.
#calculated for ½$H_2O$.
reflex for 16h.

TABLE 6

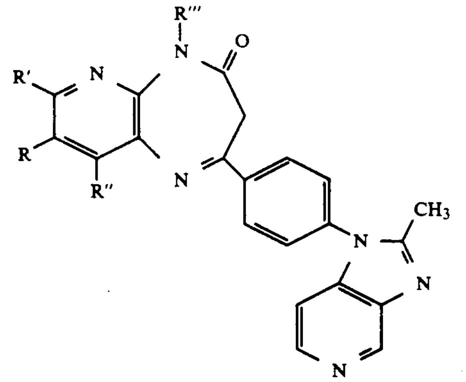

| Example | R | R' | R" | R''' | m.p. | Analysis % (Theoretical in brackets) C | H | N |
|---|---|---|---|---|---|---|---|---|
| 61 | H | H | $CH_3$ | H | 292-294° C. | 69.1<br>(68.7 | 4.7<br>4.8 | 22.0<br>21.7) |
| 62 | H | H | $CH_3$ | $CH_3$ | 252-255° C. | 68.9<br>(68.7 | 5.2<br>5.0 | 21.0<br>20.8)* |
| 63 | H | $CH_3$ | H | H | 252-255° C. | 63.5<br>(63.4 | 4.5<br>4.4 | 19.8<br>19.9)+ |
| 64 | H | $CH_3$ | H | $CH_3$ | 251-253° C. | 66.7<br>(66.9 | 5.3<br>5.1 | 20.3<br>20.5)# |

TABLE 6-continued

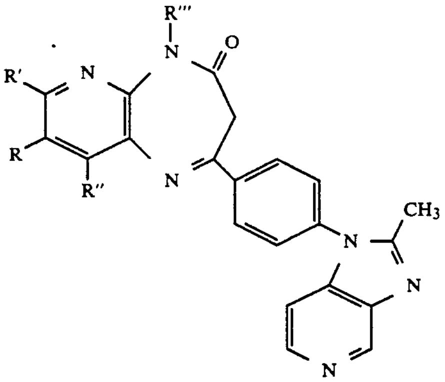

| Example | R | R' | R'' | R''' | m.p. | Analysis % (Theoretical in brackets) C | H | N |
|---|---|---|---|---|---|---|---|---|
| 65 | Br | H | H | H | 258–260° C. | 55.4 (55.3) | 3.3 3.5 | 18.6 18.4) |
| 66 | Br | H | H | $CH_3$ | 252–254° C. | 57.3 (57.3 | 3.8 3.7 | 18.2 18.2) |
| 67 | H | H | H | H | 252–253° C. | 66.49 (66.83 | 4.27 4.54 | 21.92 22.27) |
| 68 | H | H | H | $CH_3$ | 252–255° C. | 69.19 (69.10 | 4.81 4.74 | 22.06 21.98) |
| 69 | $CO_2Et$ | H | H | H | 243–245° C. | 64.85 (64.57 | 4.81 4.78 | 18.44 18.83) P |
| 70 | $CO_2Et$ | H | H | $CH_3$ | 211–213° C. | 66.00 (66.08 | 4.90 4.85 | 18.23 18.50) |

*calculated for 0.25 $H_2O$.
+calculated for 0.5 $CH_2Cl_2$.
#calculated for 1.0 $H_2O$.
calculated for 0.5 $H_2O$.
P calculated for 0.33 $H_2O$

TABLE 7

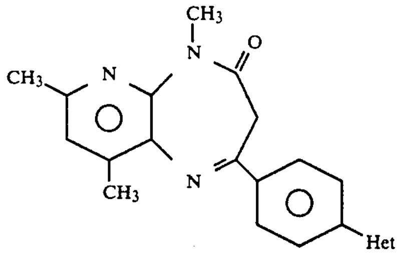

| Example | Het | m.p. | Analysis %/$^1$H NMR (Theoretical in brackets) C | H | N |
|---|---|---|---|---|---|
| 71 | 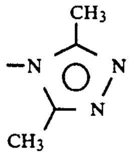 | 270–289° C. | 66.16 (66.43 | 6.09 6.16 | 21.15 20.81)* |
| 72 | 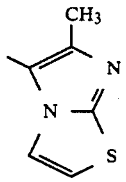 | 248–252° C. | ($CDCl_3$) 2.50, 2.56 and 2.63 (each 3H, s), 3.00 br (1H,s), 3.53 (3H, s), 4.32 br (1H, s), 6.84 (1H, d J=4.4 Hz), 7.02 (1H, s), 7.55 (1H, d J=4.4 Hz), 7.60 and 8.31 (each 2H, d J=8.3 Hz). | | |
| 73 | 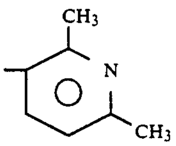 | 189–192° C. | 75.07 (74.97 | 6.38 6.29 | 14.91 14.57) |

*calculated for ⅓ ethyl acetate.

EXAMPLES 71-73

The compounds in Table 7 below were prepared from 3-amino-4,6-dimethyl-2-methylaminopyridine and the appropriate B-ketoester using the method of Example 49(b).

EXAMPLES 74–82

The compounds in Table 8 were prepared by the procedures of Examples 48, 49(a) and 49(b) using the appropriate heterocyclic diamine instead of 2,3-diamino-4,6-dimethylpyridine.

TABLE 8

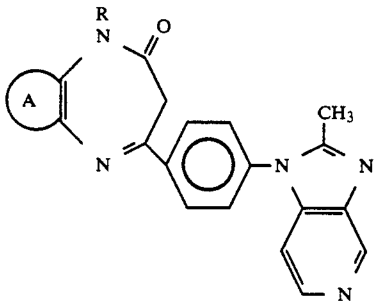

| Example | A | R | m.p. | Analysis % (Theoretical in brackets) C | H | N |
|---|---|---|---|---|---|---|
| 74 | 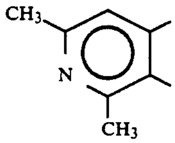 Δ | H | 240–2° C. | 66.83 (66.65 | 5.06 5.35 | 20.11 20.27)# |

TABLE 8-continued
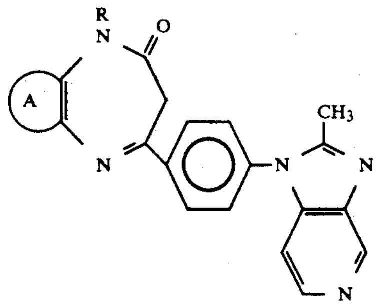
| Example | A | R | m.p. | Analysis % (Theoretical in brackets) C | H | N |
|---|---|---|---|---|---|---|
| 75 | 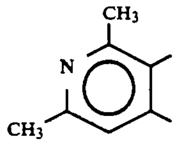 * | H | 262-3° C. | 67.00 (66.65 | 5.20 5.35 | 20.15 20.27)# |
| 76 | 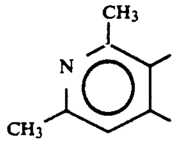 * | $CH_3$ | 240-1° C. | 68.76 (68.69 | 5.36 5.52 | 19.72 20.03)# |
| 77 | 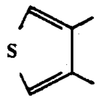 | H | 293-5° C. | 64.32 (64.03 | 4.05 3.93 | 18.76 18.34) |
| 78 | 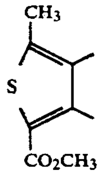 * | H | 268-9° C. | 61.92 (62.00 | 4.24 4.30 | 15.72 15.72) |
| 79 | 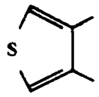 * | $CH_3$ | 217-9° C. | 64.86 (65.09 | 4.52 4.42 | 17.90 18.08) |
| 80 | 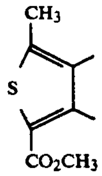 | $CH_3$ | 218-220° C. | 62.41 (62.73 | 4.72 4.61 | 14.76 15.24) |
| 81 | 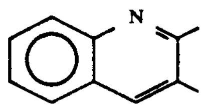 * | $CH_3$ | 278-282° C. | 71.17 (70.73 | 4.87 4.79 | 18.73 19.03)+ |
| 82 | 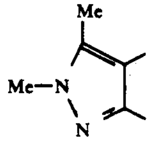 | H | — | $^1H$ NMR (300 MHz),$CDCl_3$) 2.39(3H,s), 2.63(3H,s), 3.77(2H,brs), 3.93(3H,s) 7.14(1H,d,J=5Hz), 7.49 (2H,d,J=8Hz), 8.42(3H,m), 9.08(1H,s). | | |
Notes for Table
Δ Compound exists as 1:1 mixture of amide tautomers.
Compound exists solely as the enamine tautomer.
+ Analysis for hemihydrate.
Analysis for hydrate.

EXAMPLE 83

5-Methyl-2-[4-(2-methylimidazo[4,5-c]pyrid-1-yl)phenyl]8-(pyrid-2-yl aminocarboxy)-5H-pyrido[2,3-b]]1,4] diazepin-4-one

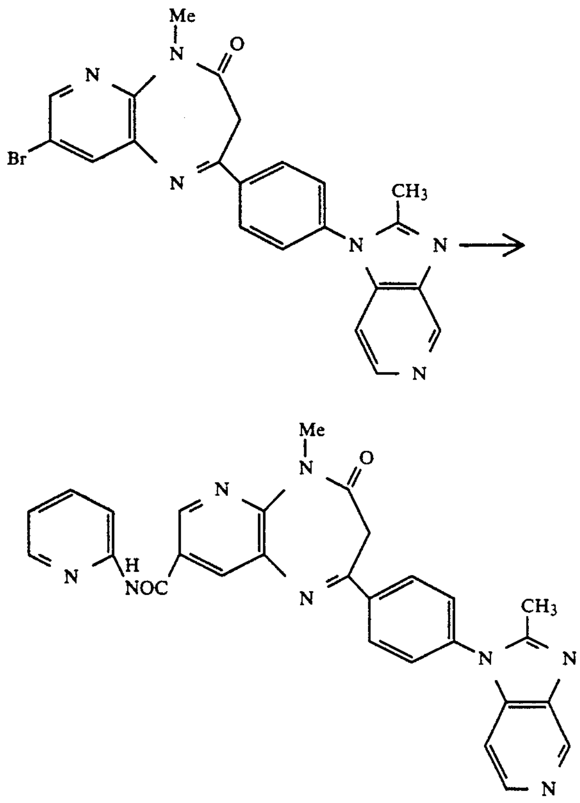

8-Bromo-5-methyl-2-[4-(2-methylimidazo]4,5-c]pyridin-1-yl)phenyl]-5H-pyrido[2,3-b][1,4]diazepin-4-one (435 mgs, 0.94 mmol), 2-aminopyridine (132 mg, 1.4 mmol), tetrabistriphenylphosphinepalladium (0) (50 mgs 0.04 mmol) and dimethylacetamide (10 $cm^3$) were mixed and heated under an atmosphere of carbon monoxide (balloon) at 120° C. for 8 hours. The cooled solution was poured into saturated sodium bicarbonate solution (50 $cm^3$) and extracted with ethyl acetate (3×50 $cm^3$). The combined extracts were dried over $MgSO_4$, filtered and evaporated to dryness. The residue was further purified by column chromatography ($SiO_2$ Merck Kieselgel 60) eluting with dichloromethane:methanol 97:3. The product-containing fractions were evaporated to dryness and recrystallised from ethyl acetate.

Yield 222 mg (47%) m.p. 276°-228° C.

Analysis %: Found: C,65.59; H,4.59; N,21.71; $C_{28}H_{22}N_8O_2$ $0.5H_2O$ requires: C,65.74; H,4.53; N,21.90.

EXAMPLES 84-86

The compounds of Table 9 were prepared by the method of Example 83 using the appropriate amine instead of 2-aminopyridine.

TABLE 9

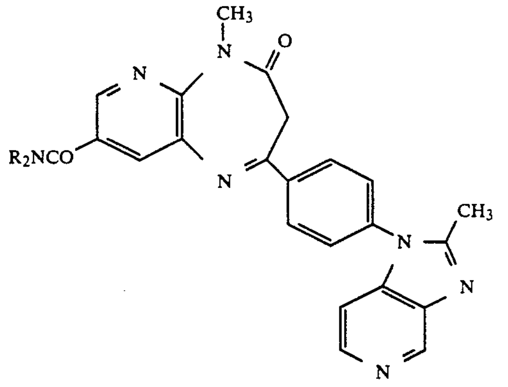

| Example | $R_2N$ | m.p. | Analysis % (Theoretical in brackets) C | H | N |
|---|---|---|---|---|---|
| 84 | 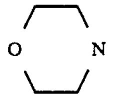 | 167-173° C. dec | 64.39 (64.36 | 5.42 5.40 | 18.48 18.76) |
| | | | $C_{27}H_{25}N_7O_3$ $0.5H_2O$ 0.25 $C_4H_{10}O$ | | |
| 85 | $Et_2N$ | 195-198° C. | 67.02 (67.25 | 5.70 5.95 | 19.40 19.61) |
| | | | $C_{27}H_2N_7O_2$ 0.25 $C_4H_{10}O$ | | |
| 86 | 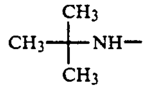 | 307-309° C. | 64.69 (64.92 | 5.68 5.85 | 19.33 19.63) |
| | | | $C_{27}H_{27}N_7O_2.H_2O$ | | |

EXAMPLES 87-88

The compounds shown in Table 10 were prepared by the method of Example 19 from the appropriate pyridodiazepinone

TABLE 10

| Example | A | m.p. | Analysis % (Theoretical in brackets) C | H | N |
|---|---|---|---|---|---|
| 87 | 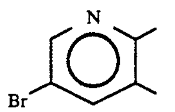 | 316-8° C. | 53.2 (53.5 | 3.5 3.9 | 16.0 16.3)* |
| 88 | 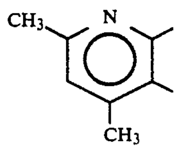 | 257-9° C. | 65.9 (65.6 | 5.0 5.0 | 19.8 19.9)# |

*calculated for 0.5 ethyl acetate
#calculated for 0.5 $H_2O$

EXAMPLES 89-90

The compounds of Table 11 were prepared by the method of Example 34 using the thiones of Examples 86 and 87 respectively.

TABLE 11

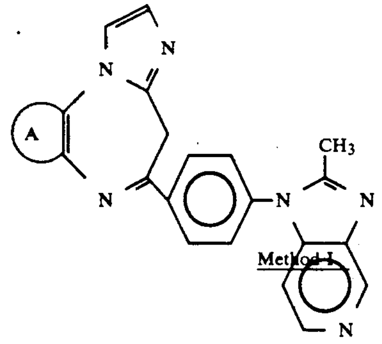

| Example | A | m.p. | Analysis % (Theoretical in brackets) C | H | N |
|---|---|---|---|---|---|
| 89 | 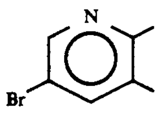 | 258–261° C. | 57.6 (57.6 | 3.4 3.6 | 20.5 20.5)* |
| 90 | 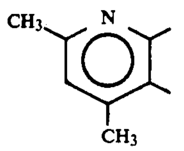 | 242–244° C. | 72.0 (71.6 | 5.0 5.0 | 23.2 23.4) |

*calculated for ⅓$H_2O$

The following examples 91–96 illustrate three methods, designated Methods I–III, for making substituted pyrazolodiazepines according to the invention.

Method I

EXAMPLE 91

1,3-Dimethyl-5-[4-(2-methylimidazo[4,5-c]pyrid-1-yl)phenyl]-1,6,7,8-tetrahydro-pyrazolo[3,4-b][1,4]diazepin-7-one (Compound C)

1,3-Dimethyl-7-[4-(2-methylimidazo[4,5-c]pyrid-1-yl)phenyl]1,4,5,6-tetrahydropyrazolo[3,4-b][1,4]diazepin-5-one (Compound D)

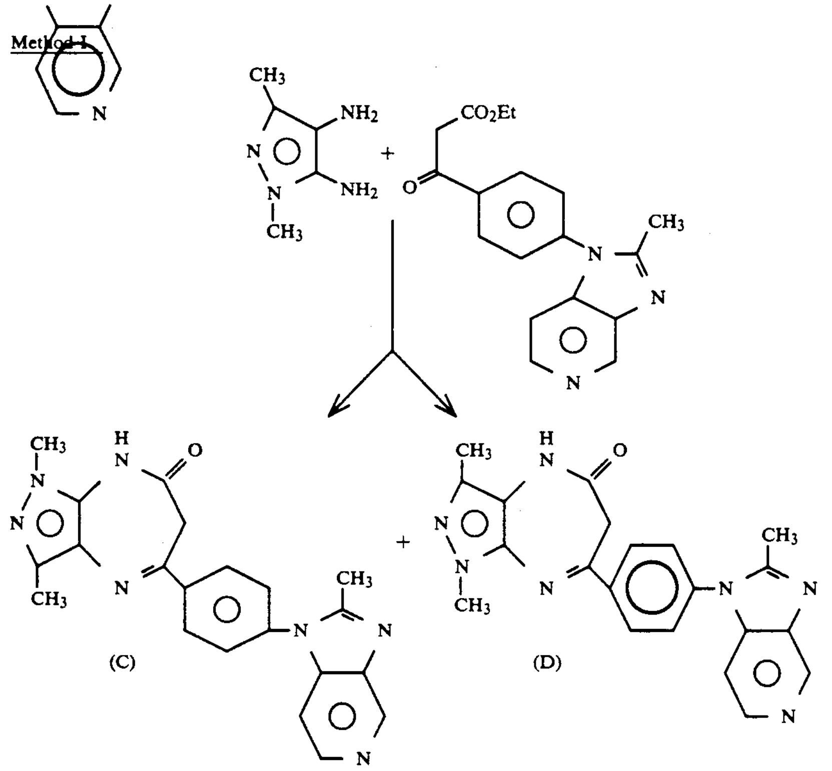

(C) (D)

A mixture of 4,5-diamino-1,3-dimethylpyrazole (8.98 g, 71.2 mmol), ethyl 4'-(2-methylimidazo[4,5-c]pyrid-1-yl)benzoyl acetate (23.0 g, 71.2 mmol), silica gel (Merck Kieselgel 60, 40–63μ, 14 g) and toluene (330 ml) was heated under nitrogen at reflux for 21 h. After cooling, the silica was filtered off and washed with methanol and a mixture of methanol and dichloromethane (1:1). The filtrate was concentrated under reduced pressure. The residue was dissolved in ethanol (300 ml) and sodium hydride (2.6 g, 60% oil dispersion, 66 mmol) was added in portions at room temperature and the mixture was stirred under nitrogen for 1 h. The solution was concentrated under reduced pressure and the residue was absorbed onto silica gel (60–200μ) and then purified by flash chromatography (gradient elution with ethyl acetate/diethylamine/methanol). First eluted was compound (D), which was further purified by recrystallisation from methanol to give a bright yellow powder (600 mg, 2%) m.p. 237°–238° C.

Analysis %: Found: C,63.27: H,5.18: N,24.49; $C_{21}H_{19}N_7O$. ⅔ $H_2O$ requires: C,63.22: H,5.18: N,24.58%.

The second eluted isomer (compound (C)) was further purified by recrystallisation from methanol to give a pale yellow powder (10 g, 38%), m.p. 313°–315° C.

Analysis %: Found: C,63.40; H,5.02; N,24.66; $C_{21}H_{19}N_7O$. ⅔ $H_2O$ requires C,63.22, H,5.18; N,24.58.

EXAMPLE 92

1,8-dimethyl-3-(2-methoxyethoxy)methyl-5[4-(2-methylimidazo[4,5-c]pyrid-1-yl)phenyl]-1,6,7,8-tetrahydro pyrazolo[3,4-b][1,4]-diazepin-7-one Method II

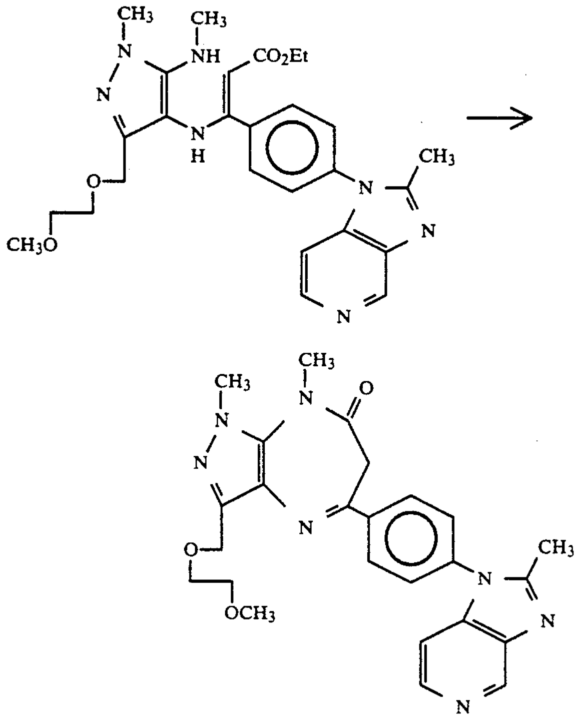

Ethyl 3-[3-(2-methoxyethoxy)methyl)-1-methyl-5-methylamino pyrazol-4-yl]amino-3-[4'-(2-methylimidazo[4,5-c]pyrid-l-yl)phenyl] propenoate (0.72 g, 1.4 mmoles) (see Preparation 69) was dissolved in ethanol (7 ml) and sodium hydride (60% dispersion in oil) (0.6 g, 1.5 mmoles) added. The reaction mixture was stirred under nitrogen at room temperature for 18 hours. The ethanol was removed under reduced pressure. The foam obtained was dissolved in dichloromethane (50 ml) and washed with saturated aqueous sodium chloride (20 ml). The dichloromethane solution was dried over magnesium sulphate and the solvent removed under reduced pressure. The crude product was chromatographed over silica eluting with 20% methanol in ethyl acetate. Fractions containing product were evaporated. The yellow foam obtained was sonicated in ether for 20 minutes, the white solid filtered off and dried in vacuo yielding the title compound (0.29 g, 44%) mp 142°-144° C.

Analysis % Found C,63.30; H,5.76; N,20.98; calc for $C_{25}H_{25}N_7O_3$ C,63.68; H,5.34; N,20.79.

EXAMPLES 93-95

The compounds of Table 12 were made by the method of Example 92 using the appropriately substituted aminopyrazole.

TABLE 12

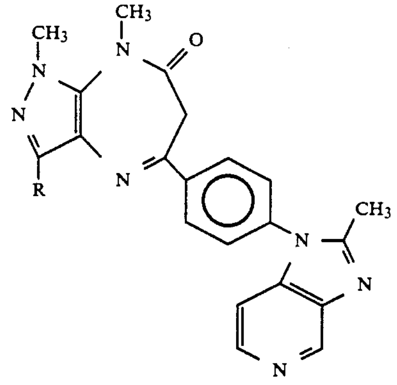

| Example | R | mp. | Analysis % Found: C | H | N | Calculated: C | H | N |
|---|---|---|---|---|---|---|---|---|
| 93 | 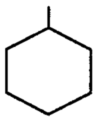 | 189-191° C. | 68.13 | 6.05 | 20.40 | $C_{27}H_{29}N_7O.0.5H_2O$ requires 68.05 | 6.34 | 20.57 |
| 94 | 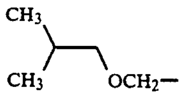 | 140° C. | 65.53 | 6.24 | 20.47 | $C_{26}H_{29}N_7O_2.0.25H_2O$ requires 65.59 | 6.24 | 20.59 |
| 95 | HOCH2— | 299-300° C. | 62.28 | 5.10 | 23.57 | $C_{22}H_{21}N_7O_2.0.5H_2O$ requires 62.25 | 5.22 | 23.10 |

EXAMPLE 96

5-[4-(2-methylimidazo[4,5-c]pyrid-1-yl)phenyl]-1,6,7,8-tetrahydro-1,3,8-trimethylpyrazolo[3,4-b][1,4]diazepin-7-one.

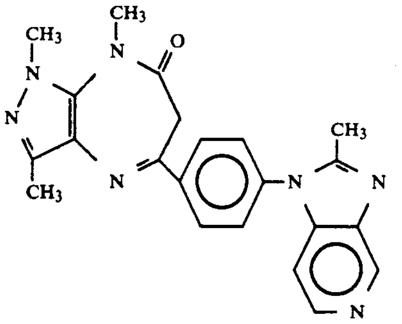

A suspension of 1,3-dimethyl-5-[4-(2-methylimidazo[4,5-c]pyrid-1-yl)phenyl]-1,6,7,8-tetrahydro-pyrazolo[3,4-b][1,4]diazepin-7-one (Example 91) in dry dimethylformamide (11 ml) under nitrogen at room temperature was treated with sodium hydride (56 mg, 60% dispersion in oil, 1.4 mmol) and stirred for 30 minutes to form a red solution. Methyl iodide (182 mg, 1.27 mmol) was added, and the mixture was stirred at room temperature for a further 16 hours. The solvent was removed under reduced pressure, and the residue was purified by flash chromatography eluting with ethyl acetate:diethylamine=20:1. The title compound was obtained as a white solid (220 mg, 48%), m.p. 248°-250° C. (from methanol).

Analysis %: Found: C,65.83; H,5.26; N,24.24; $C_{22}H_{21}N_7O$ requires: C,66.15; H,5.30; N,24.55.

EXAMPLES 97-134

The compounds shown in Tables 13 and 14 were prepared by the procedures of Examples 90-96 (Methods I-III) using the appropriate diaminopyrazoles and halides. The melting points and analyses of the compounds obtained are given in the Tables.

TABLE 13

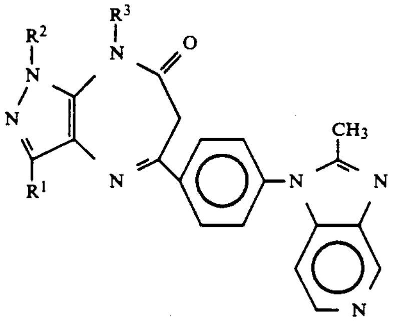

| Example | Method | $R^1$ | $R^2$ | $R^3$ | m.p. | Analysis % (Theoretical in brackets) C | H | N |
|---|---|---|---|---|---|---|---|---|
| 97 | I | $CH_3$ | t-Bu | H | 315-320° C. | 67.33<br>(67.42 | 6.02<br>5.89 | 22.72<br>22.94) |
| 98 | I | $CH_3$ | Ph | H | >300° C. | 69.29<br>(69.08 | 4.70<br>4.79 | 21.69<br>21.69)* |
| 99 | I | Ph | $CH_3$ | H | 245-248° C. | 68.35<br>(68.40 | 4.81<br>4.85 | 21.48<br>21.45)+ |
| 100 | III | $CH_3$ | $CH_3$ | $CH_2CH_2N(CH_3)_2$ | 183-185° C. | 64.51<br>(64.49 | 6.12<br>6.28 | 24.13<br>24.07)+ |
| 101 | III | $CH_3$ | $CH_3$ | $CH_2CON(CH_3)_2$ | 179-181° C. | 61.23<br>(61.46 | 5.69<br>5.77 | 22.96<br>22.94)# |
| *calculated for 0,25$H_2O$<br>+calculated for 0.5$H_2O$<br>#calculated for $H_2O$ | | | | | | | | |
| 102 | I | $CH_3$ | $CH_2.CH_2OH$ | H | 238-240° C. | 61.56<br>(61.58 | 5.37<br>5.28 | 22.88<br>22.85)I |
| 103 | I | Ph | $CH_2.CH_2OH$ | H | 185-190° C. | 65.29<br>(65.42 | 4.90<br>5.08 | 19.53<br>19.78)II |
| I calculated for 0.75$H_2O$<br>II calculated for .$H_2O$ | | | | | | | | |
| 104 | II | 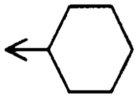 | H | $CH_3$ | 320° C. | 68.61<br>(68.85 | 6.04<br>6.00 | 21.36<br>21.62) |
| 105 | II | 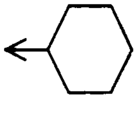 | H | $CH_2CH_2CH_2CH_2OH$ | 184° C. | * | | |
| 106 | II | 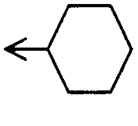 | $CH_3$ | H | 275-279° C. | Δ | | |

TABLE 13-continued

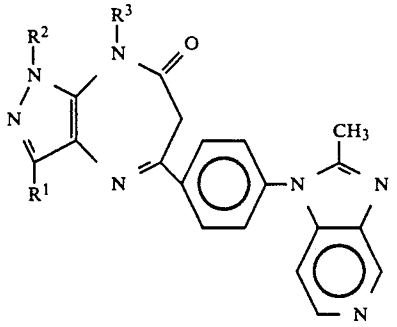

| Example | Method | $R^1$ | $R^2$ | $R^3$ | m.p. | Analysis % (Theoretical in brackets) C | H | N |
|---|---|---|---|---|---|---|---|---|
| 107 | III | 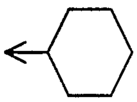 | $CH_3$ | $CH_3$ | 189-191° C. | 68.13<br>(68.05 | 6.05<br>6.34 | 20.40<br>20.57)+ |

•$^1$H NMR (250MHz, $CDCl_3$) 1.29-1.97(11H,m), 2.13(3H,m), 2.60(3H,s), 3.08(1H,m), 3.77(4H,m), 4.06(2H,t,J=7Hz), 5.29(1H,s), 7.16(1H,d,J=5Hz), 7.48(2H,d,J=8Hz), 8.31(2H,d,J=8Hz), 8.42(1H,d,J=5Hz), 9.10(1H,s).

Δ[1]H NMR (250MHz,$CDCl_3$), 1.29-1.90(8H,m), 2.02((2H,m), 2.58(3H,s), 2.95(1H,m), 3.71(2H,s), 3.85(3H,s), 7.14(1H,d,J=5Hz), 7.48(2H,d,J=8Hz), 8.29(2H,d,J=8Hz), 8.42(1H,d,J=5Hz), 9.10(1H,s), 9.84(1H,br s).

| Example | Method | $R^1$ | $R^2$ | $R^3$ | m.p. | C | H | N |
|---|---|---|---|---|---|---|---|---|
| 108 | II | 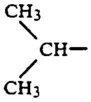 | $CH_3$ | $CH_3$ | 206-208° C. | 67.13<br>(67.43 | 5.94<br>5.89 | 22.87<br>22.93) |

+Hemihydrate

•$^1$H NMR (250MHz, $CDCl_3$) 1.29-1.97(11H,m), 2.13(3H,m), 2.60(3H,s), 3.08(1H,m), 3.77(4H,m), 4.06(2H,t,J=7Hz), 5.29(1H,s), 7.16(1H,d,J=5Hz), 7.48(2H,d,J=8Hz), 8.31(2H,d,J=8Hz), 8.42(1H,d,J=5Hz), 9.10(1H,s).

Δ[1]H NMR (250MHz,$CDCl_3$), 1.29-1.90(8H,m), 2.02((2H,m), 2.58(3H,s), 2.95(1H,m), 3.71(2H,s), 3.85(3H,s), 7.14(1H,d,J=5Hz), 7.48(2H,d,J=8Hz), 8.29(2H,d,J=8Hz), 8.42(1H,d,J=5Hz), 9.10(1H,s), 9.84(1H, br s).

| Example | Method | $R^1$ | $R^2$ | $R^3$ | m.p. | C | H | N |
|---|---|---|---|---|---|---|---|---|
| 109 | III | 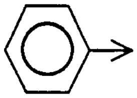 | $CH_3$ | $CH_3$ | 232° C. | 69.93<br>(70.26 | 5.07<br>5.02 | 20.83<br>21.23) |
| 110 | I | $CH_3$ | 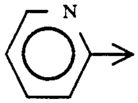 | H | 255° C. | 66.94<br>(66.95 | 4.53<br>4.49 | 24.78<br>24.99 |
| 111 | II | $CH_3$ | 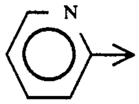 | $CH_3$ | 233-235° C. | 67.49<br>(67.52 | 4.80<br>4.79 | 24.19<br>24.22) |
| 112 | II | 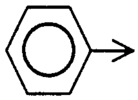 | 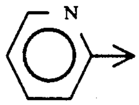 | H | 186-188° C. | 69.17<br>(69.34 | 4.36<br>4.46 | 21.19<br>21.56)+ |
| 113 | I | 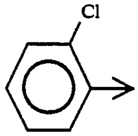 | $CH_3$ | H | >300° C. | 64.81<br>(64.79 | 4.25<br>4.18 | 20.06<br>20.35) |
| 114 | I | 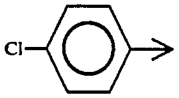 | $CH_3$ | H | >325° C. | 64.96<br>(64.79 | 4.20<br>4.18 | 20.34<br>20.35) |

TABLE 13-continued

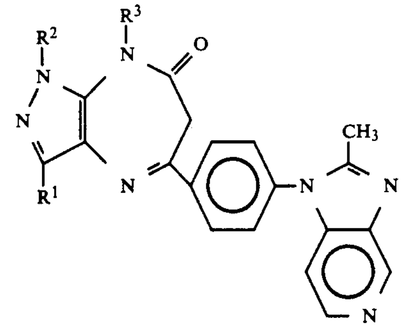

| Example | Method | $R^1$ | $R^2$ | $R^3$ | m.p. | Analysis % (Theoretical in brackets) C | H | N |
|---|---|---|---|---|---|---|---|---|
| 115 | III | 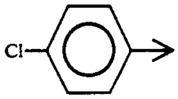 | $CH_3$ | $CH_3$ | 218-220° C. | 65.60<br>(65.39 | 4.51<br>4.47 | 19.94<br>19.77) |

+Calculated for hydrate

| Example | Method | $R^1$ | $R^2$ | $R^3$ | m.p. | C | H | N |
|---|---|---|---|---|---|---|---|---|
| 116 | I | 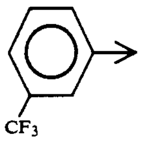 | $CH_3$ | H | 318-322° C. | 63.20<br>(62.91 | 4.05<br>3.91 | 18.97<br>19.02) |
| 117 | III | 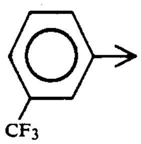 | $CH_3$ | $CH_3$ | 144-146° C. | 63.04<br>(62.97 | 4.14<br>4.25 | 18.16<br>18.36)* |
| 118 | II | 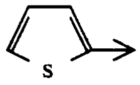 | $CH_3$ | H | 305-307° C. | 62.44<br>(62.32 | 4.32<br>4.36 | 21.27<br>21.19)+ |
| 119 | III | 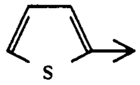 | $CH_3$ | $CH_3$ | 278-280° C. | 64.33<br>(64.22 | 4.48<br>4.53 | 20.72<br>20.97) |

*Calculated for $0.25H_2O$
+Calculated for Hemihydrate

| Example | Method | $R^1$ | $R^2$ | $R^3$ | m.p. | C | H | N |
|---|---|---|---|---|---|---|---|---|
| 120 | II | 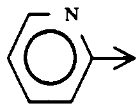 | $CH_3$ | H | 305-310° C. | 63.37<br>(63.15 | 4.71<br>4.87 | 23.28<br>23.56)@ |
| 121 | III | 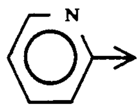 | $CH_3$ | $CH_3$ | 272° C. | 67.41<br>(67.52 | 4.73<br>4.79 | 23.86<br>24.23) |
| 122 | I | 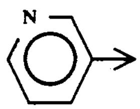 | $CH_3$ | H | 322-324° C. | | \$ | |

*Calculated for $0.25H_2O$
+Calculated for Hemihydrate
@Calculated for $1.5H_2O$
\$ $^1$H NMR (300MHz, $CDCl_3$), 2.62(3H,s), 3.87(2H,br s), 4.03(3H,s), 7.16(1H,d,J=7Hz), 7.44(1H,dd,J=5 and 7Hz), 7.53(2H,d,J=8Hz), 8.37(2H,d,J=8Hz), 8.45(2H,d,J=7Hz), 8.66(1H,J=5Hz), 9.11(1H,s), 9.43(1H,s) ppm.

| Example | Method | $R^1$ | $R^2$ | $R^3$ | m.p. | C | H | N |
|---|---|---|---|---|---|---|---|---|
| 123 | II or III | 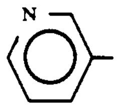 | $CH_3$ | $CH_3$ | 240-242° C. | 67.65<br>(67.52 | 4.84<br>4.79 | 23.85<br>24.23) |

TABLE 13-continued

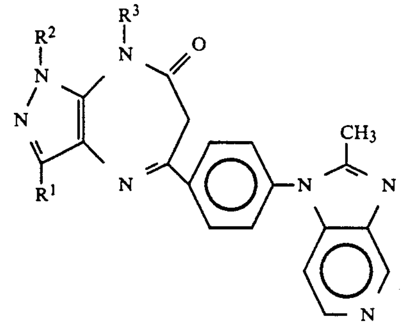

| Example | Method | $R^1$ | $R^2$ | $R^3$ | m.p. | Analysis % (Theoretical in brackets) C | H | N |
|---|---|---|---|---|---|---|---|---|
| 124 | III $ | 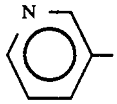 | $CH_3$ | $CH_2CH_3$ | 226–227° C. | 66.84 (66.79 | 4.95 5.19 | 22.75 23.08) |
| 125 | II | 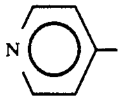 | $CH_3$ | H | 326–328° C. | 63.98 (64.07 | 4.98 4.95 | 22.99 23.44)Δ |
| 126 | III | 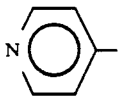 | $CH_3$ | $CH_3$ | 200° C. | 66.30 (66.23 | 4.84 4.92 | 23.50 23.76)+ |

ΔCalculated for $\frac{1}{4}$MeOH.$\frac{3}{4}H_2O$.
+Calculated for hemihydrate
$This reaction gave the following product in addition:

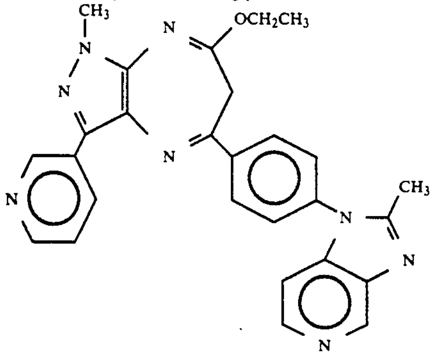

m.p. 198–200° C.
Found: C,66.98; H,5.08; N,23.10; $C_{27}H_{24}N_8O.\frac{1}{2}H_2O$ requires C,66.79; H,5.19; N,23.08%.

TABLE 14

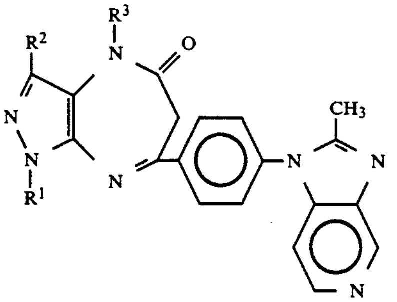

| Example | Method | $R^1$ | $R^2$ | $R^3$ | m.p. | Analysis % (Theoretical in brackets) C | H | N |
|---|---|---|---|---|---|---|---|---|
| 127 | I | $CH_3$ | $CH_3$ | $CH_3$ | 258–260° C. | 63.95 | 5.74 | 22.70 |

TABLE 14-continued

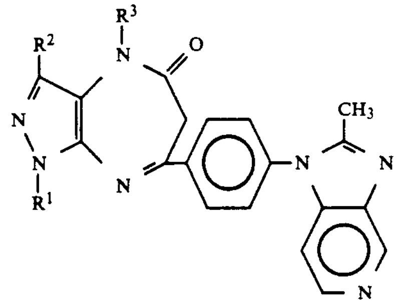

| Example | Method | $R^1$ | $R^2$ | $R^3$ | m.p. | Analysis % (Theoretical in brackets) C | H | N |
|---|---|---|---|---|---|---|---|---|
| | | | | | | (64.03 | 5.84 | 22.73)* |
| 128 | I | t-Bu | $CH_3$ | H | 265-270° C. | 66.81 | 5.83 | 23.00 |
| | | | | | | (66.72 | 5.95 | 22.70)+ |
| 129 | I | $CH_3$ | Ph | H | >300° C. | 69.55 | 4.75 | 21.56 |
| | | | | | | (69.78 | 4.73 | 21.91) |
| 130 | I | $CH_2.CH_2.OH$ | $CH_3$ | H | 294-297° C. | 62.01 | 5.49 | 22.53 |
| | | | | | | (62.24 | 5.22 | 23.09) |
| 131 | I | $CH_2.CH_2OH$ | Ph | H | 285-290° C. | 67.78 | 4.93 | 20.33 |
| | | | | | | (67.91 | 4.85 | 20.53) |
| 132 | I | $CH_3$ | 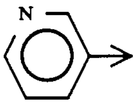 | H | 320° C. | 67.13 | 4.50 | 24.97 |
| | | | | | | (66.95 | 4.49 | 24.98) |
| 133 | III | t-Bu | $CH_3$ | $CH_3$ | 270-272° C. | 67.99 | 6.37 | 21.95 |
| | | | | | | (68.01 | 6.16 | 22.21) |
| 134 | I | $CH_3$ | 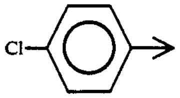 | H | 205-208° C. | 63.78 | 4.07 | 20.07 |
| | | | | | | (63.60 | 4.31 | 19.97) |

*Calculated for $1.0CH_3OH$
+Calculated for $0.25H_2O$
Calculated for $0.5H_2O$

EXAMPLE 135-137

The compounds shown in Table 15 were prepared by the method of Example 19 from the appropriate pyrazolodiazepinone.

TABLE 15

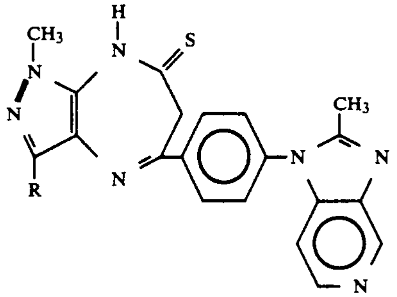

| Example | R | m.p. | Yield | |
|---|---|---|---|---|
| 135 | $CH_3$ | — | 52% | $^1H$ NMR(300MHz,$CDCl_3/CD_3OD$)δ= 2.38(3H,s), 2.55(3H,s), 3.80(3H,s), 4.07(2H,s), 7.13(1H,d,J=5Hz), 7.45(2H,d,J=6Hz), 8.31(1H,d,J=5Hz), 8.44(2H,d,J=6Hz), 8.95(1H,s). |

TABLE 15-continued

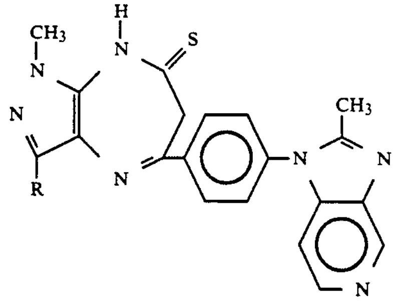

| Example | R | m.p. | Yield | |
|---|---|---|---|---|
| 136 | 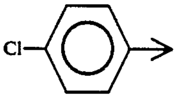 | 203-205° C. | 71% | $^1$H NMR(300MHz,CDCl$_3$) 2.62(3H,s), 4.01(3H,s), 4.25(2H,s), 7.18(1H,d,J=5Hz), 7.51(4H,m), 8.10(1H,d,J=9Hz), 8.15(1H,d,J=5Hz), 8.44(1H,d,J=5Hz), 8.15(2H,m), 9.11(1H,s). |
| 137 | 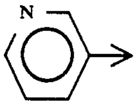 | 270-275° C. | 61% | Analysis %:- Found: C,60.67; H,4.61; N,22.25. $C_{25}H_{20}N_8S$.. 1.75 $H_2O$ requires C,60.53; H,4.77; N,22.59. |

EXAMPLE 138

1,6-Dihydro-1,9-dimethyl-5-[4-(2-methylimidazo[4,5-c]pyrid-1-yl)phenyl]-3-(3-pyridyl)triazolo[3,4-g]pyrazolo[3,4-b][1,4]diazepine

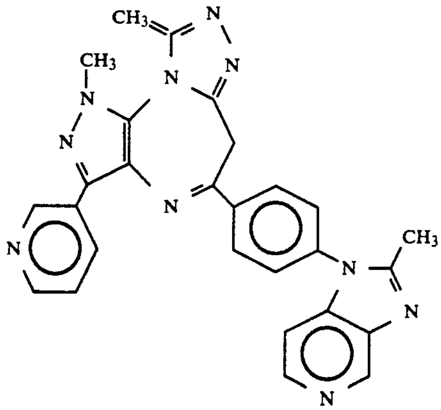

The thione of Example 139 (464 mg, 1 mmol), hydrazine hydrate (100 mg, 2 mmol) red mercuric oxide (216 mg, 1 mmol) and n-butanol were stirred together at reflux under nitrogen for 15 minutes, and at room temperature for 1 hour. The mixture was filtered through Arbocel filter aid, and the filter cake was washed with methanol. The filtrate was concentrated under reduced pressure, and the residue was suspended in triethylorthoacetate (9 ml) at reflux. Acetic acid (3 ml) was added, and the resulting solution was heated for 1½ hours at reflux. The solvent was removed in vacuo, and the residue was dissolved in 1M hydrochloric acid (20 ml), washed with ethyl acetate, and the aqueous phase was neutralised with saturated aqueous potassium carbonate. The product was extracted into dichloromethane (2×20 ml), dried ($MgSO_4$) and the solvent was removed in vacuo. The residue was purified by flash chromatography (eluting with dichloromethane:methanol=85:15) followed by trituration with ethyl acetate/ether=1:3. The title compound was obtained as a buff solid (95 mg, 20%), m.p. 208° C.

$^1$H NMR (500MHz, CDCl$_3$), 2.59(3H,s), 2.73(3H,s), 3.51(1H,d,J=15Hz), 4.11(3H,s), 5.05(1H,d,J=15Hz), 7.12(1H,d,J=5Hz), 7.44(1H,dd,J 6 and 8Hz), 7.51(2H,d,J=8Hz), 8.38(2H,d,J=8Hz), 8.43(2H,m), 8.66(1H,d,J 6Hz), 9.07(1H,s), 9.40(1H,s).

EXAMPLES 139-141

The compounds of Table 16 were prepared by the method of Example 34 using the thiones of Examples 135-137 respectively, and effecting the ring-closure with formic acid.

TABLE 16

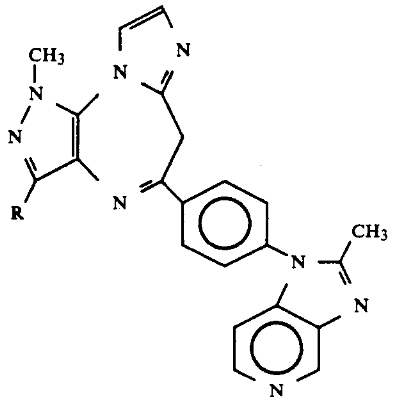

| Example | R | m.p. | Yield | Analysis % (Theoretical in brackets) C | H | N |
|---|---|---|---|---|---|---|
| 139 | $CH_3$ | 268-270° C. | 14% | 66.42<br>(66.16 | 5.10<br>5.07 | 26.44<br>26.84)+ |
| 140 | 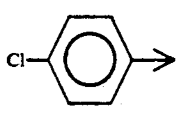 | 245-248° C. | 29% | $^1$HNMR(300MHz, $CDCl_3$), 2.59(3H,s), 4.16(3H,s), 4.20(2H,brs), 7.13(1H,d,J=5Hz), 7.33(1H,s), 7.48(5H,m), 8.11(1H,d,J=7Hz), 8.16(1H,d,J=6Hz), 8.40(3H,m), 9.10(1H,s)ppm. | | |
| 141 | 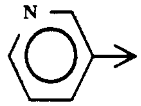 | 243-245° C. | 16% | 67.19<br>(67.49 | 4.47<br>4.61 | 25.87<br>26.23) |

+Calculated for hemihydrate

EXAMPLE 142

1,6,7,8-Tetrahydro-5-[4-(2-methylimidazo[4,5-c]pyrid-1-yl)phenyl]-1,3,6,8-tetramethylpyrazolo[3,4-b][1,4]diazepin-7-one

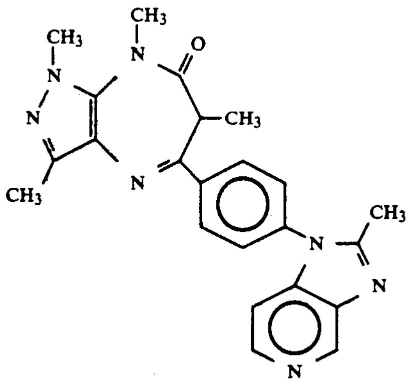

1,3-Dimethyl-5-[4-[4-(2-methylimidazo[4,5-c]pyrid-1-yl)phenyl]-1,6,7,8-tetrahydro-pyrazolo[3,4-b][1,4]diazepin-7-one (Example 91) (752 mg, 2.0 mmol) was added to a suspension of sodium hydride (80 mg, 60% dispersion in oil, 2.0 mmol) in dry dimethyl formamide (10 ml) under nitrogen at room temperature. The mixture was sonicated for 5 minutes, then stirred for 1 hour. Methyl iodide (284 mg, 2.0 mmol) was added, and after 30 minutes more sodium hydride (120 mg, 60% dispersion in oil, 3 mmol). After a further 30 minutes, methyl iodide (284 mg, 2.0 mmol) was added, and the dark brown mixture was stirred at room temperature for a further 2 hours. The mixture was then poured into iced water (50 ml) and extracted with dichloromethane (4×30 ml). The combined extracts were dried ($MgSO_4$), concentrated under reduced pressure and the resulting brown gum was purified by column chromatography (Merck silica gel, 70 g, 10–40 m) eluting with ethyl acetate:diethylamine=20:1. Fractions containing product were evaporated and the residue was recrystallised from ethyl acetate/methanol to give the title compound as a white solid, m.p. 222°-225° C. Analysis %: Found: C,66.00; H,5.77; N,23.01. $C_{23}H_{23}N_7O$. ½ $H_2O$ requires C,65.86; H,5.69; N,23.37%.

EXAMPLE 143

8,9-Dichloro-6-methyl-5-[4-(2-methylimidazo[4,5-c]pyrid-1-yl)phenyl]-6H-imidazo[1,2-a][1,5]benzodiazepine.

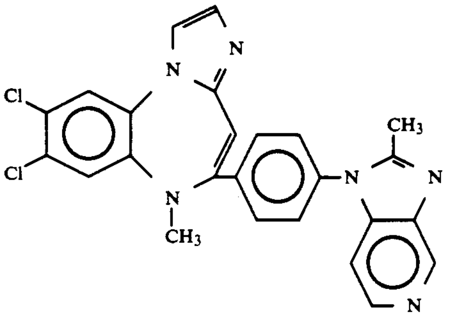

A solution of 8,9-dichloro-5-[4-(2-methylimidazo[4,5-c]pyrid-1-yl-phenyl]-3H-imidazo[1,2-a][1,5]benzodiazepine (230 mg, 0.5 mmol) in dry dimethyl sulphoxide (2 ml) was added to a stirred suspension of sodium hydride (20 mg, 60% dispersion in oil, 0.5 mmol) in dry dimethyl sulphoxide (1 ml) under nitrogen with cooling using a cold water bath. The mixture was stirred for 1½ hours at ca 15° C. and 30 minutes at room temperature to give a dark brown solution. Methyl iodide (78 mg, 0.55 mmol) was added and the mixture was stirred for 45 minutes. The mixture was poured into dichloromethane (150 ml) and washed with water (7×70 ml), and brine (50 ml). The organic solution was dried ($MgSO_4$), concentrated under reduced pressure, and the residue was purified on silica gel (20 g, 10–40μ), eluting with ethyl acetate:diethylamine=19:1. The product was further purified by trituration with dry ether to give the title compound as a brown solid (5 mg, 2%), m.p. 268°-270° C.

$^1$H-NMR (300 MHz, $CDCl_3$) 2.64 (3H,s), 3.07 (3H,s), 6.28 (1H,s) 7.17 (1H,d,J 5 Hz), 7.23 (1H,s), 7.28 (1H,s), 7.39 (1H,s), 7.41 (1H,s), 7.47 (2H, d, J 8 Hz), 7.65 (2H, d, J 8Hz), 8.43 (1H, d, J 5Hz), 9.10 (1H, s).

EXAMPLE 144

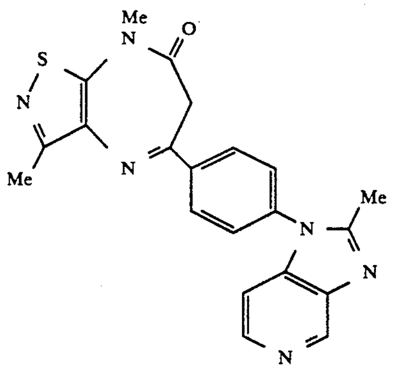

6,8-Dihydro-3,8-dimethyl-5-[4-(2-methylimidazo[4,5-c]pyrid-1-yl)phenyl]-7H-isothiazolo[4,5-b][1,4]diazepin-7-one (a) 5-Bromo-3-methyl-4-nitroisothiazole (J. Chem. Soc., (1959), 3061) (1.12 g, 5.0 mmol) was suspended in ethanol (20 ml) at 0° C. and gaseous methylamine was bubbled through for 20 minutes. The mixture was stirred at room temperature for 30 minutes and the solvent was removed under reduced pressure. The residue was dissolved in dichloromethane (100 ml) and washed with saturated aqueous sodium bicarbonate (50 ml). The organic layer was dried ($MgSO_4$), concentrated under reduced pressure and purified by flash chromatography (eluting with dicholoromethane) to give 3-methyl-5-methylamino-4-nitroisothiazole (662 mg, 77%) as a white solid, m.p. 153° C.

Analysis %: Found: C,34.58; H,4.00; N,23.73. $C_5H_7N_3O_2S$ requires C,34.68; H,4.07; N,24.26.

$^1$H NMR (250MHz, $CDCl_3$), 2.65 (3H, s), 3.23 (3H, d, J 5Hz), 8.20 (1H, br s).

(b) 3-Methyl-5-methylamino-4-nitroisothiazole (520 mg, 3.0 mmol) was reduced according to the procedure of Preparation 11(d) to give 4-amino-3-methyl-5-methylaminoisothiazole (422 mg, 98%).

$^1$H NMR (250 MHz, $CDCl_3$) 2.20 (2H,br s), 2.30 (3H, s), 2.95 (3H, s), 4.30 (1H, br s).

(c) A mixture of 4-amino-3-methyl-5-methylaminoisothiazole (420 mg, 2.9 mmol), ethyl 4'-(2-methylimidazo[4,5-c]pyrid-1-yl)benzoylacetate (969 mg, 3.0 ml) and anhydrous zinc chloride (39 mg, 0.29 mmol) was stirred in ethanol at reflux for 18 hours. A further amount (39 mg) of zinc chloride was added, and heating was continued in a sealed vessel at 100° C. for 6 hours. The mixture was cooled and sodium hydride (120 mg, 60% oil dispersion, 3.0 mmol) was added. The mixture was stirred at room temperature for 16 hours, and the solvent was removed under reduced pressure. The residue was dissolved in dichloromethane (150 ml) and washed with brine (50 ml). The organic solution was dried ($MgSO_4$) and concentrated under reduced pressure. The residue was purified by flash chromatography (eluting with dichloromethane/methanol=9:1) followed by reverse phase h.p.l.c. ($C_{18}$ silylated silica, methanol/water=70:30) to give a solid which was recrystallised from ethyl acetate. The title compound was obtained as a white solid (190 mg, 16%), m.p. 214°-216° C.

Analysis %: Found: C,61.05; H,4.58; N,20.19. $C_{21}H_{18}N_6OS$. $0.5H_2O$ requires C,61.30; H,4.65; N,20.42.

PREPARATION 1

Ethyl 4'-(2-methylimidazo[4,5-c]pyrid-1-yl)benzoyl acetate

Method A

Essentially the method of Y. Kishi, S. M. Hannick, *J. Org. Chem.*, 1983, 48, 3833.

Zinc dust (894 mg, 13.7 mmol) was suspended in dry tetrahydrofuran (3 ml) under nitrogen and sonicated at room temperature for 10 minutes. Ethyl bromoacetate (2 drops) was added and the mixture was refluxed for 5 minutes. A solution of 1-(4-cyanophenyl)-2-methylimidazo[4,5-c]pyridine (640 mg, 2.74 mmol) in dry tetrahydrofuran (6 ml) was added and the mixture was refluxed for 5 minutes. A solution of ethyl bromoacetate (1.822 g, 10.94 mmol) in dry tetrahydrofuran (2 ml) was added dropwise over 1 hour at reflux, and after a further 10 minutes, the mixture was allowed to cool to room temperature. 50% aqueous potassium carbonate (1 ml) was added and the mixture was stirred for 45 minutes at room temperature, and then filtered through Arbocel filter aid, washing with THF. The filtrate was concentrated under reduced pressure to give a yellow gum. This material was treated with a mixture of 20% aqueous trifluoro acetic acid (10 ml) and dichloromethane (50 ml) at room temperature for 15 minutes. The mixture was neutralised by the addition of saturated aqueous sodium hydrogen carbonate, and then extracted with dichloromethane (2×30 ml). The combined extracts were dried ($MgSO_4$), concentrated under reduced pressure, and the crude product was purified by flash chromatography (eluting with 10–20% methanol in ethyl acetate) to give ethyl 4'-(2-methylimidazo[4,5-c]pyrid-1-yl)benzoylacetate (480 mg, 54%) as a yellow gum.

Material obtained by Method A was a white solid, m.p. 111°-112° C. (after recrystallisation from ethyl acetate).

$^1$H-NMR (300 MHz, $CDCl_3$) 1.32 (3H, t, J 6Hz), 2.61 (3H, s), 4.09 (2H, s), 4.28 (2H, q, J 6Hz), 7.16 (1H, d, J 6Hz), 7.55 (2H, d, J 9Hz), 8.23 (2H, d, J 9Hz), 8.46 (1H, d, J 6Hz), 9.09 (1H, s).

Method B (a) 4-(4-Acetylphenyl)amino-3-nitropyridine hydrochloride

A solution of 4-chloro-3-nitropyridine hydrochloride (9.75 g, 50 mmol) in ethanol (40 ml) was added to a slurry of p-aminoacetophenone (6.76 g, 50 ml) in ethanol (25 ml), and the mixture was stirred at room temperature overnight. The mixture was chilled in ice, and the yellow solid filtered off and dried in vacuo. Yield 10.1 g (69%), m.p. 197°-200° C.

$^1$H-NMR (300 MHz, DMSO-$d_6$) 2.61 (3H, s), 7.19 (1H, d, J 7Hz), 7.53 (2H, d, J 8Hz), 8.07 (2H, d, J 8Hz), 8.33 (1H, d, J 7Hz), 9.36 (1H, s), 10.74 (1H, s).

(b) 4-(4-Acetylphenyl)amino-3-aminopyridine 4-(4-Acetylphenyl)amino-3-nitropyridine hydrochloride (2.0 g, 71.8 mmol) was partitioned between aqueous sodium hydroxide and dichloromethane (3×20 ml). The combined organic phases were (kPa) for 3.5 hours. The catalyst was filtered off, and the solvent removed under reduced pressure to give a brown solid, (1.8 g) which was used directly for the next reaction without purification, m.p. 165°-166° C. (after recrystallisation from ethanol).

$^1$H-NMR (300 MHz, DMSO-$d_6$) 2.47 (3H, s), 5.00 (2H, br.s), 7.04 (3H, m), 7.70 (1H, br.s), 7.83 (2H, d, J 8Hz), 7.98 (1H, br.s), 8.12 (1H, s).

(c) 1-(4-Acetyl)phenyl-2-methylimidazo[4,5-c]pyridine

A solution of 4-(4-acetylphenyl)amino-3-aminopyridine (68.0 g, 0.3 mmol) in acetic acid (204 ml) and acetic anhydride (204 ml) was heated at 95° C. for 1.5 hours then cooled and concentrated under reduced pressure. The residue was dissolved in water (500 ml) and rendered basic by the addition of saturated aqueous ammonia. The product was filtered off, washed with water (2×100 ml) and dried in vacuo to give the title compound, (61.0 g, 81%) as a brown solid, m.p. 155°-156° C. (after recrystallisation from water).

$^1$H-NMR (300 MHz, $CDCl_3$), 2.59 (3H, s), 2.72 (3H, s), 7.12 (1H, d, J 5Hz), 7.53 (2H, d, J 8Hz), 8.22 (2H, d, J 8Hz), 8.40 (1H, d, J 5Hz), 9.04 (1H, s).

(d) Ethyl 4'-(2-methylimidazo[4,5-c]pyrid-1-yl]benzoylacetate

A solution of 1-(4-acetyl)phenyl-2-methylimidazo[4,5-c]-pyridine (17.5 g, 69.7 mmol) in dry tetrahydrofuran (175 ml) was added to a slurry of sodium hydride (3.68 g, 153 mmol) in a mixture of dry tetrahydrofuran (35 ml) and diethyl carbonate (24.7 g, 209 mmol) at reflux with stirring over 45 minutes. After a further 1 hour, the mixture was cooled, hexane (200 ml) was added and the resulting precipitate was filtered off and washed with hexane (2×100 ml). The solid was suspended in ethyl acetate (200 ml) and acetic acid (10.2 g) was added. After being stirred for 15 minutes, water (200 ml) was added, and the organic layer was separated. The aqueous phase was extracted with ethyl acetate (100 ml) and the combined organic solutions were washed with water (200 ml), dried ($MgSO_4$) and concentrated to give a gum (17.3 g, 77%). This material could be further purified if desired by flash chromatography (eluting with ethyl acetate:methanol=7:1) to give the title compound as a white solid.

Method C (a) 4-(2-Methylimidazo[4,5-c]pyrid-1-yl)benzoic acid

A mixture of 4-(2-methylimidazo[4,5-c]pyrid-1-yl)benzonitrile (12.0 g, 51.3 mmol) and 40% aqueous sodium hydroxide (55 ml) in absolute ethanol (55 ml) was heated at reflux for 1½ hours. The solvent was removed under reduced pressure, and the brown residue was dissolved in water. The solution was chilled to 0° C. by the addition of ice. Glacial acetic acid (ca 33 ml) was added slowly. The buff solid which precipitated was filtered off, washed with water, and dried in vacuo at 70° C. Yield 9.14 g (70%).

$^1$H-NMR (300 MHz, DMSO-$d_6$) 2.49 (3H, s), 7.25 (1H, d, J 6Hz), 7.72 (2H, d, J 6Hz), 8.17 (2H, d, J 6Hz), 8.30 (1H, d, J 6Hz), 8.92 (1H, s).

(b) Ethyl 4'-(2-methylimidazo[4,5-c]pyrid-1-yl)benzoylacetate

Oxalyl chloride (17.0 ml, 184 mmol) was added to a mixture of 4-(2-methylimidazo[4,5-c]pyrid-1-yl) benzoic acid (11.64 g, 46 mmol) and dry dimethylformamide (0.2 ml) in dry dichloromethane (200 ml) under nitrogen with ice cooling. At the end of the addition, the mixture was sonicated for 1 hour at room temperature, and then concentrated under reduced pressure and re-suspended in dry dichloromethane (200 ml).

In a separate flask, isopropylmagnesium chloride (137 ml of a 2M solution in tetrahydrofuran, 274 mmol) was added dropwise over 20 minutes to a solution of ethyl malonic acid (18.14 g, 137 mmol) in dry dichloromethane (100 ml) at 0° C. After a further 20 minutes, the solution was added at room temperature to the suspension of the acid chloride generated above. The red mixture was sonicated at room temperature for 30 minutes and then cooled in ice whilst 4N hydrochloric acid (250 ml) was added. The mixture was stirred for 10 minutes at room temperature, diluted with dichloromethane (200 ml), and the layers were separated. The aqueous layer was neutralised with saturated aqueous sodium bicarbonate, and extracted with dichloromethane (3×200 ml). The combined extracts were dried ($MgSO_4$) and concentrated under reduced pressure to give a yellow gum, which crystallised slowly on standing. Yield 12.10 g (80%).

Preparation 2

Ethyl 4'-(2,4,5-trimethylimidazo[4,5-c]-pyrid-1-yl)benzoylacetate

The procedure of Preparation 1, Method A was followed using as starting materials zinc dust (11.54 g), 1-(4-cyanophenyl)-2,4,6-trimethylimidazo[4,5-c]pyridine (9.30 g) and ethyl bromoacetate (23.7 g). The yield of the title compound was 10.50 g, 84% as a yellow gum.

$^1$H-NMR (300 MHz, $CDCl_3$) 1.37 (3H, t, J 7Hz), 2.60 (3H, s), 2.63 (3H, s), 2.92 (3H, s), 4.11 (2H, s), 4.32 (2H, q, J 7Hz), 6.82 (1H, s), 7.55 (2H, d, J 8Hz), 8.23 (2H, d, J 8Hz).

PREPARATION 3

Ethyl 4-(2,6-dimethylpyrid-3-yl)benzoyl acetate

The procedure of Preparation 1, Method A, was followed but using 3-(4-cyanophenyl)-2,6-dimethylpyridine instead of 1-(4-cyanophenyl)-2-methylimidazo[4,5-c]pyridine to obtain the title compound.

$^1$H NMR ($CDCl_3$): 1.30 (3H, t, J 6Hz), 2.52 and 2.62 (each 3H, s), 4.05 (2H, s), 4.25 (2H, q, J 6Hz), 7.11 (1H, d, J 6Hz), 7.45 (3H, m), 8.08 (2H, d, J 9 Hz).

PREPARATION 4

Ethyl 2-(2-methylimidazo[4,5-c]pyrid-1-yl)pyrid-5-oyl acetate

(a) 4-Chloro-1-(5-ethoxycarbonylpyrid-2-yl)-2-methylimidazo-[4,5-c]pyridine

4-Chloro-2-methylimidazo[4,5-c]pyridine* (3.34 g, 20 mmol), and ethyl 6-chloronicotinate (3.71 g, 26.2 mmol) were dissolved in N,N-dimethylformamide (42 ml). Potassium carbonate (2.76 g, 20 mmol) was added and the mixture was refluxed overnight. The reaction mixture was cooled, the solvent removed under reduced pressure and the crude product purified by flash chromatography eluting with ethyl acetate. Fractions containing product were evaporated and the resulting foam triturated with ether. The solid was filtered and dried under reduced pressure yielding the title compound as a yellow solid (3.2 g, 51%).

*Made by the method described in *Chem. phar. Bull.*, 1964, 12 (8), 866–872.

$^1$H NMR (300 MHz, $CDCl_3$) 1.47 (3H, t, J 6Hz), 2.84 (3H, s), 4.56 (2H, q, J 6Hz), 7.38 (1H, d, J 4Hz), 7.59 (1H, d, J 6Hz), 8.25 (1H, d, J 4Hz), 8.63 (1H, d, J 6Hz), 9.36 (1H, s).

(b) 1-(5-Ethoxycarbonylpyrid-2-yl)-2-methylimidazo[4,5-c]pyridine

A solution of 4-chloro-1-(5-ethoxycarbonylpyrid-2-yl)-2-methylimidazo[4,5-c]pyridine in ethanol (100 ml) was hydrogenated over 30% palladium on carbon (3 g) and magnesium oxide (0.8 g) at 50 p.s.i. (345 kPa) for 30 hours. The mixture was filtered through Arbocel filter aid and the filter cake washed with boiling ethanol (6×50 ml). The filtrate was concentrated under reduced pressure yielding the title compound as a white foam, (2.75 g, 96%).

$^1$H-NMR (300 MHz methanol-$d_4$) 1.51 (3H, t, J 6Hz), 2.83 (3H, s), 4.53 (2H, q, J 6Hz), 7.70 (1H, d, J 4Hz), 7.92 (1H, d, J 6Hz), 8.43 (1H, d, J 4Hz), 8.72 (1H, d, J 6Hz), 8.97 (1H, s), 9.32 (1H, s).

(c) 6-(2-Methylimidazo[4,5-c]pyrid-1-yl)pyridine-3-carboxylic acid 1-(5-Ethoxycarbonylpyrid-2-yl)-2-methylimidazo[4,5-c]pyridine (2.75 g, 9.75 mmol) was dissolved in ethanol (15 ml) and 2N aqueous sodium hydroxide (5.8 ml) was added. The mixture was stirred for 3 days at room temperature and then the solvent was removed under reduced pressure. The residue was neutralised (pH6) with dilute hydrochloric acid, and the resulting precipitate was filtered off and dried in vacuo. The title compound was obtained as a white solid (1.70 g, 69%).

$^1$H-NMR (300 MHz, DMSO-$d_6$) 2.70 (3H, s), 7.58 (1H, d, J 4Hz), 7.93 (1H, d, J 6Hz), 8.36 (1H, d, J Hz), 8.58 (1H, d, J 6Hz), 8.96 (1H, s), 9.18 (1H, s).

(d) Ethyl 2-(2-methylimidazo[4,5-c]pyrid-1-yl)pyrid-5-oylacetate

The method of Preparation 1, Method C, (b) was followed substituting the pyridine-3-carboxylic acid from (c) above for 4-(2-methylimidazo[4,5-c]pyrid-1-yl)benzoic acid. The title compound was an orange gum.

$^1$H-NMR (300 MHz, $CDCl_3$) 1.40 (3H, t, J 6Hz), 2.80 (3H, s), 4.11 (2H, s), 4.35 (2H, q, J 6Hz), 7.40 (1H, d, J 4Hz), 7.58 (1H, d, J 6Hz), 8.38 (1H, d, J 4Hz), 8.57 (1H, d, J 6Hz), 9.10 (1H, s), 9.25 (1H, s).

PREPARATION 5

Ethyl 4'-[5-chloro-4-(1,3-dioxolan-2-yl)-2-methylimidazol-1-yl]benzoylacetate

(a) 5-Chloro-1-(4-cyanophenyl)-2-methylimidazole

A solution of 1-(4-cyanophenyl)-2-methylimidazole (3 g, 16.4 mmol) and N-chlorosuccinimide (2.18 g, 16.3 mmol) in chloroform (180 ml) was heated at reflux for 4 hours, then washed with water, dried over magnesium sulphate and evaporated to a yellow solid. Trituration with ether left a pale-yellow solid (2.38 g, 67%).

$^1$H-NMR (300 MHz $CDCl_3$) 2.30 (3H, s), 6.99 (1H, s), 7.43 (2H, d, J 8.5 Hz) and 7.88 (2H,d, J 8.5Hz).

(b) 5-Chloro-1-(4-cyanophenyl)-4-iodo-2-methylimidazole

Iodine chloride (3.2 g, 20 mmol) in acetic acid (10 ml) was added rapidly in drops to a stirred solution of the product from (a) (1.6 g, 7.3 mmol) and sodium acetate in acetic acid (40 ml). After heating at reflux for 2 hours, the mixture was evaporated to dryness and partitioned between saturated aqueous sodium bicarbonate (containing excess sodium thiosulphate) and dichloromethane. The organic layer was dried over magnesium sulphate and evaporated. Trituration with ether-pentane (1:1) afforded a pale-yellow solid (1.8 g, 72%)

$^1$H-NMR (300 MHz, $CDCl_3$) 2.30 (3H, s), 7.42 (2H, d, J 8.5Hz) and 7.88 (2H, d, J 8.5Hz).

(c) 5-Chloro-1-(4-cyanophenyl)-2-methylimidazole-4-carboxaldehyde

A solution of the product from (b) (1.03 g, 3 mmol) and tetrakis (triphenylphosphine)palladium (0.3 g) in THF (70 ml) was installed under an atmosphere of carbon monoxide and heated to 50° C. Tributyltin hydride (0.96 g, 3.3 mmol) in THF (40 ml) was instilled by motor-driven syringe over 4.5 hours. After an additional 0.5 hours the mixture was stirred with 100 ml of 10% potassium fluoride solution for 15 minutes, then extracted twice with dichloromethane. The organic layers were dried over magnesium sulphate and evaporated to an orange solid.

Flash chromatography (eluting ethyl acetate-ether=1:1) yielded a white solid (0.245 g, 33%).

$^1$H NMR (300 MHz $CDCl_3$) 2.34 (3H, s), 7.48 (2H,d J 8.3Hz), 7.95 (2H,d, J 8.3Hz) and 9.96 (1H,s).

(d) 5-Chloro-4-(1,3-dioxolan-2-yl)-1-(4-cyanophenyl)-2-methyl imidazole

A stirred solution of the aldehyde from (c) (0.24 g, 1mmol) and 4-toluenesulphonic acid hydrate (0.21 g, 1.1 mmol) and ethane-1,2-diol (0.5 ml, 8 mmol) in dichloromethane (8 ml) was heated at reflux through a Dean-Stark trap containing 4A molecular sieves for 6 hours. After standing at 25° C. for 70 hours the mixture was washed with aqueous sodium bicarbonate and evaporated to a yellow solid.

The residue was flash chromatographed (eluting ethyl acetate-methanol=9:1) to afford a white crystalline solid (0.13 g, 45%).

$^1$H-NMR (300 MHz $CDCl_3$) 2.30(3H,s), 4.08(2H,m), 4.31(2H,m), 5.95 (1H,s), 7.41(2H,d, J 8.3Hz), 7.88(2H, d, J 8.3Hz).

(e) Ethyl 4'-[5-chloro-3-(1,3-dioxolan-2-yl)-2-methylimidazol-1-yl]-benzoylacetate The nitrile obtained from (d) was treated as in Preparation 1 above to produce the title compound in a yield of 91%.

$^1$H-NMR (300 MHz, $CDCl_3$) 1.27(3H, t, J 7Hz), 2.27(3H,s), 4.04 (4H, br, s), 4.28(4H,m), 5.93(1H,s), 7.37(2H, d, J 8.3Hz), 8.12(2H, d, J 8.3Hz).

Methods of preparing other B-keto esters for use as intermediates in this invention are described in European patent application No. 88309039.1.

PREPARATION 6

7,8-Dimethyl-2-hydrazino-4-[4-(2-methylimidazo[4,5-c]pyrid-1-yl)phenyl]-3H-[1,5]benzodiazepine A mixture of 2,3-dihydro-7,8-dimethyl-4-[4-(2-methylimidazo[4,5-c]pyrid-1-yl)phenyl]-1H-[1,5]benzodiazepine-2-thione (411 mg, 1.0 mmol), hydrazine hydrate (60 mg, 1.2 mmol) and p-toluenesulphonic acid (10 mg) in n-butanol (5 ml) was heated at 100° C. for 1.5 hours. The solvent was removed under reduced pressure and the crude product was used directly for Examples 29–31.

PREPARATION 7

7,8-Dichloro-2-hydrazino-4-[4-(2-methylimidazo[4,5-c]pyrid-1-yl)phenyl]-3H-[1,5]benzodiazepine A mixture of 7,8-dichloro-2,3-dihydro-4-[4-(2-methylimidazo[4,5-c]pyrid-1-yl)phenyl]-1H-[1,5]benzodiazepin-2-thione (452 mg, 1.0 mmol), hydrazine hydrate (100 mg, 2 mmol) and red mercuric oxide (217 mg, 1.0 mmol) in n-butanol was heated at 100° C. for 30 minutes. The mixture was diluted with methanol (300 ml), filtered through Arbocel filter aid and the filtrate was concentrated under reduced pressure. The crude product was used directly for Example 32.

PREPARATION 8

4,5 Diamino-1-(1,1-dimethylethyl)-3-methylpyrazole (a) 5-Amino-1-(1,1-dimethylethyl)-3-methylpyrazole was treated with sodium nitrite in aqueous acetic acid according to the procedure described in *J. Amer. Chem. Soc.*, 1959, 81, 2456. The red solid product which precipitated from the reaction mixture was filtered off, washed with water, and dried in vacuo.

Yield 76%.

$^1$H-NMR (300 MHz $CDCl_3$) 1.62(9H,s), 2.68(3H,s), 7.10(2H, br s, exchanges with $D_2O$).

(b) 5-Amino-1-(1,1-dimethylethyl)-3-methyl-4-nitrosopyrazole (2.32 g, 12.7 mmol) obtained from (a) in ethanol (150 ml) was hydrogenated at 20 p.s.i. over 10% palladium on charcoal (230 mg) for 90 min. at room temperature. The catalyst was filtered off and the solvent was removed under reduced pressure to give the product as an unstable red solid (1.68 g, 73%).

PREPARATION 9

4,5-Diamino-1-(2-hydroxyethyl)-3-methylpyrazole (a)

5-Amino-1-(2-hydroxyethyl)-3-methyl-4-nitrosopyrazole

5-Amino-1-(2-hydroxyethyl)-3-methylpyrazole (Bull. soc. chim. France, 255 (1975)) (1.41 g, 10 mmoles) was dissolved in a mixture of water (7 ml) and glacial acetic acid (1.4 ml). Sodium nitrite (0.8 g, 11.6 mmoles) in water (7 ml) was added dropwise over 0.5 hour at 0° C. The red solution was stirred at 0° C., and after 1 hour, the solid which had precipitated was filtered off and dried in vacuo giving the title compound as a red solid (1.2 g, 70%).

$^1$H NMR (300 MHz, DMSO-$d_6$) 2.57(3H,s); 3.30(2H, br); 3.62 (2H,t, J=4Hz); 3.85 (2H,t, J=4Hz); 3.85 (2H,t,J=4Hz). 7.50(1H,broad).

(b) 4,5-Diamino-1-(2-hydroxyethyl)-3-methylpyrazole

5-Amino-1-(2-hydroxyethyl)-3-methyl-4-nitrosopyrazole (0.9 g, 5.3 mmole) was dissolved in a mixture of ethanol (40 ml) and dichloromethane (40 ml) and hydrogenated over 10% Pd/C (0.1 g) at 20 p.s.i. and 20° C. for 2 hours. The catalyst was filtered onto Arbocel and the solvent removed under reduced pressure yielding the title compound as a foam (800 mg, 97%).

$^1$H NMR (300MHz, $CDCl_3$) 2.15 (3H, s); 2.20 (5H, broad); 3.94 (2H, t,J 5Hz); 4.05 (2H,t,J 5Hz).

PREPARATION 10

4,5-Diamino-3-methyl-1-(2-pyridyl)pyrazole (a) 5-Amino-3-methyl-1-(2-pyridyl)pyrazole 3-Aminocrotonitrile (1.98 g, 24.1 mmol) was added to a stirred solution of 2-hydrazinopyridine (2.63 g, 24.1 mmol) in a mixture of concentrated hydrochloric acid (2.5 ml) and water (10 ml). After 10 minutes at room temperature, concentrated hydrochloric acid (5 ml) was added, and the mixture was heated for 30 minutes under reflux. The mixture was cooled and rendered basic by the addition of saturated aqueous potassium carbonate. The solid which precipitated was filtered off and dried to give the title compound, 2.43 g (58%).

$^1$H NMR(300MHz, $CDCl_3$), 2.25(3H,s), 5.37(1H,s), 5.92(2H, br s), 7.07(1H,m), 7.76(1H,m), 7.94(1H,d,J=7Hz), 8.32(1H,d,J=6Hz) ppm.

Analysis %: Found: C,62.05; H,5.77; N,32.25. $C_9H_{10}N_4$ requires C,62.05; H,5.79; N,32.16.

(b) 5-Amino-3-methyl-4-nitroso-1-(2-pyridyl)pyrazole

By the method of Preparation 8(a), 5-amino-3-methyl-1-(2-pyridyl)pyrazole (2.21 g, 12.7 mmol) was treated with sodium nitrite in aqueous acetic acid. The precipitated solid was triturated with methanol (250 ml), and the mother liquors were concentrated under reduced pressure to give the title compound as a red-brown solid (1.37 g, 53%).

$^1$HNMR (300MHz, $CDCl_3$), 2.84(3H,s), 7.22(1H,m), 7.88(1H,m), 7.97(1H,d,J=7Hz), 8.39(1H,d,J=3Hz), 9.20(2H,br s)ppm.

(c) 4,5-Diamino-3-methyl-1-(2-pyridyl)pyrazole

By the method of Preparation 8(b), 5-amino-3-methyl-4-nitroso-1-(2-pyridyl)pyrazole (1.37 g, 6.75 mmol) in ethanol/dichloromethane=4:1 (50 ml) was hydrogenated over 10% palladium on carbon at 20 p.s.i. to give the title compound (1.27 g, 100%).

$^1$HNMR (300MHz, $CDCl_3$), 2.24(3H,s) 7.05(1H,m), 7.77(1H,m), 7.89(1H,d,J=6Hz), 8.31(1H,d,J=3Hz)ppm. In addition a very broad resonance between 2 and 6 ppm was observed, presumably corresponding to the $NH_2$ groups.

PREPARATION 11

2-Hydroxyimino-3-oxo-3-phenylpropanenitrile

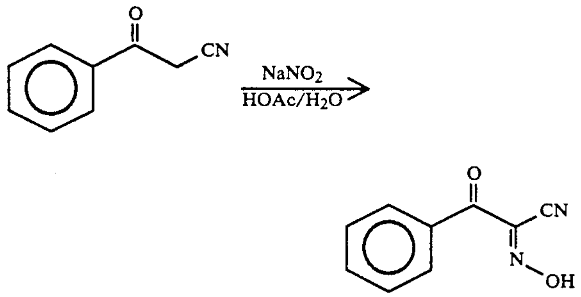

A suspension of benzoylacetonitrile (11.7 g, 80.7 mmol) in a mixture of glacial acetic (34 ml) and water (1 ml) was stirred vigorously at 10° C. whilst an aqueous solution of sodium nitrite (6.1 g, 88.4 mmol in 7 ml) was added dropwise over 30 minutes. The mixture was stirred for 1 hour at room temperature and then poured into iced water (600 ml). The yellow solid which precipitated was filtered off, washed with water (100 ml) and dried, giving the title compound, 7.8 g (56%). m.p. 126°-128° C. (literature m.p. 117°-119° C.; Ger. Offen. 2,722,416 (1978).

Analysis % Found: C,62.10; H,3.64; N,16.16. $C_9H_6N_2O_2$ requires C,62.07; H,3.47; N,16.08.

PREPARATIONS 12-18

The following 2-hydroxyimino-β-ketonitriles (Table 17) were prepared by the method of Preparation 11, starting with the corresponding β-ketonitrile, or, in the pyridyl-substituted cases, the sodium salt of the β-ketonitrile.

TABLE 17

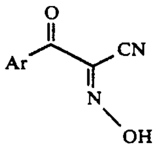

| Prep. | Ar | m.p. | Yield | Analysis % (Theoretical in brackets) C | H | N |
|---|---|---|---|---|---|---|
| 12 | 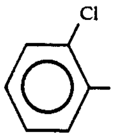 | 104-108° C. | 77% | | + | |

TABLE 17-continued

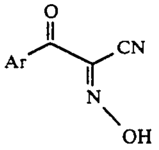

| Prep. | Ar | m.p. | Yield | Analysis % (Theoretical in brackets) C | H | N |
|---|---|---|---|---|---|---|
| 13 | 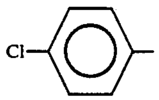 | 130-131° C. | 95% | | + | |
| 14 | 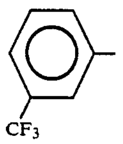 | oil | 56% | | + | |
| 15 | 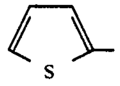 | 168-171° C. | 91% | 46.46 (46.66 | 2.18 2.24 | 15.37 15.55) |
| 16 | 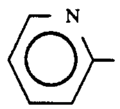 | 211-212° C. | 61% | 54.78 (54.86 | 3.08 2.88 | 23.39 23.89) |
| 17 | 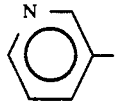 | 188-190° C. | 77% | 54.76 (54.86 | 2.93 2.88 | 24.02 23.89) |
| 18 | 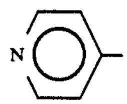 | 222-223° C. | 66% | 55.12 (54.86 | 2.89 2.88 | 23.55 23.99) |

+ Known compound: Ger Offen. 2,722,416 (1978)

PREPARATION 19

5-Amino-1-methyl-4-nitroso-3-phenylpyrazole

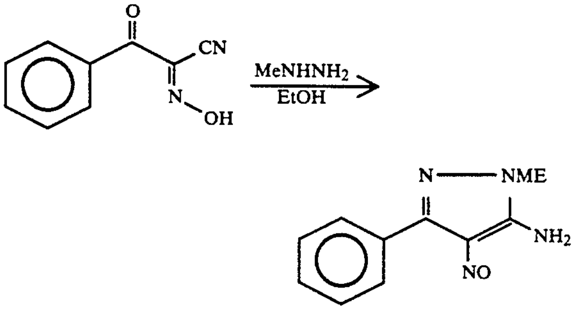

A mixture of 2-hydroxyimino-3-oxo-3-phenylpropanenitrile (2.61 g, 15 mmol) and methylhydrazine (1.1 ml, 21 mmol) was stirred at reflux in ethanol (20 ml) for 2 hours, cooled and concentrated under reduced pressure. The residue was partitioned between ether (50 ml) and dilute hydrochloric acid (50 ml, 2N solution). The aqueous phase was separated and rendered basic by the addition of saturated aqueous potassium carbonate.

The red solid which precipitated was filtered off and dried, to give the title compound, 1.40 g, (46%). m.p. 230°-231° C. (literature. m.p. 230°-231° C., Gazz. Chim. Ital., (1968), 98, 569.

PREPARATIONS 20-28

The following aminonitrosopyrazoles of Table 18 were prepared by the method of Preparation 19 starting with the corresponding 2-hydroxyimino-3-ketonitrile and substituted hydrazine.

TABLE 18

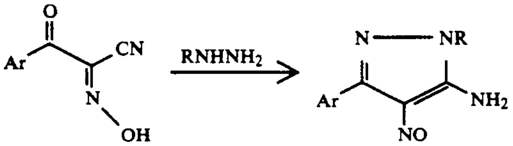

| Preparation | Ar | R | m.p. | Yield | Analysis % (Theoretical in brackets) C | H | N |
|---|---|---|---|---|---|---|---|
| 20 | 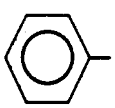 | 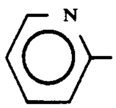 | 205-207° C. | 39% | 63.27<br>(63.39 | 4.20<br>4.18 | 26.24<br>26.40) |
| 21 | 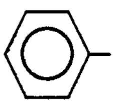 | $CH_2CH_2OH$ | 193-197° C. | 32% | 56.88<br>(56.89 | 5.17<br>5.21 | 23.90<br>24.12) |
| 22 | 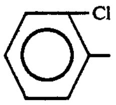 | $CH_3$ | 203-206° C. | 22% | 50.92<br>(50.75 | 3.92<br>3.83 | 23.49<br>23.67) |
| 23 | 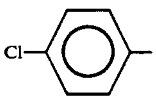 | $CH_3$ | 270-273° C. | 65% | 50.69<br>(50.75 | 3.74<br>3.63 | 23.58<br>23.68) |
| 24 | 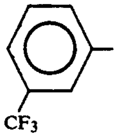 | $CH_3$ | 251-252° C. | 58% | 49.06<br>(48.89 | 3.41<br>3.36 | 20.37<br>20.74) |
| 25 | 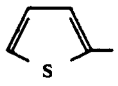 | $CH_3$ | 235-236° C. dec | 10% | 46.28<br>(46.14 | 3.72<br>3.87 | 26.71<br>26.91) |
| 26 | 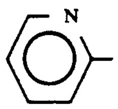 | $CH_3$ | 238-240° C. | 50% | 52.80<br>(53.20 | 4.46<br>4.46 | 34.77<br>34.46) |
| 27 | 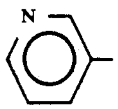 | $CH_3$ | 201-210° C. | 51% | 53.23<br>(53.20 | 4.52<br>4.46 | 34.47<br>34.46) |
| 28 | 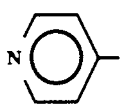 | $CH_3$ | 320-321° C. | 66% | 53.14<br>(53.20 | 4.34<br>4.46 | 34.14<br>34.46) |

PREPARATION 29

4,5-Diamino-1-methyl-3-(2-thienyl)pyrazole

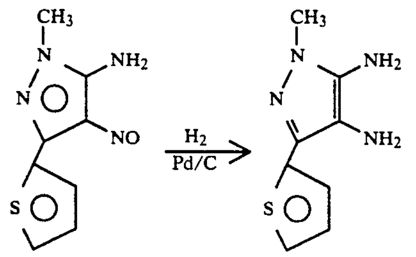

A suspension of 5-amino-4-nitroso-1-methyl-3-(2-thienyl)-pyrazole (1.255 g, 6.03 mmol) in ethanol (90 ml) was hydrogenated at 20 p.s.i. over 10% palladium on carbon (130 mg) at room temperature for 2 hours. The mixture was filtered through Arbocel filter aid and the filtrate was concentrated under reduced pressure to give the title compound as a red-brown solid (1.133 g, 97%), m.p. 154°-155° C.

$^1$HNMR (300MHz, $CDCl_3$)=2.60(2H, br s), 3.38(2H, br s), 3.74(3H,s), 7.11(1H,dd,J 2 and 3Hz), 7.27(1H,d,J 3Hz), 7.41(1H,d,J 2Hz).

PREPARATIONS 30-38

The diaminopyrazoles of Table 19 were prepared by the method of Preparation 29 using the aminonitrosopyrazoles of Preparations 20-28 as starting materials.

TABLE 19

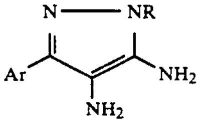

| Preparation | Ar | R | m.p. | Yield | $^1$H NMR (300MHz, $CDCl_3$ unless stated otherwise) |
|---|---|---|---|---|---|
| 30 | 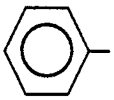 | 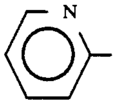 | 142-143° C. | 91% | 2.0-4.0(4H,br), 7.11(1H,m), 7.39-7.50(3H,m), 7.81(1H,m), 7.90(2H,d,J=6Hz), 8.08(1H,d,J=6Hz), 8.36(1H,dJ=4Hz)ppm. |
| 31 | 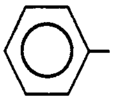 | $CH_2CH_2OH$ | >300° C. | 98% | (DMSO-$d_6$)3.40(2H, br s), 3.65(2H,m), 3.92(2H,t,J=5Hz), 4.58(2H,s), 4.92(1H,t,J=4Hz), 7.17(1H,t,J=5Hz), 7.31(2H,t,J=5Hz), 7.82(2H,d,J=5Hz)ppm. |
| 32 | 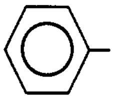 | $CH_3$ | 240-242° C.+ | 90% | 2.60(4H,br s), 3.75(3H,s), 7.34(1H,d,J=5Hz), 7.43(2H,t,J=5Hz), 7.56(2H,d,J=5Hz)ppm. |
| 33 | 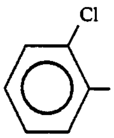 | $CH_3$ | 218-220° C.+ | 76% | (250MHz, DMSO-$d_6$), 3.55(3H,s), 5.63(2H, br s), 7.45(2H,m), 7.58(1H,dJ=6Hz) showing extra fine coupling), 7.65(1H,d,J=8Hz showing extra fine splitting), 8.42(2H,s)ppm. |
| 34 | 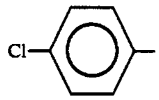 | $CH_3$ | 184-187° C.+ | 91% | (DMSO-$d_6$), 3.51(3H,d,J=1.5Hz), 7.25(2H,br s), 7.32(2H,m), 7.57(2H,m), 10.07(2H,br s)ppm. |
| 35 | 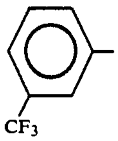 | $CH_3$ | 215-217° C.+ | 91% | ($CD_3O$), 3.78(3H,s) 7.76(1H,t,J=7Hz), 7.86(1H,d,J=7Hz), 7.92(1H,d,J=7Hz), 8.02(1H,s). |
| 36 | 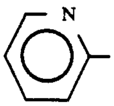 | $CH_3$ | 155-160° C. | 93% | 2.95(4H,br s), 3.78(3H,s), 7.12(1H,m) 7.69(1H,tJ=6Hz), 7.93(1H,d,J=6Hz), 8.55(1H,d,J=4Hz). |
| 37 | 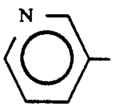 | $CH_3$ | 143-146° C. | 98% | 2.40(2H,br s), 3.40(2H,br s), 3.76(3H,s), 7.34(1H,m), 8.11(1H,d,J=6Hz), 8.56(1H,d,J=4Hz), 9.07(1H,s)ppm. |

TABLE 19-continued

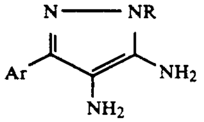

| Preparation | Ar | R | m.p. | Yield | $^1H$ NMR (300MHz, $CDCl_3$ unless stated otherwise) |
|---|---|---|---|---|---|
| 38 | 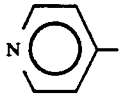 | $CH_3$ | 184–187° C. | 98° C. | (DMSO-$d_6$) 3.48(2H,br s), 3.55(3H,s), 4.74(2H,br s), 7.79(2H,d,J=5Hz), 8.45(2H,d,J=5Hz)ppm. |

+Dihydrochloride salt

PREPARATIONS 39–42

The compounds of Table 20 were prepared by the methods described in Ger. Offen. 2,023,453, and C. A. Rojahr, Ber., (1922), 55, 2959.

TABLE 20

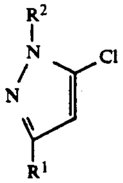

| Preparation | $R^1$ | $R^2$ | $^1H$ NMR (300MHz, $CDCl_3$) |
|---|---|---|---|
| 39 | $CH_3$ | 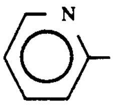 | 2.35(3H,s), 6.25(1H,s), 7.31(1H,m), 7.68(1H,d,J=5Hz), 7.83(1H,m), 8.58(1H,d,J=3Hz). |
| 40 | 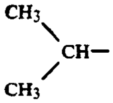 | $CH_3$ | 1.25(6H,d,J=5Hz), 2.90(1H,d,J=5Hz), 3.79(3H,sep), 6.03(1H,s). |
| 41 | 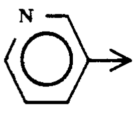 | $CH_3$ | 3.92(3H,s), 6.57(1H,s), 7.34(1H,dd,J=5 and 8Hz), 8.05(1H,dt,J=8 and 2Hz), 8.57(1H,dd,J=2 and 4 Hz 8.97(1H,d,J=2Hz). |
| 42 | 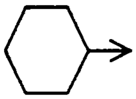 | H | (500MHz) 1.26(1H,m), 1.41(4H,m), 1.74(1H,d,J 13Hz), 1.82(2H,m), 1.99(2H,m), 3.73(1H,m), 5.97(1H,s). |

PREPARATION 43

4-Amino-3-(2-methoxyethoxy)methyl-5-methylaminopyrazole (a) 3-Bromomethyl-5-chloro-1-methyl-4-nitropyrazole 5-Chloro-1,3-dimethyl-4-nitropyrazole (43 g, 0.29 moles) was dissolved in carbon tetrachloride (430 ml), bromine (12 ml) was added and the reaction mixture stirred at reflux for 48 hours whilst illuminating with a 500 W light source. A second portion of bromine (12 ml) was added and the reaction mixture refluxed for a further 48 hours. The reaction mixture was cooled and chromatographed on silica (gradient elution commencing with hexane and increasing the proportion of dichloromethane from 0 to 100%). Fractions containing the product were evaporated yielding the title compound as a white solid. (35 g. 47%)

$^1H$ NMR. (300 MHz, $CDCl_3$) 3.92(3H,s), 4.64(2H,s).

(b)

3-(2-Methoxyethoxy)methyl-5-chloro-1-methyl-4-nitropyrazole

3-Bromomethyl-5-chloro-1-methyl-4-nitropyrazole (2.42 g, 9.5 mmoles), and silver tetrafluoroborate (2.22 g, 11.4 mmoles), were stirred at reflux in 2-methoxyethanol (25 ml) for 6 hours. The black solid was filtered off and the solvent removed under reduced pressure. The oil was dissolved in ethyl acetate (100 ml) and washed with water (100 ml). The organic phase was dried over magnesium sulphate and the solvent removed under reduced pressure. The product was purified by chromatography on silica eluting with 10% ethyl acetate in dichloromethane. Fractions containing product were evaporated yielding the title compound as a white solid (1.54 g, 65%).

$^1H$ NMR (300 MHz, $CDCl_3$) 3.41(3H,s), 3.63(2H,m), 3.81(2H,m); 3.92(3H,s), 4.90(2H,s)

(c)

3-(2-Methoxyethoxy)methyl-1-methyl-5-methylamino-4-nitropyrazole 3-(2-Methoxyethoxy)methyl-5-chloro-1-methyl-4-nitropyrazole (1.44 g, 5.8 mmoles) was suspended in ethanol. Methylamine was bubbled into the suspension for 20 minutes with ice cooling. The solution was then heated in a sealed vessel at 100° C. for 3 hours, cooled and the ethanol removed under reduced pressure. The yellow solid residue was dissolved in dichloromethane (150 ml) and washed with saturated sodium bicarbonate solution (50 ml). The organic phase was separated, dried over magnesium sulphate and the solvent removed under reduced pressure yielding the title compound as a yellow solid (1.34 g, 95%).

$^1H$ NMR (300 MHz, $CDCl_3$) 3.24(3H,d,J 5 Hz), 3.40(3H,s), 3.63(2H,t,J 4 Hz), 3.80(2H,t,J 4 Hz), 3.91(3H,s), 4.81(2H,s), 7.01 (1H,br s).

(d)

4-Amino-3-(2-methoxyethoxy)methyl-5-methylaminopyrazole 3-(2-Methoxyethoxy)methyl-1-methyl-5-methylamino-4-nitropyrazole (0.73 g, 3 mmoles), hydrazine hydrate (0.5 ml) and Raney nickel (200 mg) were stirred in ethanol (12 ml) at 50° C. for 1.5 hours. The Raney Nickel was filtered off and the ethanol removed under reduced pressure yielding the title compound (0.64 g, 100%).

$^1H$ NMR (300 MHz, $CDCl_3$) 2.83(6H, m), 3.39(3H,s), 3.58(2H,m), 3.65(2H,m); 3.68(3H,s), 4.58(2H,m).

.PREPARATIONS 44 AND 45

The compounds of Table 21 were made according to Preparation 11(b) using isobutanol or aqueous dimethylformamide instead of methoxyethanol.

TABLE 21

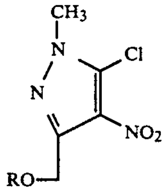

| Preparation | R | $^1H$ nmr |
|---|---|---|
| 44 | $CH_2CH(CH_3)_2$ | (300MHz,$CDCl_3$) 0.94(6H,d,J 5Hz), 1.96(1H,m) 3.39(2H,d,J 5Hz), 3.93(3H,s) 4.80(2H,s) |
| 45 | H | (300MHz,$CDCl_3$) 2.84(1H, br s); 3.93 (3H,s), 4.91(2H,s) |

PREPARATION 46

5-Chloro-3-cyclohexyl-1-methylpyrazole

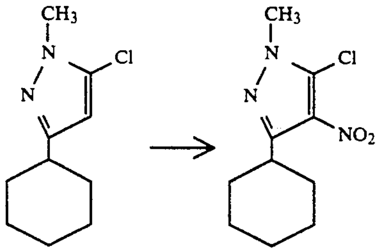

5-Chloro-3-cyclohexyl-1-methylpyrazole (prepared as in U.S. Pat. No. 4044013) (7.51 g, 37.8 mmoles), was dissolved in concentrated sulphuric acid (19 ml) and cooled to −10° C. Fuming nitric acid (12 ml) was added over 0.75 hours whilst keeping the temperature less than 0° C. The reaction mixture was stirred for 1 hour at 0° C. and then for 3 hours at 5° C. It was poured onto ice (250 ml) and extracted with dichloromethane (2×250 ml). The extracts were combined, dried over magnesium sulphate and the solvent removed under reduced pressure yielding the title compound as a white solid (7.7 g, 84%).

$^1H$ NMR (300 MHz, $CDCl_3$) 1.26-1.54(5H,m); 1.75-1.99(5H,m), 3.29(1H,m), 3.88(3H,s).

PREPARATIONS 47-50

The compounds of Table 22 were made according to the method of Preparation 46 using the appropriately substituted chloropyrazole and amine.

TABLE 22

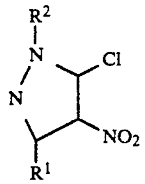

| Preparation | $R^1$ | $R^2$ | $^1H$ NMR (300MHz, $CDCl_3$) |
|---|---|---|---|
| 47 | $CH_3$ | 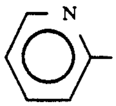 | 2.69(3H,s), 7.49(1H,dd, J=4 and 7Hz), 7.71(1H, d,J=7Hz), 8.00(1H,t,J=7Hz), 8.68(1H,d,J=4Hz). |
| 48 | i-Pr | $CH_3$ | 1.31(6H,d,J=5Hz), 3.62(1H,sep,J=5Hz), 3.88(3H,s). |
| 49 | 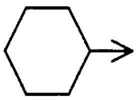 | H | 1.23-1.58(6H,m), 1.90(3H,m), 3.44(1H,m), 11.05(1H,br s). |
| 50 | 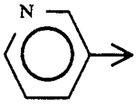 | $CH_3$ | 2.68(3H,s), 7.48(1H,m), 7.70(1H,d,J=6Hz), 7.98(1H,m), 8.65(1H,d,J=3Hz). |

PREPARATIONS 51-59

The compounds of Table 23 were made by the method of Preparation 43(c) using the appropriate substituted 5-chloropyrazole.

TABLE 23

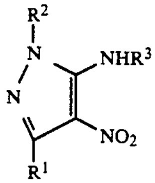

| Preparation | $R^1$ | $R^2$ | $R^3$ | $^1H$ NMR (300MHz,$CDCl_3$) |
|---|---|---|---|---|
| 51 | 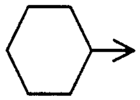 | $CH_3$ | $CH_3$ | 1.28-1.99(10H,m), 3.20(1H,m), 3.24(3H,d,J=4Hz, 3.87(3H,s), 7.15(1H,s). |
| 52 | 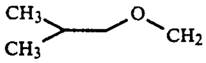 | $CH_3$ | $CH_3$ | 0.92(6H,d,J=5Hz), 1.97(1H,m), 3.24(3H,d,J=4Hz), 3.39(2H,d,J=5Hz), 3.92(3H,s), 4.71(2H,s), 7.01(1H,br s). |
| 53 | $CH_2OH$ | $CH_3$ | $CH_3$ | 3.17(1H,t,J=5Hz), 3.27(3H,d,J=5Hz), |

TABLE 23-continued

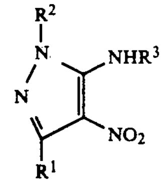

| Preparation | $R^1$ | $R^2$ | $R^3$ | $^1$H NMR (300MHz,$CDCl_3$) |
|---|---|---|---|---|
| | | | | 3.92(3H,s), 4.75(2H,d,J=5Hz), 7.10(1H,br s). |
| 54 | 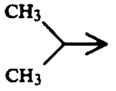 | $CH_3$ | $CH_3$ | 1.28(6H,d,J=6Hz), 3.23(3H,d,J=5Hz), 3.50(1H,septet), 3.87(3H,s), 7.16(1H, br s) |
| 55 | 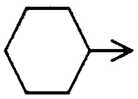 | $CH_3$ | H | 1.28(1H,m), 1.47(4H,m), 1.82(3H,m), 2.00(2H,m), 3.24(1H,m), 3.64(3H,s), 5.65(2H,br s). |
| 56 | 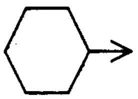 | H | $CH_3$ | 1.44(4H,m), 1.65(3H,m), 2.07(3H,m), 3.05(3H,d,J=4Hz), 3.26(1H,m), 3.45(3H,s), 6.52(1H,br s). |
| 57 | 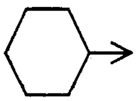 | H | $(CH_2)_4OH$ | 1.2-2.1(14H,complex), 3.30(1H,m), 3.50(2H,m), 3.35(2H,m), 6.85(1H,m). |
| 58 | 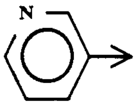 | $CH_3$ | $CH_3$ | 3.32(3H,d,J=5Hz), 4.02(3H,s), 7.23(1H,br s), 7.38(1H,dd,J=5 and 7Hz), 7.97(1H,d,J=7Hz), 8.68(1H,dd,J=5 and 2Hz), 8.87(1H,d,J=2Hz). |
| 59 | $CH_3$ | 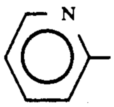 | $CH_3$ | 2.55(3H,s), 3.09(3H,d,J=4Hz), 7.28(1H,m), 7.89(2H,m), 8.45(1H,d,J=5Hz), 9.01(1H,br s). |

PREPARATIONS 60-68

The compounds of Table 24 were made according to the method of Preparation 43(d) using the appropriately substituted nitropyrazole.

TABLE 24

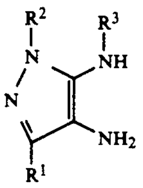

| Preparation | $R^1$ | $R^2$ | $R^3$ | $^1$H NMR (300MHz,$CDCl_3$) |
|---|---|---|---|---|
| 60 | 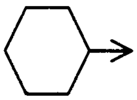 | $CH_3$ | $CH_3$ | 1.2-2.0(10H,m), 2.30(3H,m), 2.60(1H,t,J=5Hz), 2.80(3H,s), 3.63(3H,s). |

TABLE 24-continued
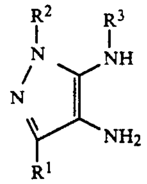
| Preparation | $R^1$ | $R^2$ | $R^3$ | $^1H$ NMR (300MHz, $CDCl_3$) |
|---|---|---|---|---|
| 61 | 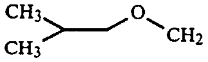 | $CH_3$ | $CH_3$ | 0.93(6H,d,J=5Hz), 1.92(1H,m), 2.60(3H,br s), 2.83(3H,s), 3.26(2H,d,J=5Hz), 3.68(3H,s), 4.48(2H,s). |
| 62 | $CH_2OH$ | $CH_3$ | $CH_3$ | 2.66(4H,br s), 2.82 (3H,s), 3.66(3H,s), 4.62(2H,s). |
| 63 | 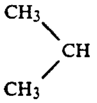 | $CH_3$ | $CH_3$ | 1.30(6H,d,J=5Hz), 2.40(2H, br s), 2.82(3H, br s), 2.98(1H,m) 2.80(2H,br s), 3.67(3H,s). |
| 64 | 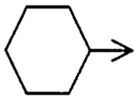 | $CH_3$ | H | Compound not isolated. |
| 65 | 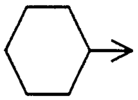 | H | $CH_3$ | Compound not isolated. |
| 66 | 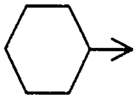 | H | $(CH_2)_4OH$ | 1.40(5H,m), 1.65-1.97(9H,m), 2.64(1H,m), 3.00(3H,br s), 3.29(2H,t,J=7Hz), 3.74(2H,m). |
| 67 | 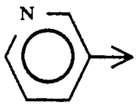 | $CH_3$ | $CH_3$ | 2.87(3H,s), 2.90(3H, br s), 3.79(3H,s), 7.33(1H,dd,J=5 and 7Hz), 8.10(1H,d,J=7Hz), 8.54(1H,d,J=5Hz), 9.05 (1H,s). |
| 68 | $CH_3$ | 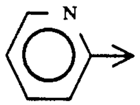 | $CH_3$ | 2.23(3H,s), 2.40(2H,br s), 3.13(3H,s), 7.03(1H,t,J=5Hz), 7.30(1H,br), 7.76(1H,t,J=5Hz), 7.90(1H,d,J=5Hz), 8.27(1H,d,J=5Hz). |

PREPARATION 69

Ethyl 3-[3-(2-methoxyethoxymethyl)-1-methyl-5-methylaminopyrazol-4-yl]amino-3-[4'-(2-methylimidazo[4,5-c]pyrid-l-yl)phenyl]propenoate

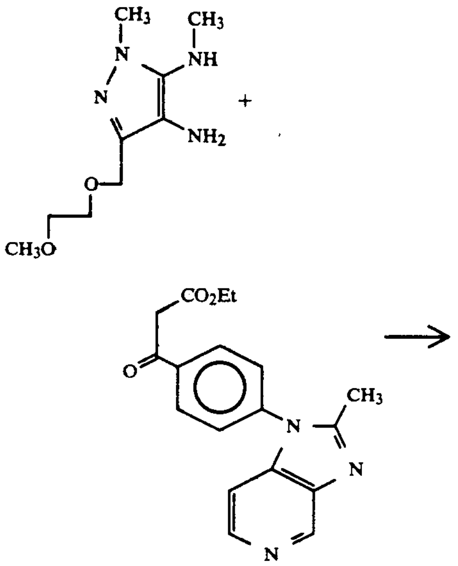

-continued

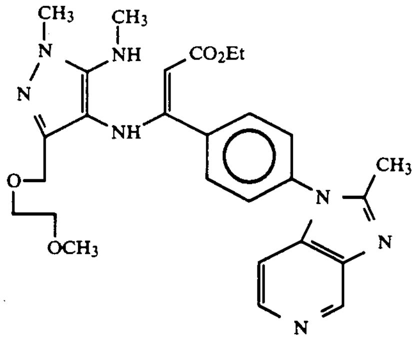

4-Amino-3-(2-methoxyethoxy)methyl-1-methyl-5-methylaminopyrazole (0.64 g, 3 mmoles), ethyl 4'-(2-methylimidazo[4,5-c]pyrid-l-yl)benzoyl acetate (0.97 g, 3 mmoles) and zinc chloride (0.8 g, 0.6 mmoles) were stirred in ethanol at reflux for 18 hours. The reaction mixture was cooled and the ethanol removed under reduced pressure. The residue was dissolved in dichloromethane (50 ml) and washed with saturated sodium bicarbonate solution. The organic phase was dried over magnesium sulphate and the solvent removed under reduced pressure. The dark red oil was chromatographed on silica eluting with 20% methanol in ethyl acetate. Fractions containing product were evaporated yielding the title compound as a fawn foam (0.72 g, 46%).

PREPARATIONS 70–72

The following compounds of Table 25 were made according to the method of Preparation 69 using the appropriately substituted diaminopyrazole.

TABLE 25

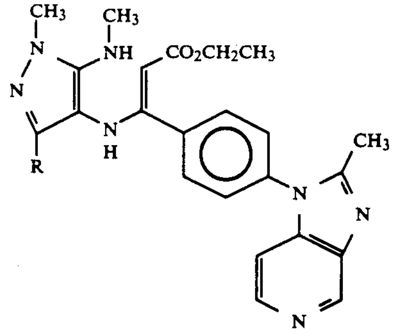

| Preparation | R | $^1H$ NMR(300MHz, $CDCl_3$) |
|---|---|---|
| 70 | 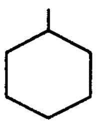 | 1.36(3H,t,J 5Hz); 1.24–1.80(10H,m); 2.36(1H,m); 2.52(3H,s), 2.84(3H,d,J 5Hz), 3.04(1H,t,J 5Hz), 3.58 (3H,s), 4.27(2H,q,J 5Hz), 5.04(1H,s), 7.01(1H,d,J 5Hz), 7.30(2H,d,J 6Hz), 7.76 (2H,d,J 6Hz),8.40(1H,d,J 5Hz), 9.06(1H,s), 9.60(1H,s). |
| 71 | 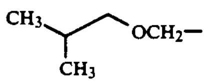 | 0.93(6H,d,J 5Hz), 1.36(3H,t,J 6Hz), 1.93(1H,m), 2.50(3H,s), 2.72(3H,d,J 5Hz), 2.90(1H,t,J 5Hz), 3.48 (2H,d,J 5Hz), 3.57(3H,s), 4.26(2H,q,J 6Hz), 4.30(2H,s), 5.02(1H,s), 7.03(1H,d,J 5Hz), 7.25(2H,q,J 6Hz), 7.68 (2H,d,J 6Hz), 8.38(1H,d,J 5Hz), 9.06(1H,s); 9.78(1H,s). |
| 72 | $HOCH_2$— | 1.36(3H,t,J 6Hz), 1.82(1H,t,J 5Hz), 2.56(3H,s), 2.82(3H,d,J 5Hz), 3.02(1H,m); 3.60 (3H,s); 4.26(2H,q,J 6Hz), |

TABLE 25-continued

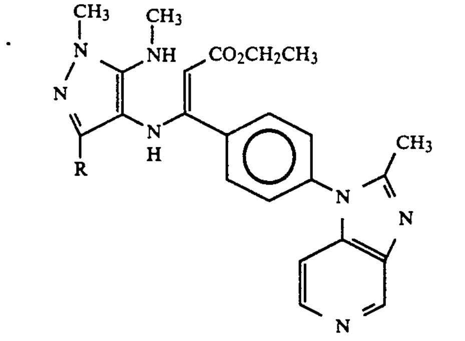

| Preparation | R | $^1H$ NMR(300MHz, $CDCl_3$) |
|---|---|---|
| | | 4.45(2H,d,J 5Hz), 5.06(1H,s), 7.06 (1H,d,J 5Hz), 7.27(2H,d,J 6Hz), 7.62 (2H,d,J 6Hz), 8.40(1H,d,J 5Hz), 9.08(1H,s), 9.58(1H,s) |

PREPARATION 73

3-Amino-2-methylaminoquinoline (a) Gaseous methylamine was bubbled through a suspension of 2-chloro-3-nitroquinoline (1.06 g, 5.1 mmol) in ethanol (20 ml) at 0° C. for 15 minutes. The solvent was removed under reduced pressure and the bright red residue was dissolved in dichloromethane (100 ml) and washed with saturated aqueous sodium bicarbonate (50 ml). The organic layer was dried ($MgSO_4$) and concentrated under reduced pressure to give 2-methylamino-3-nitroquinoline (940 mg, 91%) as a red solid, m.p. 160° C.

$^1H$ NMR (300 MHz, $CDCl_3$), 3.26(3H,d,J 4 Hz), 7.30(1H,m), 7.74(3H,m), 7.85(1H, br s), 8.97(1H,s).

(b) 2-Methylamino-3-nitroquinoline (711 mg, 3.5 mmol) was reduced according to the procedure of Preparation 11 (d) to give the title compound, (590 mg, 97%), m.p. 133°-136° C.

Analysis %:

Found: C,68.10; H,6.38; N,23.58.

$C_{10}H_{11}N_3$. $0.2H_2O$ requires C,67.92; H,6.49; N,23.76.

The following compounds were prepared by the methods described in the respective publications below:

2,3-Diamino-4,6-dimethylpyridine *Bull. Chem. Soc. Jp.*, 1973, 46 3277-3280

2,3-Diamino-4-methylpyridine ) W. German OLS 2305339

2,3-Diamino-6-methylpyridine )

3,4-Diamino-2,6-dimethyl pyridine *Chem. Abs.*, 63, 162996

3,4-Diamino-2-methoxycarbonyl-5-methylthiophene *Pharmazie*, 1970, 25, 517

4,5-Diamino-3-methyl-l-phenylpyrazole *J. Het. Chem*, 1975, 12, 279

4,5-Diamino-1-methyl-3-phenylpyrazole *Farmaco Ed. Sci.*, 1982, 37, 116

4,5-Diamino-1,3-dimethylpyrazole *Chem-Ztg.*, 1977, 101, 262.

3,4-Diamino-1,5-dimethylpyrazole *ZH. Obsch. Khim.*, 1980, 50, 2106.

We claim:

1. A compound of formula (I), (II) or (III)

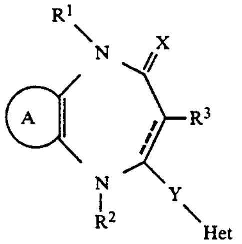

(I)

or

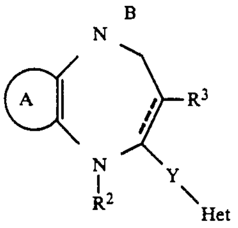

(II)

or

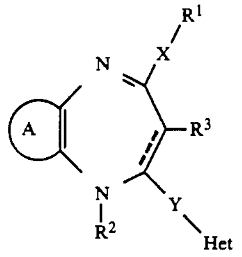

(III)

wherein;

A represents a fused benzene, pyridine, naphthalene, quinoline, thiophene, benzothiophene, pyrazole or isothiazole ring, which ring or rings being optionally substituted by 1 or 2 substituents independently selected from $C_1$-$C_4$ alkyl; $C_4$-$C_7$ cycloalkyl; halo; perfluoro - ($C_1$-$C_4$ alkyl); cyano; ($C_1$-$C_4$ alkoxy)-carbonyl; nitro; amino; amino substituted by ($C_1$-$C_4$ alkyl) sulfonyl, amino substituted by ($C_1$-$C_4$ alkyl)-oxalyl; $C_1$-$C_4$ alkoxy - ($C_1$-$C_4$ alkyl) imino; hydroxy ($C_1$-$C_4$ alkyl), ($C_1$-$C_4$ alkoxy)-$C_1$-$C_4$ alkyl, ($C_1$-$C_4$ alkoxy)-($C_2$-$C_4$ alkoxy)-$C_1$-$C_4$ alkyl, —$CONR^5R^6$ wherein $R^5$ and $R^6$ are each independently H or $C_1$-$C_6$ alkyl, or $R^5$ is H or $C_1$-$C_4$ alkyl and $R^6$ is $C_3$-$C_7$ cycloalkyl, or 2-pyridyl, or $R^5$ or $R^6$ are joined together to form, with the nitrogen atom to which they are attached, a morpholino, pyrrolidino or piperidino group; and phenyl, thienyl or pyridyl optionally substituted by halogen, cyano, trifluoromethyl, ($C_1$-$C_4$ alkoxy) carbonyl or carbamoyl, X is O, S or NH Y is 1, 4 phenylene or a group of formula

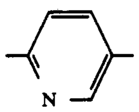

$R^1$ is either H or $C_1$–$C_4$ alkyl optionally substituted by a substituent selected from hydroxyl, phenyl, halophenyl, pyridyl, ($C_1$–$C_4$ alkoxy) carbonyl, and di ($C_1$–$C_4$ alkyl) amino or is $C_2$–$C_4$ alkyl substituted by hydroxy or by one or two $C_1$–$C_4$ alkoxy groups or $(CH_2)_nCONR^7R^8$ where n=1–4 and $R^7$ and $R^8$ are each independently H or $C_1$–$C_4$ alkyl.

$R^2$ is H or $C_1$–$C_4$ alkyl;

$R^3$ is H or $C_1$–$C_4$ alkyl;

the fused ring B is an imidazole, triazole, tetrazole, pyrimidine, imidazoline or tetrahydropyrimidine ring, said fused ring B being optionally substituted by 1 or 2 substituents independently selected from $C_1$–$C_4$ alkyl, $C_1$–$C_4$ haloalkyl, halo and oxo;

and "Het" is pyridyl, 1,2,4-triazolyl or imidazolyl said "Het" rings optionally fused to a benzene, thiazole or pyridine ring and at least one of said rings optionally being substituted with from one to three substituents independently selected from $C_1$–$C_4$ alkyl, $C_1$–$C_4$ alkoxy, halo, $CF_3$, CN and formyl; and wherein the dashed line represents an optional bond; and their pharmaceutically acceptable salts.

2. A compound according to claim 1, in which A is a fused benzene, dimethylbenzene, dichlorobenzene, nitrobenzene, aniline, fluorobenzene, chloro-benzene, pyridine, quinoline, methylpyridine, dimethylpyridine, ethoxycarbonylpyridine, pyrid-2-yl carbamoylpyridine, morpholinocarbonylpyridine, diethylcarbamoylpyridine, t-butylcarbamoylpyridine, thiophene, 2-methoxycarbonyl-5-methyl-thiophene, 1-methyl-3-phenylpyrazole, 1-phenyl-3-methylpyrazole, 1-methyl-3-t-butylpyrazole, 1,2-dimethylpyrazole, 1,3-dimethylpyrazole, 1-pyrid-2-yl-3-methyl-pyrazole, 1-t-butyl-3-methylpyrazole, 1(2-hydroxyethyl)-3-methylpyrazole, 1-methyl-3-pyrid-3-ylpyrazole, 1-methyl-3-pyrid-4-ylpyrazole, 1-methyl-3-pyrid-2-ylpyrazole, 1-(2-hydroxyethyl)-3-phenyl-pyrazole, 3-(2-methoxy-ethoxy)methyl-1-methylpyrazole, 1-methyl-3-cyclohexylpyrazole, 1-methyl-3-hydroxy-methylpyrazole, 3-cyclohexylpyrazole, 1-methyl-3-isobutoxymethyl)-pyrazole, 1-methyl-3-(4-chlorophenyl)pyrazole, 1-methyl-3-isopropyl pyrazole, 1-pyrid-2-yl-3-phenylpyrazole, 1-methyl-3-(2-chlorophenyl)pyrazole, 1-methyl-3-3-(trifluoromethyl)phenylpyrazole, 1-methyl-3-thienyl pyrazole, bromopyridine, 1-ethoxyethylimino benzene, N-ethylsulphoxyaniline, 3-methylisothiazole or ethoxycarbonylcarbamidobenzene ring.

3. A compound according to claim 2, in which $R^1$ is H, methyl, ethyl, benzyl, 4-chlorobenzyl, $—CH_2CO_2Et$, $—CH_2CH_2N(CH_3)_2$, $—CH_2CON(CH_3)_2$, $—CH_2CH_2CH(OCH_3)_2$ or 4-hydroxybutyl.

4. A compound according to claim 3, in which $R^2$ and $R^3$ are independently hydrogen or methyl.

5. A compound according to claim 4, in which "Het" is 2-methylimidazo[4,5-c]pyrid-1-yl, 2,4,6-trimethylimidazo[4,5-c]pyrid-1-yl, 3,5-dimethyl-1,2,4-triazol-4-yl, 1,6-dimethylpyrid-3-yl, 5-chloro-2-methylimidazol-1-yl, 5-chloro-4-formyl-2-methylimidazo-1-yl or 4-methylimidazo [2,1-b]thiazol-5-yl.

6. 8,9-dichloro-5-[4-(2-methyl-1H-imidazo[4,5-c]pyrid-1-yl)phenyl]-4H-imidazo[1,2-a]-[1,5]benzodiazepine;

8,9-dichloro-1-methyl-5-[4-(2-methylimidazo[4,5-c]pyrid-1-yl)phenyl]-4H-imidazo-[1,2-a][1,5]benzodiazepine;

3,5-dihydro-2-[4-(2-methylimidazo[4,5-c]pyrid-1-yl)phenyl]-5,7,9-trimethyl-1H-pyrido[2,3-b][1,4]diazepin-4-one;

8-bromo-3,5-dihydro-1-methyl-2-[4-(2-methylimidazo[4,5-c]pyrid-1-yl)-phenyl]-4H-pyrido[2,3-b][1,4]diazepin-4-one;

1,3-dihydro-1,8-dimethyl-6-methoxycarbonyl-4-[4-(2-methylimidazo[4,5-c]pyrid-1-yl)-phenyl]-2H-thieno[3,4-b]diazepin-2-one;

5-[4-(2-methylimidazo[4,5-c]pyrid-1-yl)phenyl]-1,6,7,8-tetrahydro-1,3,8-trimethyl-pyrazolo[3,4-b][1,4]diazepin-7-one.

3-cyclohexyl-1,8-dimethyl-5-[4-(2-methylimidazo[4,5-c]pyrid-1-yl)phenyl]-1,6,7,8-tetrahydropyrazolo[3,4-b][1,4]diazepin-7-one;

8-bromo-5-[4-(2-methylimidazo[4,5-c]pyrid-1-yl)phenyl-4H-imidazo[1,2-g]pyrido[2,3-b][1,4]diazepine or 1,6,7,8-tetrahydro-1,8-dimethyl-5-[4-(2-methyl-1H-imidazo[4,5-c]pyrid-1-yl)phenyl]-7-oxo-3-(3-pyridyl)-pyrazolo[3,4-b][1,4]diazepine;

and their pharmaceutically acceptable salts.

7. A medicament comprising a compound for antagonising platelet activating factor of claim 1 and a pharmaceutically acceptable diluent or carrier wherein the medicament comprises 0.1 mg to 1000 mg of the claim 1 compound and the remainder is the diluent or carrier.

* * * * *